US012721682B2

(12) United States Patent
Ryan et al.

(10) Patent No.: US 12,721,682 B2
(45) **Date of Patent: *Sep. 1, 2026**

(54) SYSTEMS, METHODS, AND DEVICES FOR DEVELOPING PATIENT-SPECIFIC SPINAL TREATMENTS, OPERATIONS, AND PROCEDURES

(71) Applicant: Medicrea International, Rillieux-la-Pape (FR)

(72) Inventors: David Ryan, Rochetaillee sur Saone (FR); Denys Sournac, Reyrieux (FR); Thomas Mosnier, Rochetaillée sur Saône (FR); Christophe X. Javelot, Porte des Pierres Dorees (FR); Agathe Senac, Villeurbanne (FR); Céline Augagneur, Lyons (FR)

(73) Assignee: MEDICREA INTERNATIONAL (FR)

( * ) Notice: Subject to any disclaimer, the term of this patent is extended or adjusted under 35 U.S.C. 154(b) by 52 days.

This patent is subject to a terminal disclaimer.

(21) Appl. No.: 18/739,125

(22) Filed: Jun. 10, 2024

(65) Prior Publication Data

US 2024/0325085 A1 Oct. 3, 2024

Related U.S. Application Data

(63) Continuation of application No. 17/496,222, filed on Oct. 7, 2021, now Pat. No. 12,004,814, which is a (Continued)

(51) Int. Cl.

*A61B 34/10* (2016.01)
*A61B 17/70* (2006.01)

(Continued)

(52) U.S. Cl.

CPC .......... *A61B 34/10* (2016.02); *A61B 17/7002* (2013.01); *A61B 34/20* (2016.02);

(Continued)

(58) Field of Classification Search

CPC .............. A61B 34/10; A61B 2034/101; A61B 2034/102; A61B 2034/105;

(Continued)

(56) References Cited

U.S. PATENT DOCUMENTS 4,382,438 A 5/1983 Jacobs
5,006,984 A 4/1991 Steele (Continued)

FOREIGN PATENT DOCUMENTS

AU 2012289973 A1 * 3/2014 ......... A61F 2/30942
JP 2011218180 A 11/2011

(Continued)

OTHER PUBLICATIONS

Abe et al. “Scoliosis corrective force estimation from the implanted rod deformation using 3 D Fem analysis”, 2015, Scoliosis 10(Suppl 2):52, 6 pages.

(Continued)

*Primary Examiner* — Eduardo C Robert
*Assistant Examiner* — Tara Rose E Carter
(74) *Attorney, Agent, or Firm* — FOX ROTHSCHILD LLP

(57) ABSTRACT

The disclosure herein relate to systems, methods, and devices for developing patient-specific spinal treatments, operations, and procedures. In some embodiments, systems, methods, and devices described herein for developing patient-specific spinal treatments, operations, and procedures can comprise an iterative virtuous cycle. The iterative virtuous cycle can further comprise pre-operative, intra-operative, and post-operative techniques or processes. For example, the iterative virtuous cycle can comprise imaging analysis, case simulation, implant production, case support, data collection, machine learning, and/or predictive model- (Continued)

ing. One or more techniques or processes of the iterative virtuous cycle can be repeated.

18 Claims, 26 Drawing Sheets

Related U.S. Application Data continuation of application No. 15/958,409, filed on Apr. 20, 2018, now Pat. No. 11,185,369.

(60) Provisional application No. 62/612,260, filed on Dec. 29, 2017, provisional application No. 62/597,035, filed on Dec. 11, 2017, provisional application No. 62/518,310, filed on Jun. 12, 2017, provisional application No. 62/518,305, filed on Jun. 12, 2017, provisional application No. 62/488,077, filed on Apr. 21, 2017.

(51) Int. Cl.

| | |
|---|---|
| ***A61B 34/00*** | (2016.01) |
| ***A61B 34/20*** | (2016.01) |
| ***A61B 90/00*** | (2016.01) |
| ***A61F 2/46*** | (2006.01) |
| ***G16H 50/50*** | (2018.01) |
| ***G16H 50/70*** | (2018.01) |

(52) U.S. Cl.

CPC ............. *G16H 50/50* (2018.01); *G16H 50/70* (2018.01); *A61B 17/7001* (2013.01); *A61B 17/7074* (2013.01); *A61B 2034/101* (2016.02); *A61B 2034/104* (2016.02); *A61B 2034/108* (2016.02); *A61B 2034/2048* (2016.02); *A61B 34/25* (2016.02); *A61B 2034/252* (2016.02); *A61B 2034/256* (2016.02); *A61B 2090/376* (2016.02); *A61B 2090/3762* (2016.02); *A61F 2/4657* (2013.01)

(58) Field of Classification Search

CPC ........ A61B 2034/106; A61B 2034/107; A61B 2034/108; A61B 34/20; A61B 2034/2046; A61B 2034/2048; A61B 2034/2051; A61B 2034/2053; A61B 2034/2055; A61B 2034/2057; A61B 2034/2059; A61B 2034/2061; A61B 2034/2063; A61B 2034/2065

See application file for complete search history.

(56) References Cited

U.S. PATENT DOCUMENTS

| | | | |
|---|---|---|---|
| 5,163,440 | A | 11/1992 | DeLuca et al. |
| 5,209,752 | A | 5/1993 | Ashman et al. |
| 5,224,035 | A | 6/1993 | Yamashita et al. |
| 5,251,127 | A | 10/1993 | Raab |
| 5,291,901 | A | 3/1994 | Graf |
| 5,305,203 | A | 4/1994 | Raab |
| 5,312,405 | A | 5/1994 | Korotko et al. |
| 5,413,116 | A | 5/1995 | Radke et al. |
| 5,514,180 | A | 5/1996 | Heggeness et al. |
| 5,667,506 | A | 9/1997 | Sutterlin |
| 5,748,767 | A | 5/1998 | Raab |
| 5,785,663 | A | 7/1998 | Sarvazyan |
| 6,015,409 | A | 1/2000 | Jackson |
| 6,213,958 | B1 | 4/2001 | Winder |
| 6,282,437 | B1 | 8/2001 | Franck et al. |
| 6,302,888 | B1 | 10/2001 | Mellinger et al. |
| 6,364,849 | B1 | 4/2002 | Wilcox |
| 6,385,475 | B1 | 5/2002 | Cinquin et al. |
| 6,409,684 | B1 | 6/2002 | Wilk |
| 6,443,953 | B1 | 9/2002 | Perra et al. |
| 6,499,488 | B1 | 12/2002 | Hunter et al. |
| 6,565,519 | B2 | 5/2003 | Benesh |
| 6,585,666 | B2 | 7/2003 | Suh et al. |
| 6,711,432 | B1 | 3/2004 | Krause et al. |
| 6,715,213 | B2 | 4/2004 | Richter |
| 6,716,213 | B2 | 4/2004 | Shitoto |
| 6,746,449 | B2 | 6/2004 | Jones et al. |
| 6,786,930 | B2 | 9/2004 | Biscup |
| 7,066,938 | B2 | 6/2006 | Slivka et al. |
| 7,338,526 | B2 | 3/2008 | Steinberg |
| 7,509,183 | B2 | 3/2009 | Lin et al. |
| 7,534,263 | B2 | 5/2009 | Burdulis, Jr. et al. |
| 7,542,791 | B2 | 6/2009 | Mire et al. |
| 7,570,791 | B2 | 8/2009 | Frank et al. |
| 7,606,613 | B2 | 10/2009 | Simon et al. |
| 7,611,522 | B2 | 11/2009 | Gorek |
| 7,618,451 | B2 | 11/2009 | Berez et al. |
| 7,634,119 | B2 | 12/2009 | Tsougarakis et al. |
| 7,635,367 | B2 | 12/2009 | Groiso |
| 7,639,866 | B2 | 12/2009 | Pomero et al. |
| 7,660,623 | B2 | 2/2010 | Hunter et al. |
| 7,674,293 | B2 | 3/2010 | Kuiper et al. |
| 7,715,602 | B2 | 5/2010 | Richard |
| 7,763,054 | B2 | 7/2010 | Clement et al. |
| 7,824,413 | B2 | 11/2010 | Varieur et al. |
| 7,835,778 | B2 | 11/2010 | Foley et al. |
| 7,840,253 | B2 | 11/2010 | Tremblay et al. |
| 7,862,593 | B2 | 1/2011 | Clement et al. |
| 7,918,887 | B2 | 4/2011 | Roche |
| 7,953,471 | B2 | 5/2011 | Clayton et al. |
| 7,974,677 | B2 | 7/2011 | Mire et al. |
| 7,981,158 | B2 | 7/2011 | Fitz et al. |
| 7,996,061 | B2 | 8/2011 | Mollard et al. |
| 7,996,064 | B2 | 8/2011 | Simon et al. |
| 8,000,926 | B2 | 8/2011 | Roche et al. |
| 8,036,441 | B2 | 10/2011 | Frank et al. |
| 8,038,716 | B2 | 10/2011 | Duggal et al. |
| 8,046,050 | B2 | 10/2011 | Govari et al. |
| 8,066,708 | B2 | 11/2011 | Lang et al. |
| 8,077,950 | B2 | 12/2011 | Tsougarakis et al. |
| 8,083,778 | B2 | 12/2011 | Clement et al. |
| 8,105,330 | B2 | 1/2012 | Fitz et al. |
| 8,142,842 | B2 | 3/2012 | Sugita et al. |
| 8,196,825 | B2 | 6/2012 | Turner et al. |
| 8,211,109 | B2 | 7/2012 | Groiso |
| 8,211,153 | B2 | 7/2012 | Shaolian et al. |
| 8,234,097 | B2 | 7/2012 | Steines et al. |
| 8,241,296 | B2 | 8/2012 | Wasielewski |
| 8,246,680 | B2 | 8/2012 | Betz et al. |
| 8,265,790 | B2 | 9/2012 | Amiot et al. |
| 8,270,253 | B1 | 9/2012 | Roche et al. |
| 8,275,594 | B2 | 9/2012 | Lin et al. |
| 8,308,772 | B2 | 11/2012 | Clement et al. |
| 8,308,775 | B2 | 11/2012 | Clement et al. |
| 8,337,501 | B2 | 12/2012 | Fitz et al. |
| 8,357,111 | B2 | 1/2013 | Caillouette et al. |
| 8,357,166 | B2 | 1/2013 | Aram et al. |
| 8,372,075 | B2 | 2/2013 | Groiso |
| 8,377,073 | B2 | 2/2013 | Wasielewski |
| 8,394,142 | B2 | 3/2013 | Bertagnoli et al. |
| 8,398,681 | B2 | 3/2013 | Augostino et al. |
| 8,400,312 | B2 | 3/2013 | Hotokebuchi et al. |
| 8,414,592 | B2 | 4/2013 | Quirno |
| 8,442,621 | B2 | 5/2013 | Gorek et al. |
| 8,457,930 | B2 | 6/2013 | Schroeder |
| 8,465,527 | B2 | 6/2013 | Clement |
| 8,494,805 | B2 | 7/2013 | Roche et al. |
| 8,506,632 | B2 | 8/2013 | Ganem et al. |
| 8,532,806 | B1 | 9/2013 | Masson |
| 8,535,337 | B2 | 9/2013 | Chang et al. |
| 8,549,888 | B2 | 10/2013 | Isaacs |
| 8,556,983 | B2 | 10/2013 | Bojarski et al. |
| 8,588,892 | B2 | 11/2013 | Hladio et al. |
| 8,636,776 | B2 | 1/2014 | Rosenberg et al. |
| 8,672,948 | B2 | 3/2014 | Lemaitre |
| 8,685,093 | B2 | 4/2014 | Anderson et al. |
| 8,690,888 | B2 | 4/2014 | Stein et al. |
| 8,705,829 | B2 | 4/2014 | Frank et al. |

(56) References Cited

U.S. PATENT DOCUMENTS 8,718,820 B2 5/2014 Amiot et al.
8,758,357 B2 6/2014 Frey
8,775,133 B2 7/2014 Schroeder
8,777,877 B2 7/2014 Stein et al.
8,784,339 B2 7/2014 Stein et al.
8,801,786 B2 8/2014 Bernard et al.
8,814,877 B2 8/2014 Wasielewski
8,814,915 B2 8/2014 Hess et al.
8,852,237 B2 10/2014 Kalfas et al.
8,855,389 B1 10/2014 Hoffmann et al.
8,864,764 B2 10/2014 Groiso
8,870,889 B2 10/2014 Frey
8,900,316 B2 12/2014 Lenz et al.
8,911,448 B2 12/2014 Stein
8,926,673 B2 1/2015 Clement et al.
8,945,133 B2 2/2015 Stein et al.
8,956,416 B2 2/2015 McCarthy
8,974,467 B2 3/2015 Stone
8,983,813 B2 3/2015 Miles et al.
8,998,962 B2 4/2015 Birch
9,011,448 B2 4/2015 Roche et al.
9,034,037 B2 5/2015 Fiere et al.
9,039,772 B2 5/2015 Park et al.
9,056,017 B2 6/2015 Kotlus
9,066,701 B1 6/2015 Finley et al.
9,066,734 B2 6/2015 Schoenefeld et al.
9,078,755 B2 7/2015 Mahfouz
9,101,492 B2 8/2015 Mangione et al.
9,115,998 B2 8/2015 Proulx et al.
9,119,572 B2 9/2015 Gorek et al.
9,119,671 B2 9/2015 Kast
9,125,680 B2 9/2015 Kostrzewski et al.
9,144,440 B2 9/2015 Aminian
9,144,470 B2 9/2015 Proulx et al.
9,168,153 B2 10/2015 Bettenga
9,173,661 B2 11/2015 Metzger et al.
9,180,015 B2 11/2015 Fitz et al.
9,192,412 B2 11/2015 Meyrat et al.
9,198,678 B2 12/2015 Frey et al.
9,232,955 B2 1/2016 Bonin, Jr. et al.
9,233,001 B2 1/2016 Miles et al.
9,237,952 B2 1/2016 Kurtz
9,248,023 B2 2/2016 Ries et al.
9,250,620 B2 2/2016 Kotlus
9,278,010 B2 3/2016 Gibson et al.
9,283,048 B2 3/2016 Kostrzewski et al.
9,289,221 B2 3/2016 Gelaude et al.
9,289,270 B2 3/2016 Gielen et al.
9,295,482 B2 3/2016 Fitz et al.
9,295,497 B2 3/2016 Schoenefeld et al.
9,295,561 B2 3/2016 Ball et al.
9,301,768 B2 4/2016 Buza et al.
9,308,050 B2 4/2016 Kostrzewski et al.
9,308,091 B2 4/2016 Lang
9,314,275 B2 4/2016 Clement et al.
9,314,343 B2 4/2016 Parisi et al.
9,320,547 B2 4/2016 Augostino
9,320,604 B2 4/2016 Miles et al.
9,326,780 B2 5/2016 Wong et al.
9,339,277 B2 5/2016 Jansen et al.
9,345,492 B2 5/2016 Stein et al.
9,358,051 B2 6/2016 Sournac et al.
9,358,130 B2 6/2016 Livorsi et al.
9,358,136 B2 6/2016 Stein et al.
9,364,370 B2 6/2016 Kuhnel
9,381,085 B2 7/2016 Axelson, Jr. et al.
9,387,015 B2 7/2016 Taylor
9,392,953 B1 7/2016 Gharib
9,393,052 B2 7/2016 Berg et al.
9,398,962 B2 7/2016 Steinberg
9,402,726 B2 8/2016 Linderman et al.
9,408,615 B2 8/2016 Fitz et al.
9,408,642 B2 8/2016 Wong et al.
9,408,698 B2 8/2016 Miles et al.
9,414,940 B2 8/2016 Stein et al.
9,433,443 B2 9/2016 Montello et al.
9,439,659 B2 9/2016 Schoenefeld et al.
9,439,767 B2 9/2016 Bojarski et al.
9,439,781 B2 9/2016 Gibson
9,445,913 B2 9/2016 Donner et al.
9,452,022 B2 9/2016 McIntosh et al.
9,452,023 B2 9/2016 Boillot et al.
9,452,050 B2 9/2016 Miles et al.
9,452,064 B2 9/2016 Trautwein et al.
9,468,436 B2 10/2016 Groiso
9,468,502 B2 10/2016 Wiebe, III et al.
9,491,415 B2 11/2016 Deitz et al.
9,492,183 B2 11/2016 Wilkinson et al.
9,495,483 B2 11/2016 Steines et al.
9,495,509 B2 11/2016 Amiot et al.
9,498,260 B2 11/2016 Funk et al.
9,504,502 B2 11/2016 Kuiper et al.
9,510,771 B1 12/2016 Finley et al.
9,510,864 B2 12/2016 Devito
9,517,134 B2 12/2016 Lang
9,517,143 B2 12/2016 Prevost et al.
9,526,514 B2 12/2016 Kelley et al.
9,532,730 B2 1/2017 Wasielewski
9,539,031 B2 1/2017 Fauth
9,539,116 B2 1/2017 Claypool et al.
9,539,760 B2 1/2017 Stahl et al.
9,547,897 B2 1/2017 Parent et al.
9,549,782 B2 1/2017 Park et al.
9,554,411 B1 1/2017 Hall et al.
9,554,910 B2 1/2017 Vanasse et al.
9,561,115 B2 2/2017 Elahinia et al.
9,566,075 B2 2/2017 Carroll et al.
9,579,043 B2 2/2017 Chien et al.
9,585,597 B2 3/2017 McCaulley et al.
9,597,096 B2 3/2017 Aghazadeh
9,597,156 B2 3/2017 Amiot et al.
9,603,613 B2 3/2017 Schoenefeld et al.
9,603,623 B2 3/2017 Brooks et al.
9,603,711 B2 3/2017 Bojarski et al.
9,610,086 B2 4/2017 Park et al.
9,615,834 B2 4/2017 Agnihotri et al.
9,622,712 B2 4/2017 Munro et al.
9,629,723 B2 4/2017 Parisi et al.
9,636,181 B2 5/2017 Isaacs
9,642,633 B2 5/2017 Frey et al.
9,649,170 B2 5/2017 Park et al.
9,655,729 B2 5/2017 Parisi et al.
9,662,214 B2 5/2017 Li et al.
9,668,748 B2 6/2017 McKinnon et al.
9,668,873 B2 6/2017 Winslow et al.
9,675,471 B2 6/2017 Bojarski et al.
9,693,831 B2 7/2017 Mosnier et al.
9,715,563 B1 7/2017 Schroeder
9,757,072 B1 9/2017 Urbalejo
9,782,228 B2 10/2017 Mosnier et al.
9,788,966 B2 10/2017 Steinberg
9,827,109 B2 11/2017 Steinberg
9,848,922 B2 12/2017 Tohmeh et al.
9,968,408 B1 5/2018 Casey et al.
9,987,048 B2 6/2018 Mosnier et al.
9,993,177 B2 6/2018 Chien et al.
10,010,426 B2 7/2018 Kuiper et al.
10,045,824 B2 8/2018 Mosnier et al.
10,052,135 B2 8/2018 Berg et al.
10,064,743 B2 9/2018 Funk et al.
10,098,671 B2 10/2018 Augostino
10,188,480 B2 1/2019 Scholl et al.
10,201,320 B2 2/2019 Saget et al.
10,219,865 B2 3/2019 Jansen et al.
10,314,657 B2 6/2019 Mosnier et al.
10,413,365 B1 9/2019 Mosnier et al.
10,433,893 B1 10/2019 Scholl et al.
10,433,912 B1 10/2019 Mosnier et al.
10,433,913 B2 10/2019 Mosnier et al.
10,441,363 B1 10/2019 Mosnier et al.
10,456,211 B2 10/2019 McAfee
10,463,433 B2 11/2019 Turner et al.
11,185,369 B2 * 11/2021 Ryan ..................... A61B 34/10
12,004,814 B2 * 6/2024 Ryan ..................... G16H 50/50

(56) References Cited

U.S. PATENT DOCUMENTS

2002/0035321 A1 3/2002 Bucholz et al.
2002/0038118 A1 3/2002 Shoham
2002/0045812 A1 4/2002 Ben-Haim et al.
2002/0103432 A1 8/2002 Kawchuk
2003/0191383 A1 10/2003 Ben-Haim et al.
2003/0204189 A1 10/2003 Cragg
2004/0120781 A1 6/2004 Luca et al.
2004/0143243 A1 7/2004 Wahrburg
2004/0152972 A1 8/2004 Hunter
2004/0167637 A1 8/2004 Biscup
2004/0171924 A1 9/2004 Mire et al.
2004/0172020 A1 9/2004 Beaurain et al.
2004/0215190 A1 10/2004 Nguyen et al.
2004/0243148 A1 12/2004 Wasielewski
2004/0267279 A1 12/2004 Casutt et al.
2005/0149050 A1 7/2005 Stifter et al.
2005/0177239 A1 8/2005 Steinberg
2005/0182320 A1 8/2005 Stifter et al.
2005/0182454 A1 8/2005 Gharib et al.
2005/0203531 A1 9/2005 Lakin et al.
2005/0203532 A1 9/2005 Ferguson
2005/0262911 A1 12/2005 Dankowicz et al.
2006/0015018 A1 1/2006 Jutras et al.
2006/0015030 A1 1/2006 Poulin et al.
2006/0036259 A1 2/2006 Carl et al.
2006/0069324 A1 3/2006 Block et al.
2006/0074431 A1 4/2006 Sutton et al.
2006/0136058 A1 6/2006 Pietrzak
2006/0142657 A1 6/2006 Quaid et al.
2006/0285991 A1 12/2006 McKinley
2006/0287627 A1 12/2006 Johnson
2007/0021682 A1 1/2007 Gharib et al.
2007/0118243 A1 5/2007 Schroeder et al.
2007/0225731 A1 9/2007 Couture et al.
2008/0058945 A1 3/2008 Hajaj et al.
2008/0079546 A1 4/2008 Sensomatic
2008/0108991 A1 5/2008 von Jako
2008/0177203 A1 7/2008 von Jako
2008/0245972 A1 10/2008 Drapeau
2008/0255575 A1 10/2008 Justis et al.
2008/0281332 A1 11/2008 Taylor
2009/0024164 A1 1/2009 Neubardt
2009/0076615 A1 3/2009 Duggal et al.
2009/0157083 A1 6/2009 Park et al.
2009/0194206 A1 8/2009 Jeon et al.
2009/0204159 A1 8/2009 Justis et al.
2009/0248080 A1 10/2009 Wilcox et al.
2009/0249851 A1 10/2009 Isaacs
2009/0254326 A1 10/2009 Isaacs
2010/0042157 A1 2/2010 Trieu
2010/0100011 A1 4/2010 Roche
2010/0191071 A1 7/2010 Anderson et al.
2010/0191088 A1* 7/2010 Anderson .............. A61B 34/20
606/300
2010/0217270 A1 8/2010 Polinski et al.
2010/0217336 A1 8/2010 Crawford et al.
2011/0004309 A9 1/2011 Holm
2011/0071802 A1 3/2011 Bojarski et al.
2011/0118740 A1 5/2011 Rabiner et al.
2011/0172566 A1 7/2011 Kawchuk
2011/0214279 A1 9/2011 Park et al.
2011/0224796 A1 9/2011 Weiland et al.
2011/0257653 A1 10/2011 Hughes et al.
2011/0257657 A1 10/2011 Turner et al.
2011/0295159 A1 12/2011 Shachar et al.
2011/0306873 A1 12/2011 Shenai et al.
2012/0022357 A1 1/2012 Chang et al.
2012/0027261 A1 2/2012 Frank et al.
2012/0035611 A1 2/2012 Kave
2012/0123301 A1 5/2012 Connor et al.
2012/0143090 A1 6/2012 Hay et al.
2012/0150243 A9 6/2012 Crawford et al.
2012/0172884 A1 7/2012 Zheng et al.
2012/0203289 A1 8/2012 Beerens et al.
2013/0079678 A1 3/2013 Stein et al.
2013/0079679 A1 3/2013 Roche et al.
2013/0079790 A1 3/2013 Stein et al.
2013/0131486 A1 5/2013 Copf et al.
2013/0211531 A1 8/2013 Steines et al.
2013/0245631 A1 9/2013 Bettenga
2013/0253599 A1 9/2013 Gorek et al.
2013/0268007 A1 10/2013 Rezach et al.
2013/0303883 A1 11/2013 Zehavi et al.
2013/0345718 A1 12/2013 Crawford et al.
2014/0058407 A1 2/2014 Tsekos et al.
2014/0081659 A1* 3/2014 Nawana ................ G16H 10/20
705/3
2014/0100579 A1 4/2014 Kelman et al.
2014/0135658 A1 5/2014 Hladio et al.
2014/0180415 A1 6/2014 Koss
2014/0194889 A1 7/2014 Chang et al.
2014/0208578 A1* 7/2014 Linderman .......... A61B 17/158
623/18.11
2014/0228670 A1 8/2014 Justis et al.
2014/0228860 A1 8/2014 Steines et al.
2014/0244220 A1 8/2014 McKinnon et al.
2014/0257402 A1 9/2014 Barsoum
2014/0272881 A1 9/2014 Barsoum
2014/0277149 A1 9/2014 Rooney et al.
2014/0296860 A1 10/2014 Stein et al.
2014/0303672 A1 10/2014 Tran et al.
2014/0316468 A1 10/2014 Keiser et al.
2015/0057756 A1 2/2015 Lang et al.
2015/0066145 A1 3/2015 Rogers et al.
2015/0080901 A1 3/2015 Stein
2015/0081029 A1 3/2015 Bojarski et al.
2015/0088030 A1 3/2015 Taylor
2015/0100066 A1 4/2015 Kostrzewski et al.
2015/0100091 A1 4/2015 Tohmeh et al.
2015/0105782 A1 4/2015 D'Lima et al.
2015/0127055 A1 5/2015 Dvorak et al.
2015/0150646 A1 6/2015 Pryor et al.
2015/0164657 A1 6/2015 Miles et al.
2015/0182292 A1 7/2015 Hladio et al.
2015/0223900 A1 8/2015 Wiebe et al.
2015/0245844 A1 9/2015 Kennedy et al.
2015/0250597 A1 9/2015 Lang et al.
2015/0265291 A1 9/2015 Wilkinson
2015/0305878 A1 10/2015 O'Neil et al.
2015/0305891 A1 10/2015 Bergin et al.
2015/0313723 A1 11/2015 Jansen et al.
2015/0328004 A1 11/2015 Mahfouz
2015/0366630 A1 12/2015 Gorek et al.
2016/0000571 A1 1/2016 Mahfouz
2016/0007983 A1 1/2016 Frey et al.
2016/0015465 A1 1/2016 Steines et al.
2016/0022176 A1 1/2016 Le Huec et al.
2016/0022370 A1 1/2016 Pavlovskaia et al.
2016/0038161 A1 2/2016 Gibson
2016/0038238 A1 2/2016 Kostrzewski et al.
2016/0038242 A1 2/2016 Lacono et al.
2016/0038293 A1 2/2016 Slamin et al.
2016/0038307 A1 2/2016 Bettenga
2016/0045230 A1 2/2016 Lowery et al.
2016/0045326 A1 2/2016 Hansen et al.
2016/0058320 A1 3/2016 Chien et al.
2016/0058523 A1 3/2016 Chien et al.
2016/0074052 A1 3/2016 Keppler et al.
2016/0074202 A1 3/2016 Reed et al.
2016/0081754 A1 3/2016 Kostrzewski et al.
2016/0095710 A1 4/2016 Juszczyk et al.
2016/0100907 A1 4/2016 Gomes
2016/0106483 A1 4/2016 Mayer et al.
2016/0128847 A1 5/2016 Kurtaliaj et al.
2016/0143744 A1 5/2016 Bojarski et al.
2016/0157751 A1 6/2016 Mahfouz
2016/0199101 A1 7/2016 Sharifi-Mehr et al.
2016/0210374 A1 7/2016 Mosnier et al.
2016/0228192 A1 8/2016 Jansen et al.
2016/0235480 A1 8/2016 Scholl et al.
2016/0235493 A1 8/2016 LeBoeuf et al.
2016/0242819 A1 8/2016 Simpson et al.
2016/0242857 A1 8/2016 Scholl
2016/0242934 A1 8/2016 van der Walt et al.

(56) References Cited

U.S. PATENT DOCUMENTS

2016/0256279 A1 9/2016 Sanders et al.
2016/0256285 A1 9/2016 Jansen
2016/0262800 A1 9/2016 Scholl et al.
2016/0262895 A1 9/2016 Shea et al.
2016/0270802 A1 9/2016 Fang et al.
2016/0270931 A1 9/2016 Trieu
2016/0274571 A1 9/2016 Lavallee et al.
2016/0283676 A1 9/2016 Lyon et al.
2016/0287395 A1 10/2016 Khalili et al.
2016/0296285 A1 10/2016 Chaoui et al.
2016/0310221 A1 10/2016 Bar et al.
2016/0331417 A1 11/2016 Trautwein et al.
2016/0354009 A1 12/2016 Schroeder
2016/0354161 A1 12/2016 Deitz
2016/0360997 A1 12/2016 Yadav et al.
2017/0000568 A1 1/2017 O'Neil et al.
2017/0007145 A1 1/2017 Gharib et al.
2017/0007328 A1 1/2017 Cattin et al.
2017/0007408 A1 1/2017 Fitz et al.
2017/0027590 A1 2/2017 Amiot et al.
2017/0027617 A1 2/2017 Strnad
2017/0035580 A1 2/2017 Murphy
2017/0056179 A1 3/2017 Lorio
2017/0056196 A1 3/2017 Kuiper et al.
2017/0071503 A1 3/2017 Wasielewski
2017/0119472 A1 5/2017 Herrmann et al.
2017/0132389 A1 5/2017 McCaulley et al.
2017/0135706 A1 5/2017 Frey et al.
2017/0135707 A9 5/2017 Frey et al.
2017/0135728 A1 5/2017 Williams
2017/0135770 A1 5/2017 Scholl et al.
2017/0143426 A1 5/2017 Isaacs et al.
2017/0143494 A1 5/2017 Mahfouz
2017/0143502 A1 5/2017 Yadin et al.
2017/0156798 A1 6/2017 Wasielewski
2017/0189121 A1 7/2017 Frasier et al.
2017/0231709 A1 8/2017 Gupta et al.
2017/0245937 A1 8/2017 Mosnier
2017/0252107 A1 9/2017 Turner et al.
2017/0273718 A1 9/2017 Metzger et al.
2017/0323037 A1 11/2017 Schroeder
2017/0360493 A1 12/2017 Zucker et al.
2018/0132942 A1 5/2018 Mosnier et al.
2018/0178148 A1 6/2018 Mazor et al.
2018/0256067 A1 9/2018 Chien et al.
2018/0289396 A1 10/2018 McGahan et al.
2018/0295584 A1 10/2018 Gliner et al.
2018/0301213 A1 10/2018 Zehavi et al.
2018/0310993 A1 11/2018 Hobeika et al.
2018/0349519 A1 12/2018 Schroeder
2019/0015136 A1 1/2019 Kraemer
2019/0046268 A1 2/2019 Mosnier et al.
2019/0046269 A1 2/2019 Hedblom et al.
2019/0046287 A1 2/2019 Fallin et al.
2019/0059951 A1 2/2019 Barrus
2019/0060086 A1 2/2019 Krause et al.
2019/0069956 A1 3/2019 Ryan et al.
2019/0083144 A1 3/2019 Sharifi-Mehr et al.
2019/0103190 A1 4/2019 Schmidt et al.
2019/0110819 A1 4/2019 Triplett et al.
2019/0117278 A1 4/2019 Chin
2019/0122364 A1 4/2019 Zhang et al.
2019/0142599 A1 5/2019 Thibodeau
2019/0167314 A1 6/2019 Mosnier et al.
2019/0201013 A1 7/2019 Siccardi et al.
2019/0201155 A1 7/2019 Gupta et al.
2019/0209212 A1 7/2019 Scholl et al.
2019/0223916 A1 7/2019 Barrus et al.
2019/0231435 A1 8/2019 Zucker et al.
2019/0231443 A1 8/2019 McGinley et al.
2019/0231557 A1 8/2019 Sutterlin, III et al.
2019/0239935 A1 8/2019 Willis et al.
2019/0247100 A1 8/2019 Mundis, Jr. et al.
2019/0254769 A1 8/2019 Scholl et al.
2019/0262015 A1 8/2019 Siccardi et al.
2019/0269463 A1 9/2019 Mosnier et al.
2019/0343587 A1 11/2019 Mosnier et al.
2019/0362028 A1 11/2019 Mosnier et al.
2019/0380782 A1 12/2019 McAfee et al.
2020/0060768 A1 2/2020 Mosnier et al.
2020/0121394 A1 4/2020 Mosnier et al.

FOREIGN PATENT DOCUMENTS

JP 2011528917 A 12/2011
JP 2016536051 A 11/2016
WO 9855038 A1 12/1998
WO 00/53077 A2 9/2000
WO 04/017836 A2 3/2004
WO 04/030559 A1 4/2004
WO 04/089224 A2 10/2004
WO 04/111948 A2 12/2004
WO 05/074368 A2 8/2005
WO 06/075331 A2 7/2006
WO 06/084193 A2 8/2006
WO 07/035925 A2 3/2007
WO 07/038290 A2 4/2007
WO 08/002588 A2 1/2008
WO 08/079546 A2 7/2008
WO 08/124079 A1 10/2008
WO 09/119181 A1 10/2009
WO 09/124245 A1 10/2009
WO 10/044880 A1 4/2010
WO 10/064234 A2 6/2010
WO 10/121147 A1 10/2010
WO 10/147972 A1 12/2010
WO 11/021192 A1 2/2011
WO 12/012863 A1 2/2012
WO 12/113030 A1 8/2012
WO 12/131660 A1 10/2012
WO 13/003435 A1 1/2013
WO WO-2013020026 A1 * 2/2013 ......... A61F 2/30942
WO 14/191790 A1 12/2014
WO 15/040552 A1 3/2015
WO 15/054543 A1 4/2015
WO 15/056131 A1 4/2015
WO 15/079011 A1 6/2015
WO 15/089118 A1 6/2015
WO 15/185219 A1 12/2015
WO 15/195843 A2 12/2015
WO 2015200720 A2 12/2015
WO 16/012726 A1 1/2016
WO 16/019424 A1 2/2016
WO 16/019425 A1 2/2016
WO 16/019426 A1 2/2016
WO 16/026053 A1 2/2016
WO 16/032875 A1 3/2016
WO 16/044352 A1 3/2016
WO 16/048800 A1 3/2016
WO 16/088130 A1 6/2016
WO 16/094826 A1 6/2016
WO 16/102026 A1 6/2016
WO 16/137347 A1 9/2016
WO 16/148675 A1 9/2016
WO 16/165030 A1 10/2016
WO 17/001851 A1 1/2017
WO 17/039596 A1 3/2017
WO 17/064719 A1 4/2017
WO 17/066518 A1 4/2017
WO 17/077356 A1 5/2017
WO 17/079655 A2 5/2017
WO 17/127838 A1 7/2017
WO 17/151949 A1 9/2017
WO 17/221257 A1 12/2017
WO 18/045086 A1 3/2018
WO 18/055494 A1 3/2018
WO 18/055518 A1 3/2018
WO 18/078636 A1 5/2018
WO 18/087758 A1 5/2018
WO 18/131044 A1 7/2018
WO 18/131045 A1 7/2018
WO 18/183314 A1 10/2018
WO 18/185755 A1 10/2018
WO 18/193316 A2 10/2018

(56) References Cited

FOREIGN PATENT DOCUMENTS

| | | | |
|---|---|---|---|
| WO | 18/193317 | A1 | 10/2018 |
| WO | 18/203100 | A1 | 11/2018 |
| WO | 18/203101 | A1 | 11/2018 |
| WO | 2019014452 | A1 | 1/2019 |
| WO | 2019036039 | A2 | 2/2019 |
| WO | 2019043426 | A1 | 3/2019 |
| WO | 2019068085 | A1 | 4/2019 |
| WO | 2019070729 | A1 | 4/2019 |
| WO | 2019118844 | A1 | 6/2019 |
| WO | 2019140240 | A1 | 7/2019 |

OTHER PUBLICATIONS

Aubin et al. "Preoperative Planning Simulator for Spinal Deformity Surgeries", Spine 2008, 33(20):2143-2152.
Barton et al., Mar./Apr. 2016, Early experience and initial outcomes with patient-specific spine rods for adult spinal deformity, Trending in Orthopedics, 39(2):79-86.
Fiere et al., Jul. 2016, 40. Preoperative planning and patient-specific rods for surgical treatment of thoracolumbar sagittal imbalance, in Surgery of the Spine and Spinal Cord. A Neurosurgical Approach, Van de Kalft ed., Springer InternationalPublishing, Switzerland, pp. 645-662.
Foroozandeh et al., Summer 2012, 3D reconstruction using cubic Bezier spline curves and active contours (case study), Iranian Journal of Medical Physics, 9(3):169-176.
Galbusera et al., Feb. 2019, Artificial intelligence and machine learning in spine research, JOR Spine, 2:E1044, 20 pp.
Grove, 2011, Heterogeneous model564ing of medical image data using B-spline functions, doctoral dissertation, Department of Computer Science and Engineering, University of South Florida, 212 pp.
Lazarus, Jun. 21, 2013, An introduction to splines, 29 pp.
Li et al., 2009, Modeling and measurement of 3D deformation of scoliotic spine using 2D x-ray images, Lecture Notes in Computer Science, 8 pp.
Lin, Sep. 17-21, 2003, The simplified spine modeling by 3-D Bezier curve based on the orthogonal spinal radiographic images, Proceedings of the 25th Annual International Conference of the IEEE EMBS, Cancun, Mexico, pp. 944-946.
Pasha et al., 2018, Data-driven classification of the 3D spinal curve in adolescent idiopathic scoliosis with an applications in surgical outcome prediction, Scientific Reports, 8:16296, 10 pp.
Poredos et al., 2015, Determination of the human spine curve based on laser triangulation, BMC Medical Imaging 15(2):1-11.
Prautzsch et al., Mar. 26, 2001, Bezier-and B-spline techniques, 58 pp.
Ratnakar et al. 2011, Predicting thoracic spinal postures in finite element model with Bezier technique, Ircobe Conference 2011, IRC-11-57, 4 pp.
Reinshagen et al. "A novel minimally invasive technique for lum564bar decompression, realignment, and navigated interbody fusion", J Clin Neurosci. 2015, 22(9):1484-1490; XP055503028.
Rickert et al., "Posterior lumbar interbody fusion implants", Orthopaede, Springer Verlag, Berlin, DE vol. 44, No. 2 dated Jan. 28, 2015 pp. 162-169.
Solla et al., Mar. 2019, Patient-specific rods for surgical correction of sagittal imbalance in adults: Technical aspects and preliminary results, Clin Spine Surg, 32(2), 7 pp.
Spontech Medical AG Vertaplan—die Software fur Wirbelsaulenchirurgen, Aug. 29, 2013 Retrieved from the Internet: URL: https://www.youtube.com/watch?v=q0qhW1T1cp8 in 1 page.
International Search Report and Written Opinion in PCT Application PCT/IB2018/000551, dated Dec. 12, 2018 in 9 pages.
International Search Report and Written Opinon in PCT Application PCT/IB2018/000557 dated Oct. 24, 2018 in 12 pages.
International Search Report in PCT Application PCT/IB2014/064586, dated Dec. 23, 2014, in 2 pages.
International Search Report in PCT Application PCT/US2016/060676, dated Nov. 5, 2017 in 7 pages.
International Search Report in PCT Application PCT/IB2018/000557 dated Aug. 24, 2018 in 12 pages.
Office Action in Japanese Application No. 2019-552121 dated Mar. 1, 2022.
International Search Report in Application No. PCT/IB2018/000551, dated Dec. 12, 2018.
International Search Report in Application No. PCT/IB2018/000557, dated Sep. 4, 2018.
Office Action in Japanese Patent Application No. 2019-551980 dated Mar. 29, 2022.
Office Action in Japanese Application No. 2019-552121 dated Oct. 7, 2022.
European Search Report in Application No. 22189699.6 dated Oct. 28, 2022.
Rickert, M. et al., "Posterior lumbar interbody fusion implants", Othopaede Springer Verlag, Berlin, DE, vol. 44, No. 2, Jan. 28, 2015, pp. 162-169, XP035457088.
Reinshagen, Clemens et al., "A novel minimally invasive technique for lumbar decompression, realignment, and navigated interbody fusion—ScienceDirect", Journal of Clinical Neuroscience, Sep. 1, 2015, pp. 1484-1490, XP055503028.

* cited by examiner

FIG. 2

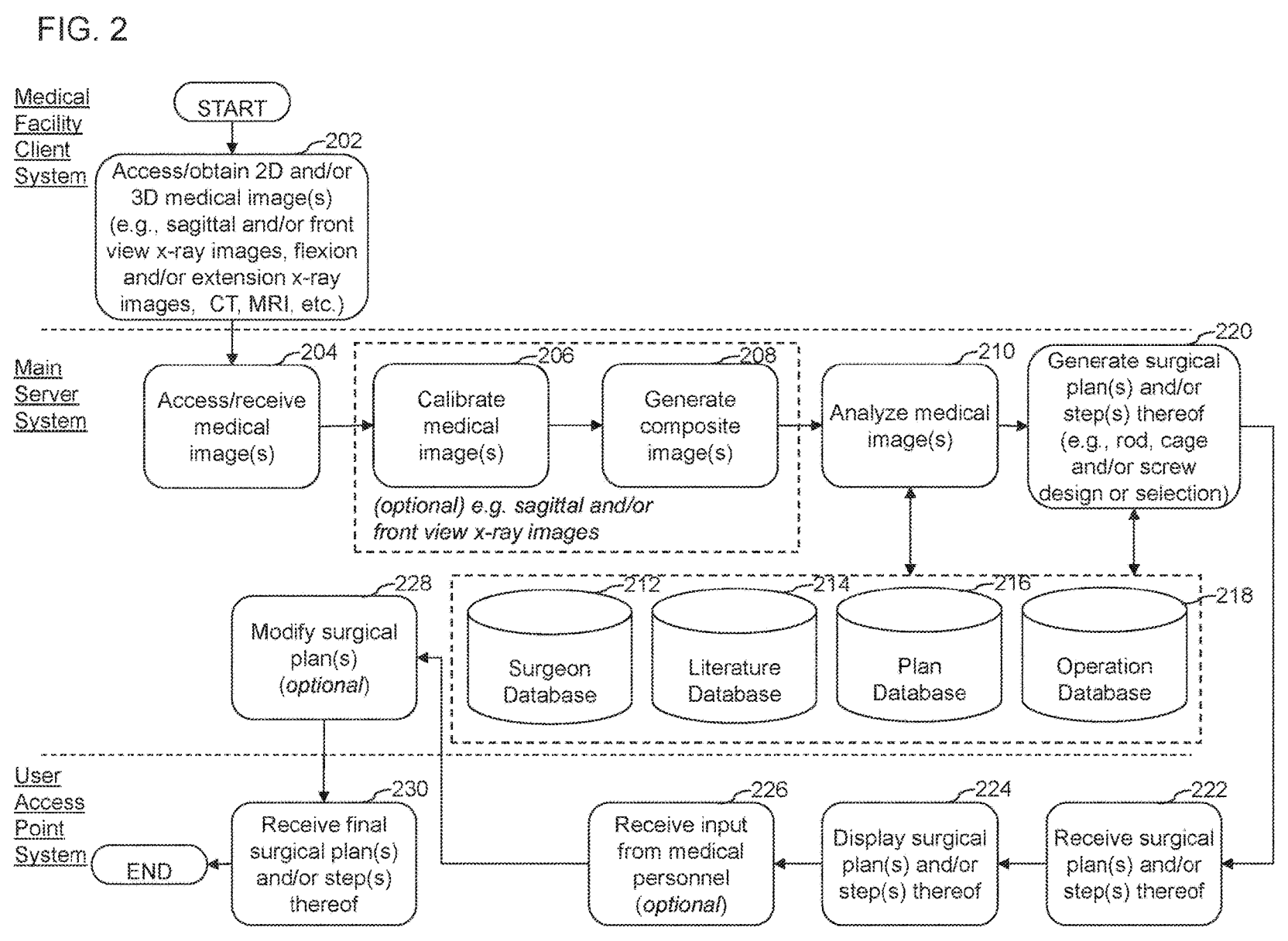

Medical Facility Client System

START

202 Access/obtain 2D and/or 3D medical image(s) (e.g., sagittal and/or front view x-ray images, flexion and/or extension x-ray images, CT, MRI, etc.)

Main Server System

204 Access/receive medical image(s)

206 Calibrate medical image(s)

208 Generate composite image(s)

*(optional) e.g. sagittal and/or front view x-ray images*

210 Analyze medical image(s)

220 Generate surgical plan(s) and/or step(s) thereof (e.g., rod, cage and/or screw design or selection)

212 Surgeon Database

214 Literature Database

216 Plan Database

218 Operation Database

228 Modify surgical plan(s) (*optional*)

User Access Point System

222 Receive surgical plan(s) and/or step(s) thereof

224 Display surgical plan(s) and/or step(s) thereof

226 Receive input from medical personnel (*optional*)

230 Receive final surgical plan(s) and/or step(s) thereof

END

FIG. 3

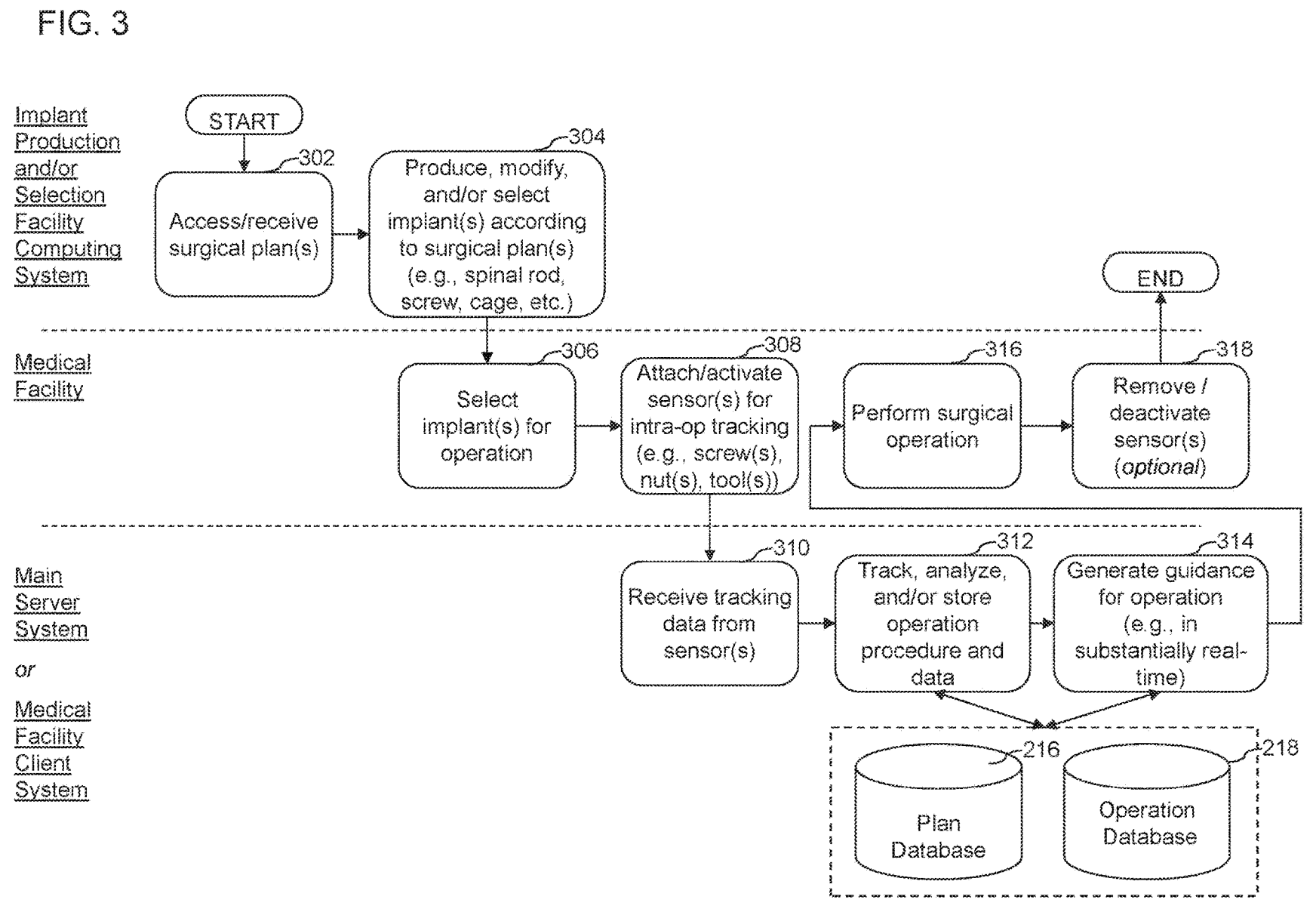

Implant Production and/or Selection Facility Computing System

START

302 Access/receive surgical plan(s)

304 Produce, modify, and/or select implant(s) according to surgical plan(s) (e.g., spinal rod, screw, cage, etc.)

Medical Facility

306 Select implant(s) for operation

308 Attach/activate sensor(s) for intra-op tracking (e.g., screw(s), nut(s), tool(s))

316 Perform surgical operation

318 Remove / deactivate sensor(s) (*optional*)

END

Main Server System or Medical Facility Client System

310 Receive tracking data from sensor(s)

312 Track, analyze, and/or store operation procedure and data

314 Generate guidance for operation (e.g., in substantially real-time)

218

216 Plan Database

Operation Database

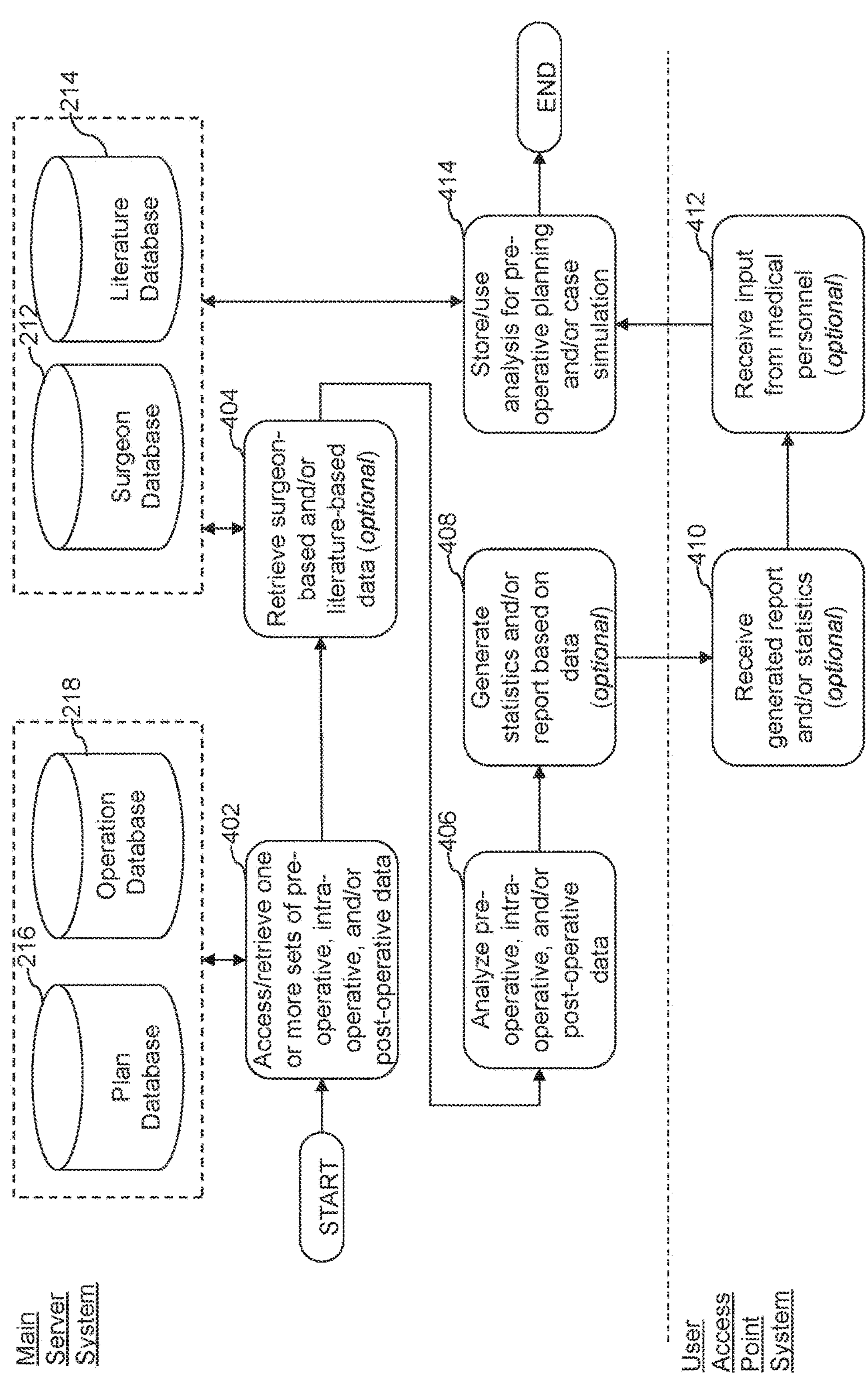
FIG. 4
Main Server System
User Access Point System
Plan Database
216
Operation Database
218
Surgeon Database
212
Literature Database
214
START
Access/retrieve one or more sets of pre-operative, intra-operative, and/or post-operative data
402
Retrieve surgeon-based and/or literature-based data (optional)
404
Analyze pre-operative, intra-operative, and/or post-operative data
406
Generate statistics and/or report based on data (optional)
408
Receive generated report and/or statistics (optional)
410
Receive input from medical personnel (optional)
412
Store/use analysis for pre-operative planning and/or case simulation
414
END

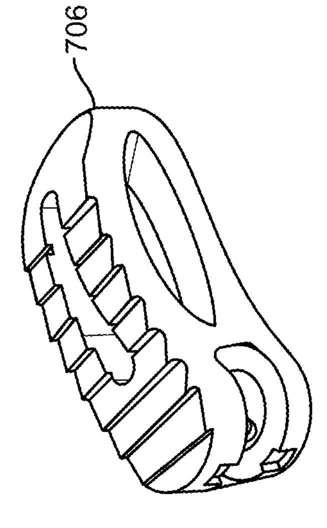
FIG. 7C
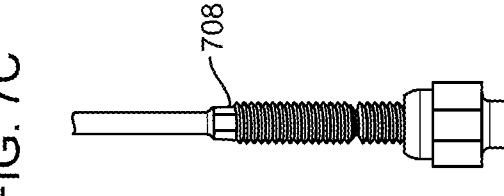
FIG. 7D
702
FIG. 7A
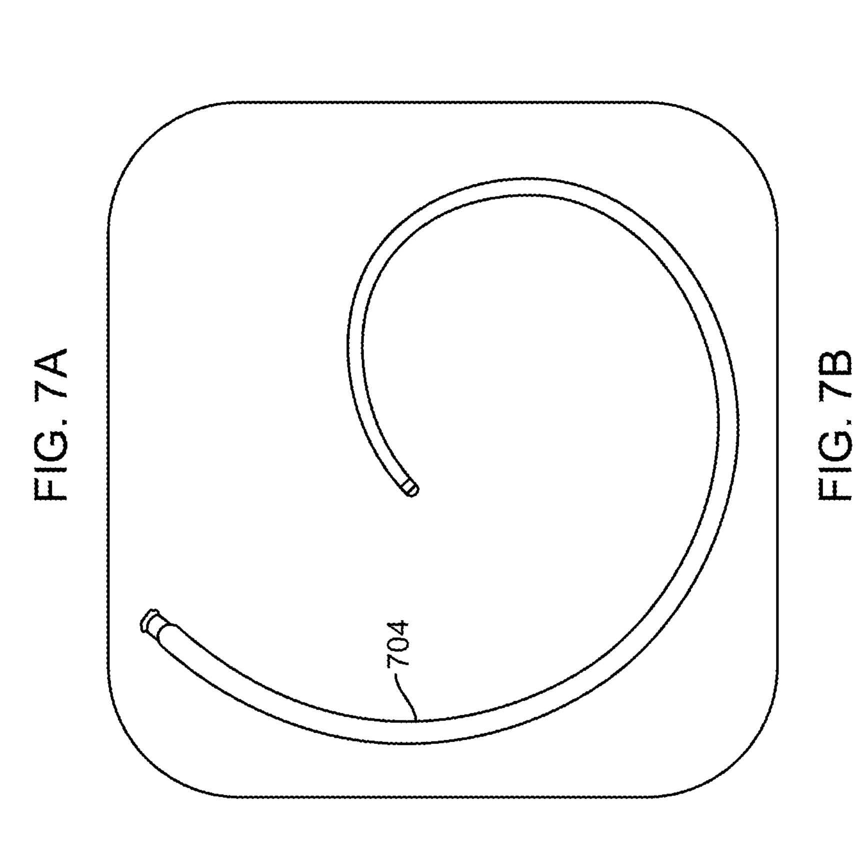
FIG. 7B

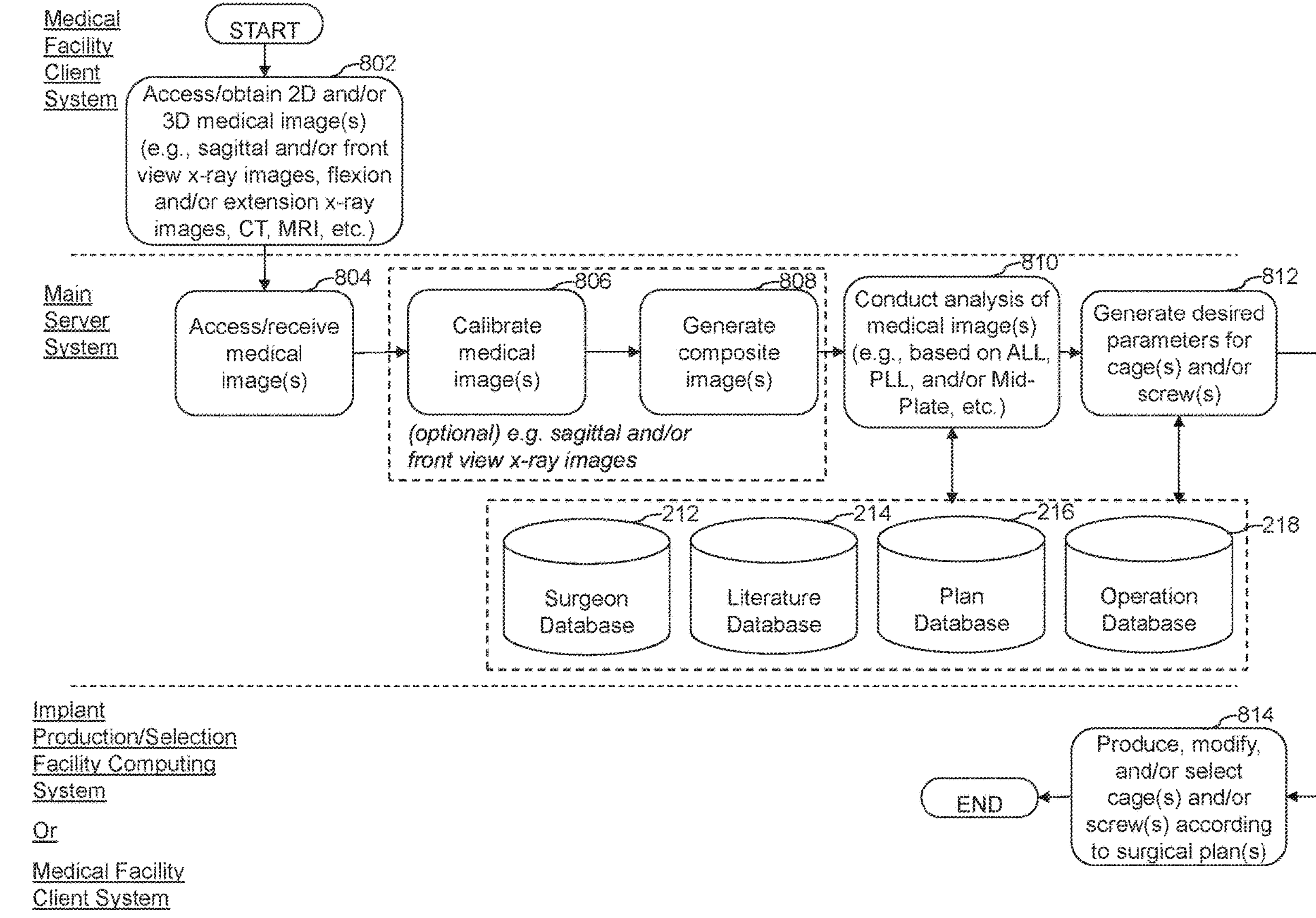
FIG. 8 – Cage/Screw Planning
Medical Facility Client System
START
802
Access/obtain 2D and/or 3D medical image(s) (e.g., sagittal and/or front view x-ray images, flexion and/or extension x-ray images, CT, MRI, etc.)
Main Server System
804
Access/receive medical image(s)
806
Calibrate medical image(s)
808
Generate composite image(s)
(optional) e.g. sagittal and/or front view x-ray images
810
Conduct analysis of medical image(s) (e.g., based on ALL, PLL, and/or Mid-Plate, etc.)
812
Generate desired parameters for cage(s) and/or screw(s)
212
Surgeon Database
214
Literature Database
216
Plan Database
218
Operation Database
Implant Production/Selection Facility Computing System
Or
Medical Facility Client System
814
Produce, modify, and/or select cage(s) and/or screw(s) according to surgical plan(s)
END FIG. 9B
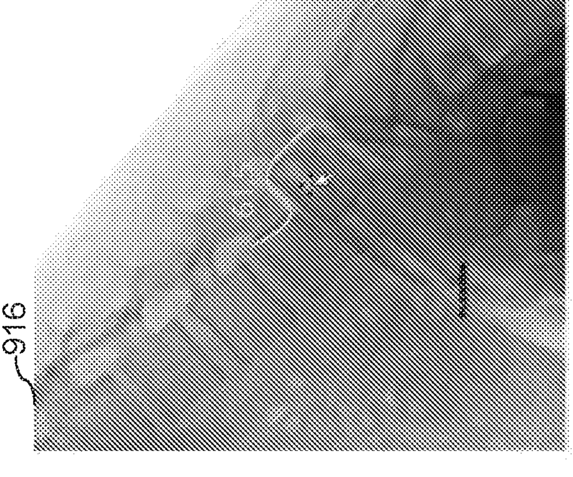
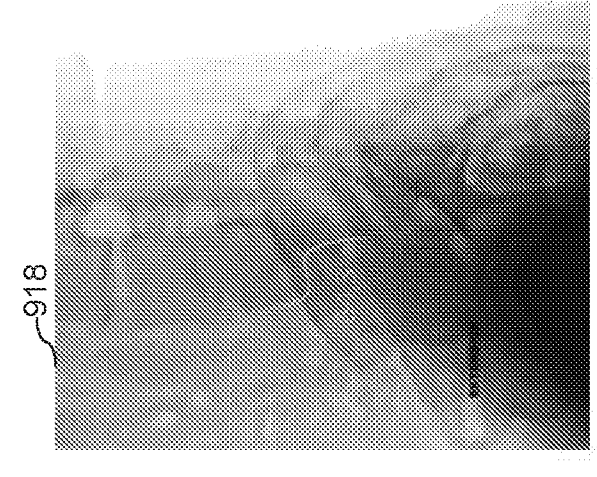
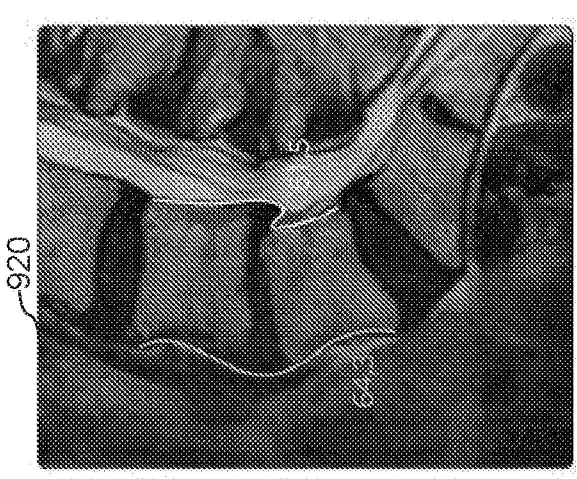

FIG. 9C
#1 Drawing of PC and AC
922
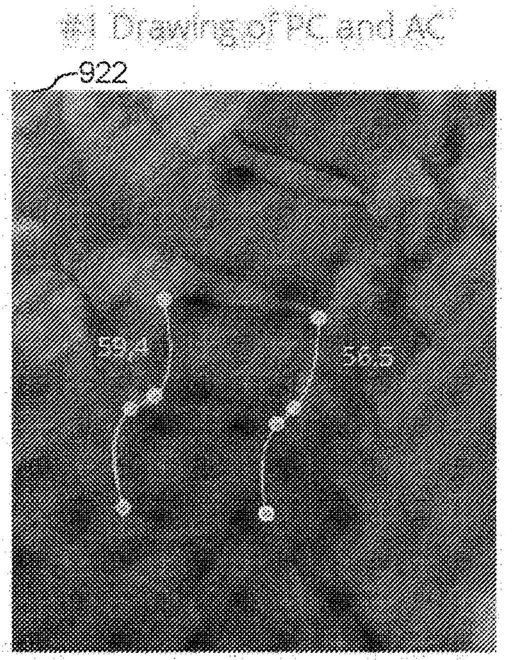
PC curve is going through the 4 posterior vertebra corner and AC curve is going through the 4 anterior vertebra corner
#2 Increase Hpost of the cage
Until PC = PLL
924
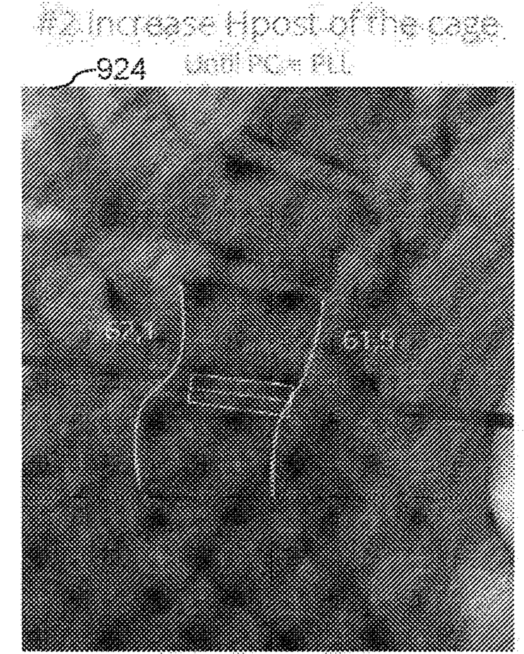
PC = PLL = 61,5
AC = 62,1 and ALL = 64,3
#3 Increase lordosis
Keeping AC ≤ ALL
926
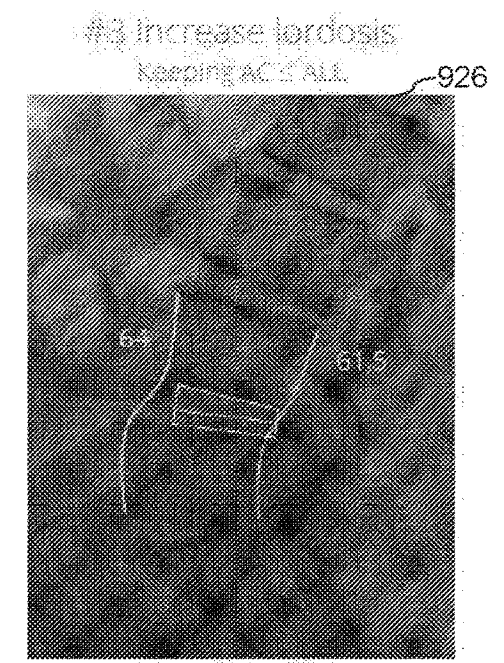
PC = PLL = 61,5
AC = 64 and ALL = 64,3
Cage dimensions:
Hant = 10mm
Hpost = 7mm
Lordosis = 6°

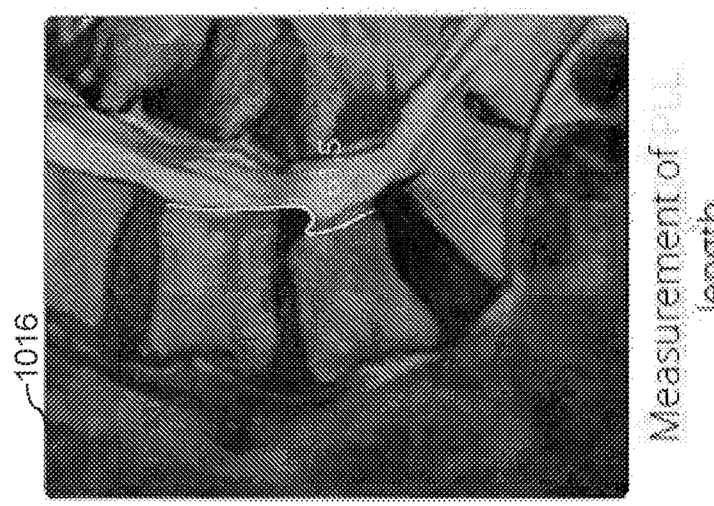
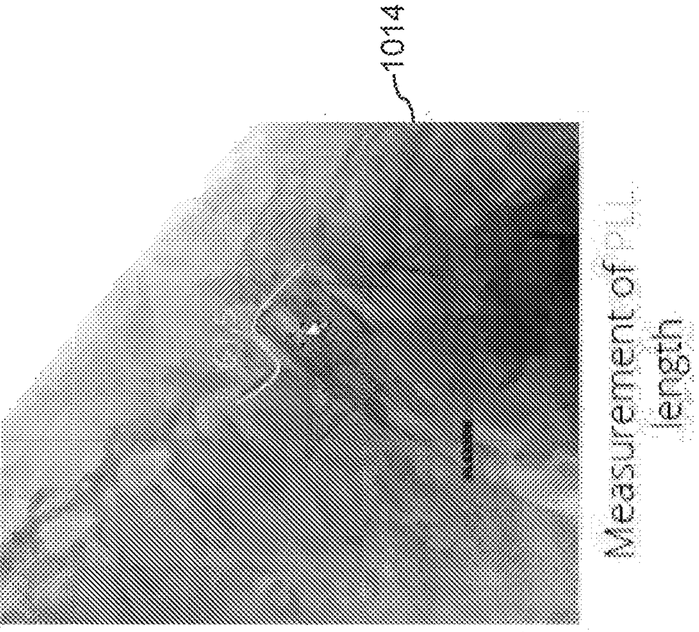
FIG. 10B

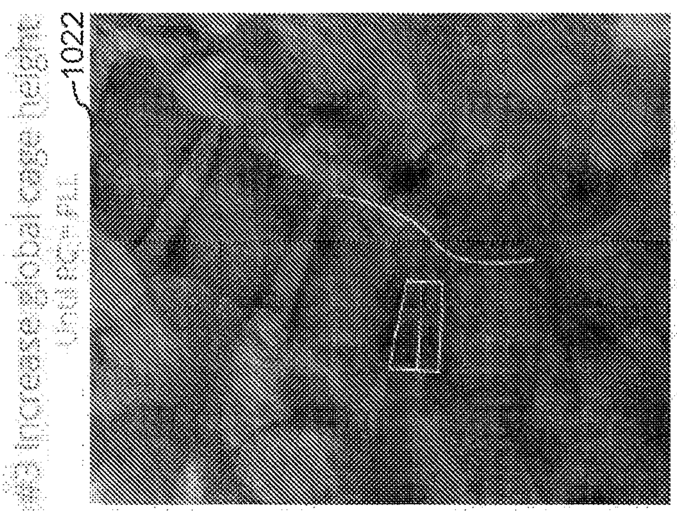
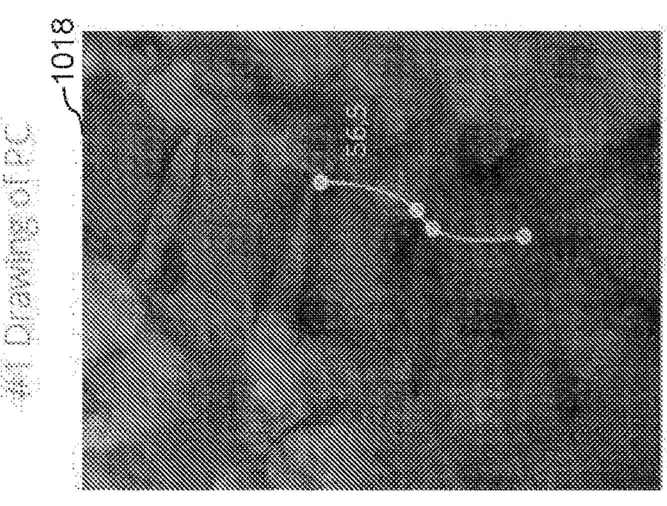
FIG. 10C

Figure 12B:
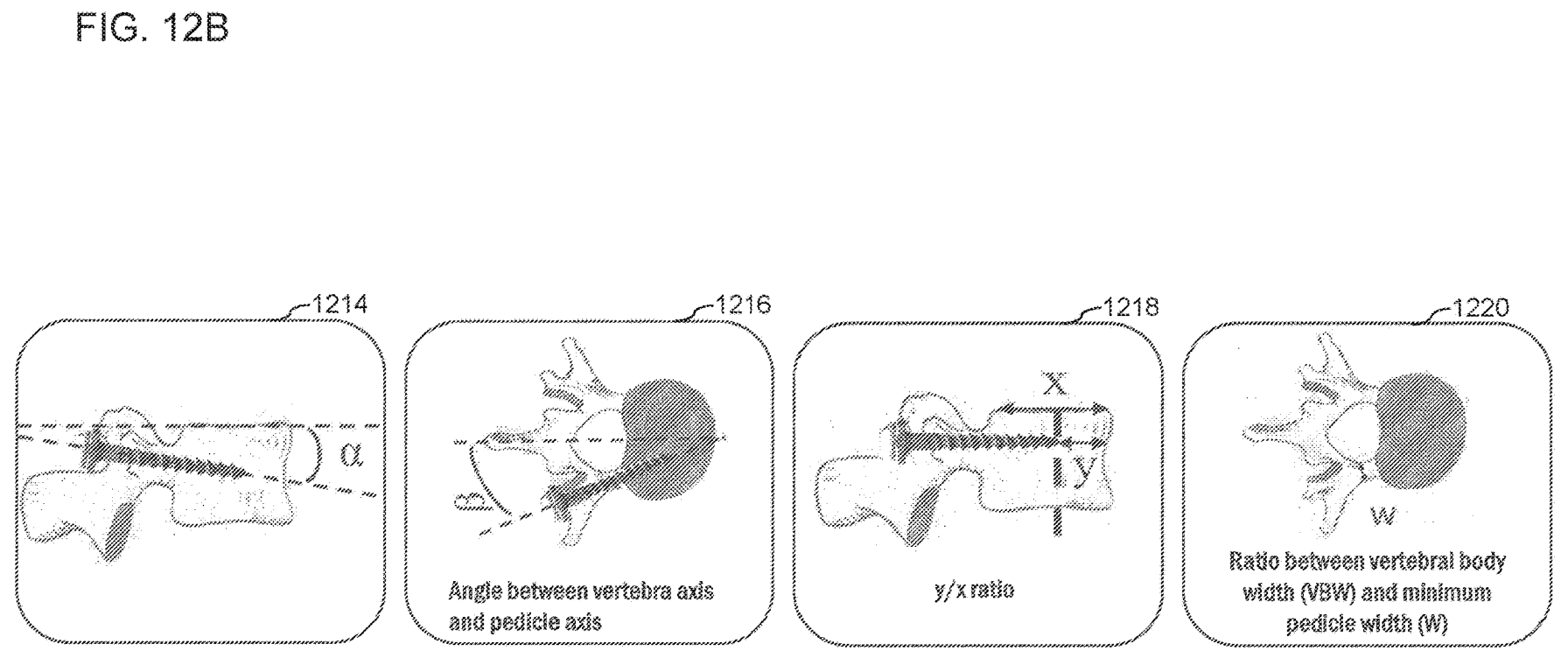

Angle between vertebra axis and pedicle axis

1218 x y y/x ratio

1220

W

Ratio between vertebral body width (VBW) and minimum pedicle width (W)

1308
1302
1306

1308
1302
1306

1308
1302
1306

1302
1308
1306

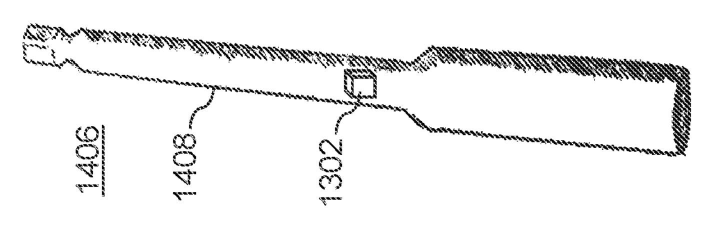
FIG. 14C
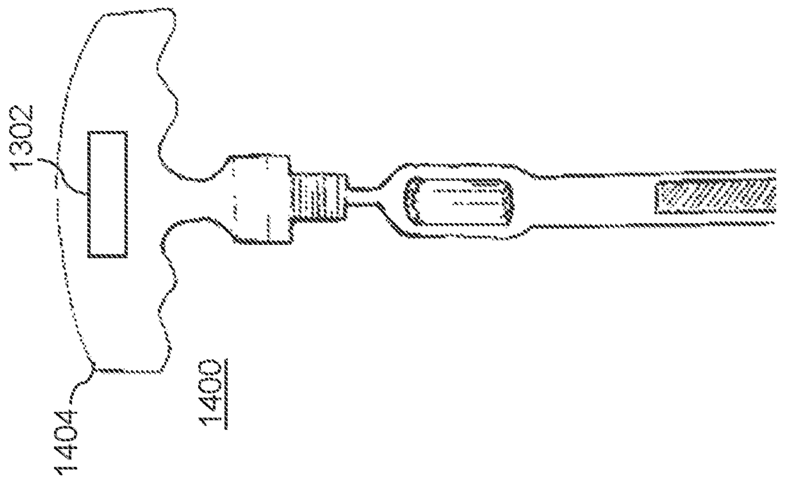
FIG. 14B
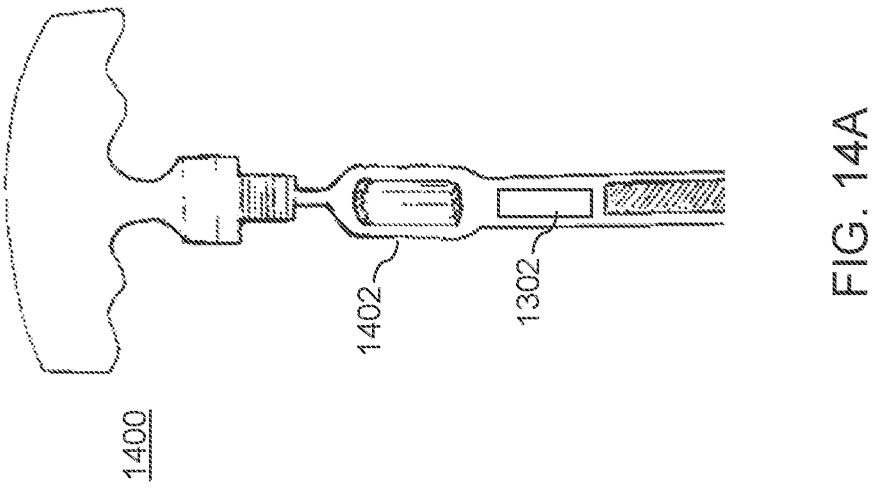
FIG. 14A

Figure 15:
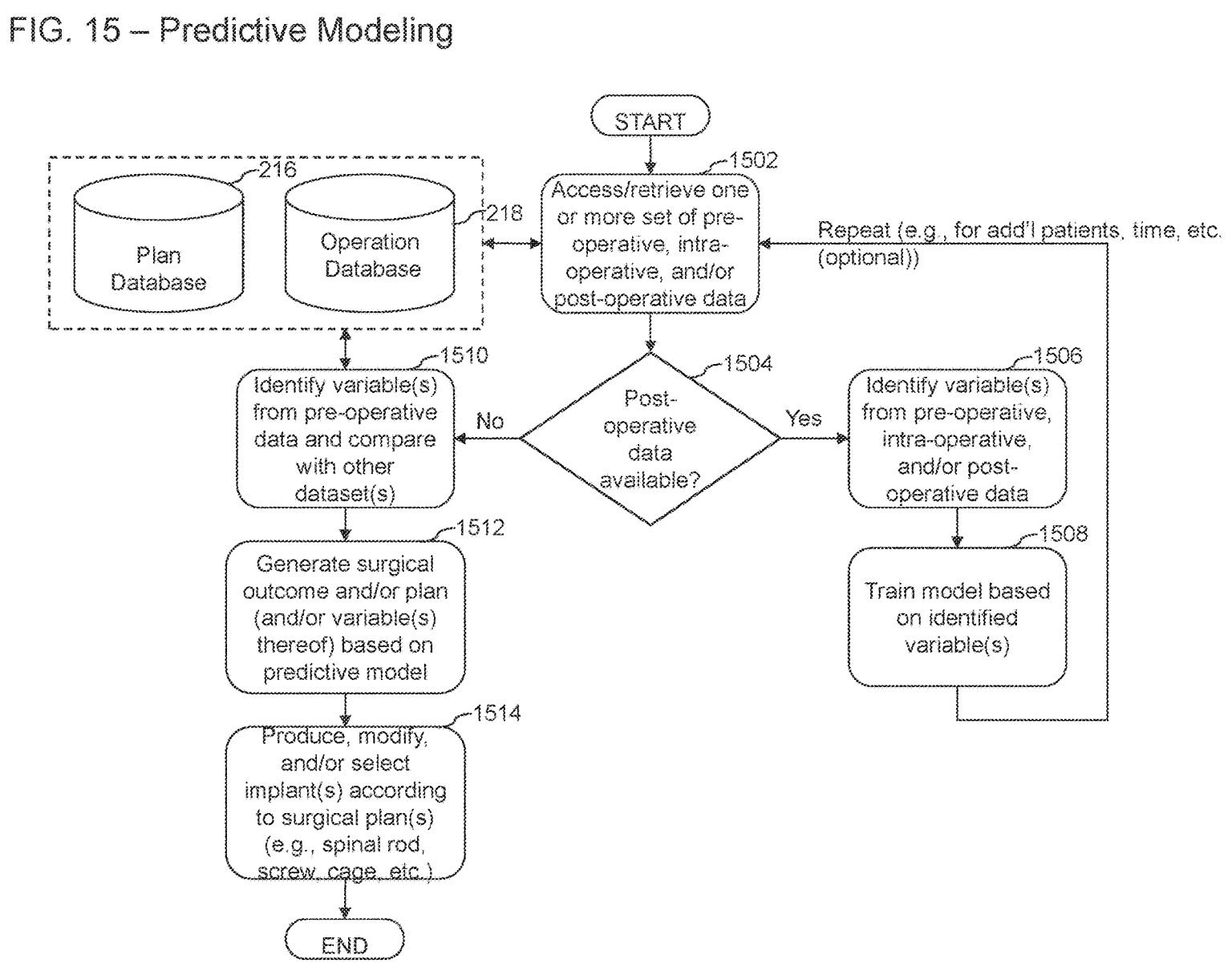

FIG. 15 – Predictive Modeling

START

1502 Access/retrieve one or more set of pre-operative, intra-operative, and/or post-operative data Repeat (e.g., for add'l patients, time, etc. (optional))

216 Plan Database

218 Operation Database

1504 Post-operative data available?

Yes

No

1506 Identify variable(s) from pre-operative, intra-operative, and/or post-operative data 1508 Train model based on identified variable(s)

1510 Identify variable(s) from pre-operative data and compare with other dataset(s)

1512 Generate surgical outcome and/or plan (and/or variable(s) thereof) based on predictive model 1514 Produce, modify, and/or select implant(s) according to surgical plan(s) (e.g., spinal rod, screw, cage, etc.)

END

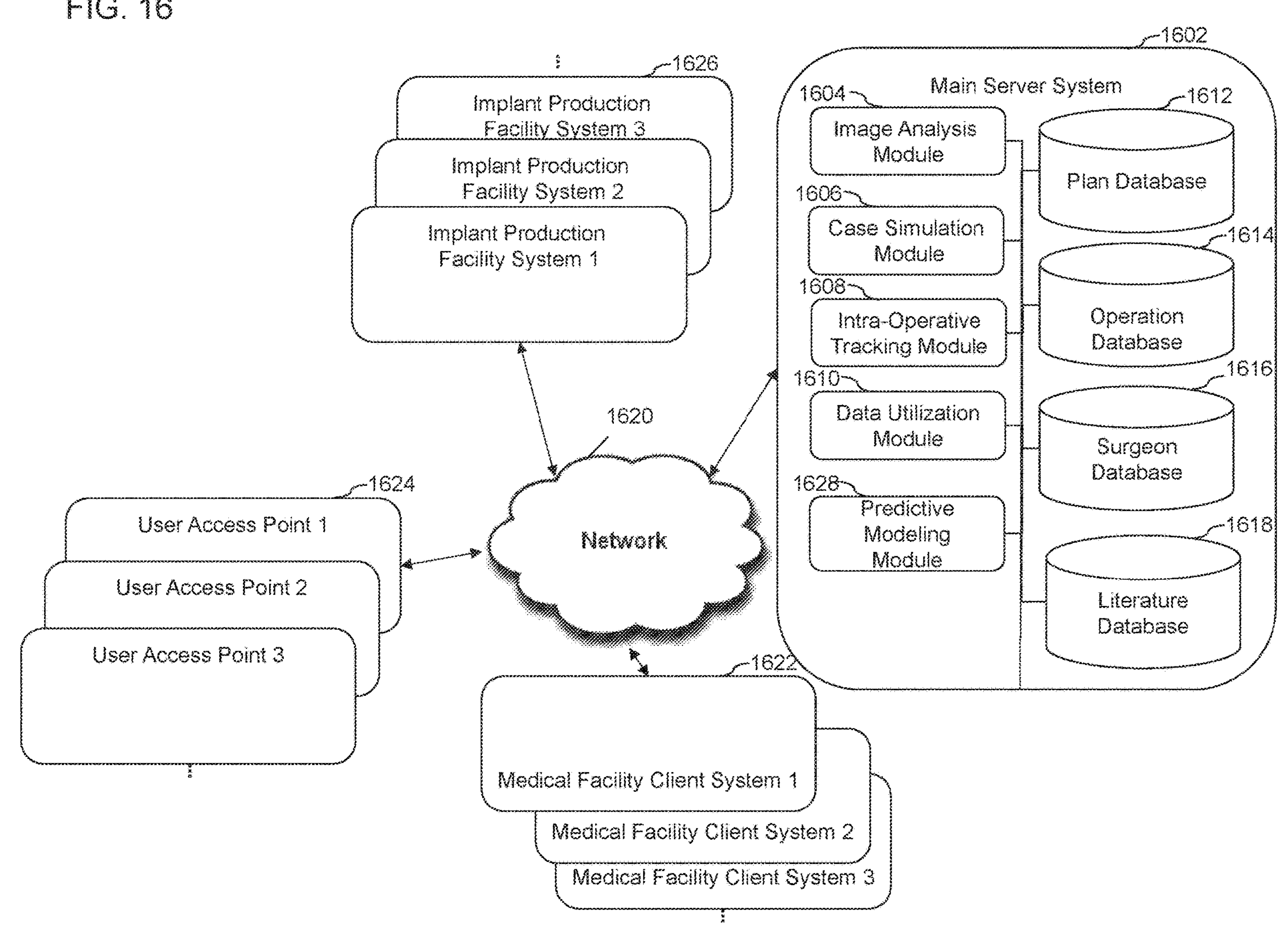
FIG. 16
1626
Implant Production Facility System 3
Implant Production Facility System 2
Implant Production Facility System 1
1602
Main Server System
1604
Image Analysis Module
1606
Case Simulation Module
1608
Intra-Operative Tracking Module
1610
Data Utilization Module
1628
Predictive Modeling Module
1612
Plan Database
1614
Operation Database
1616
Surgeon Database
1618
Literature Database
1620
Network
1624
User Access Point 1
User Access Point 2
User Access Point 3
1622
Medical Facility Client System 1
Medical Facility Client System 2
Medical Facility Client System 3

1702
Central Processing Unit (CPU)
1706
Memory
1710
Patient-specific Spinal Treatment, Operations, and Procedures Module
1714
Mass Storage Device
1704
Multimedia Devices
1708
I/O Devices And Interfaces
1712
1716
Network
1718
Data Source
1722
Computing Systems
1720

SYSTEMS, METHODS, AND DEVICES FOR DEVELOPING PATIENT-SPECIFIC SPINAL TREATMENTS, OPERATIONS, AND PROCEDURES

CROSS-REFERENCE TO RELATED APPLICATIONS

The present application is a continuation of U.S. patent application Ser. No. 17/496,222, filed Oct. 7, 2021, which is a continuation of U.S. patent application Ser. No. 15/958,409, filed Apr. 20, 2018, which claims the benefit under 35 U.S.C. § 119 (c) of U.S. Provisional Patent Application No. 62/488,077, filed Apr. 21, 2017, U.S. Provisional Patent Application No. 62/518,305, filed Jun. 12, 2017, U.S. Provisional Patent Application No. 62/518,310, filed Jun. 12, 2017, U.S. Provisional Patent Application No. 62/597,035, filed Dec. 11, 2017, and U.S. Provisional Patent Application No. 62/612,260, filed Dec. 29, 2017, each of which is incorporated herein by reference in its entirety under 37 C.F.R. § 1.57. Any and all applications for which a foreign or domestic priority claim is identified in the Application Data Sheet as filed with the present application are hereby incorporated by reference under 37 C.F.R. § 1.57.

BACKGROUND

Field

The present application relates to spinal rods and surgical planning and procedures thereof.

Description

Spinal surgery is one of the most frequently performed surgical procedures worldwide. Generally speaking, spinal surgery may involve implantation of a spinal rod to correct the curvature of the spine of a patient and to prevent further deterioration. As such, the particular curvature of the spinal rod can be a key factor in obtaining successful results from surgery.

SUMMARY

Various embodiments described herein relate to systems, methods, and devices for developing patient-specific spinal treatments, operations, and procedures. In some embodiments, systems, methods, and devices described herein for developing patient-specific spinal treatments, operations, and procedures can comprise an iterative virtuous cycle. The iterative virtuous cycle can further comprise preoperative, intraoperative, and postoperative techniques or processes. For example, the iterative virtuous cycle can comprise imaging analysis, case simulation, implant production, case support, data collection, machine learning, and/or predictive modeling. One or more techniques or processes of the iterative virtuous cycle can be repeated.

In some embodiments, a system for developing one or more patient-specific spinal implants comprises: one or more computer readable storage devices configured to store a plurality of computer executable instructions; and one or more hardware computer processors in communication with the one or more computer readable storage devices and configured to execute the plurality of computer executable instructions in order to cause the system to: access one or more medical images of a spine of a patient; simulate, on the one or more medical images, implantation of a spinal rod to a vertebral segment of interest, wherein the simulation of implantation of the spinal rod further comprises: identifying one or more reference points along the vertebral segment of interest; and rotating one or more portions of the one or more medical images around the identified one or more reference points to obtain a desired surgical output curvature of the spine of the patient; determine, based at least in part on the simulation of implantation of the spinal rod, one or more dimensions of a patient-specific spinal rod for the vertebral segment of interest, wherein the one or more dimensions of the patient-specific spinal rod comprises a diameter and curvature thereof; generate spinal rod manufacturing or selection data instructions, based at least in part on the determined one or more dimensions of the patient-specific spinal rod, for use by a spinal rod manufacturing or selection apparatus for producing or selecting the patient-specific spinal rod for the vertebral segment of interest; determine, from the one or more medical images, a length of an anterior longitudinal ligament for the vertebral segment of interest and a length of a posterior longitudinal ligament for the vertebral segment of interest; determine, from the one or more medical images, a length of an anterior curve for the vertebral segment of interest and a length of a posterior curve for the vertebral segment of interest; simulate, on the one or more medical images, implantation of one or more cages to one or more intervertebral spaces within the vertebral segment of interest, wherein the simulation of implantation of the one or more cages further comprises: increasing a posterior height of each of the one or more cages until the length of the posterior curve substantially matches or does not exceed the length of the posterior longitudinal ligament; and increasing lordosis of each of the one or more cages while maintaining the length of the anterior curve shorter than the anterior longitudinal ligament; determine, based at least in part on the simulation of implantation of the one or more cages, one or more dimensions of each of one or more patient-specific cages for the vertebral segment of interest, wherein the one or more dimensions of each of the one or more patient-specific cages comprises posterior height and anterior height thereof; and generate cage manufacturing or selection data instructions, based at least in part on the determined one or more dimensions of each of the one or more patient-specific cages, for use by a cage manufacturing or selection apparatus for producing or selecting the one or more patient-specific cages for the one or more intervertebral spaces, wherein the patient-specific spinal rod for the vertebral segment of interest is produced or selected from a pre-existing range of spinal rods based at least in part on the generated spinal rod manufacturing or selection data instructions, and wherein the one or more patient-specific cages for the one or more intervertebral spaces are produced or selected from a pre-existing range of cages based at least in part on the generated cage manufacturing or selection data instructions.

In certain embodiments, the system is further caused to: determine, from the one or more medical images, for each vertebra within the vertebral segment of interest, a screw insertion axis projected length on a sagittal plane and vertebral body width; determine, based at least in part from predetermined spinal anatomical data, literature, or surgeon preferences, for each vertebra within the vertebral segment of interest, an assumed or predetermined angulation of an implanted screw in reference to an endplate to which the screw is configured to be attached to, an assumed or predetermined angle between a vertebra axis and a pedicle axis on a transverse plane, an assumed or predetermined ratio between screw length and screw insertion axis length, and an assumed or predetermined ratio between vertebral body width and pedicle width; generate one or more desired lengths of one or more patient-specific screws for insertion in each vertebra within the vertebral segment of interest based at least in part on the determined screw insertion axis projected length on the sagittal plane, the determined vertebral body width, the assumed or predetermined angle between the vertebra axis and the pedicle axis on the transverse plane, and the assumed or predetermined ratio between screw length and screw insertion axis length; generate one or more desired diameters of the one or more patient-specific screws for insertion in each vertebra within the vertebral segment of interest based at least in part on the determined screw insertion axis projected length on the sagittal plane, the determined vertebral body width, and the assumed or predetermined ratio between vertebral body width and pedicle width; and generate screw manufacturing or selection data instructions, based at least in part on the determined one or more desired lengths and desired diameters, for use by a screw manufacturing or selection apparatus for producing or selecting from a pre-existing range of screws the one or more patient-specific screws. In certain embodiments, at least one of the one or more patient-specific screws comprises one or more sensors, wherein the one or more sensors are configured to provide intraoperative tracking data, wherein the intraoperative tracking data comprises orientation and position data of a portion of the spine of the patient in substantially real-time, wherein the intraoperative tracking data is configured to assist a surgical procedure. In certain embodiments, the one or more patient-specific screws are configured to be inserted into one or more vertebra using a surgical tool, wherein the surgical tool comprises one or more sensors, wherein the one or more sensors are configured to provide intraoperative tracking data, wherein the intraoperative tracking data comprises orientation and position data of a portion of the spine of the patient in substantially real-time, wherein the intraoperative tracking data is configured to assist a surgical procedure.

In certain embodiments, the desired surgical output curvature of the spine is determined based at least in part on one or more predicted post-operative parameters, wherein the system is further caused to generate a prediction of the one or more post-operative parameters by: analyzing the one or more medical images to determine one or more pre-operative variables relating to the spine of the patient, wherein the one or more pre-operative variables comprise at least one of UIL, LIL, age of the patient, pelvic incidence pre-operative values, pelvic tilt pre-operative values, lumbar lordosis pre-operative values, thoracic kyphosis pre-operative values, or sagittal vertical axis pre-operative values; and generating a prediction of one or more post-operative variables based at least in part on applying a predictive model, wherein the predictive model is generated by: accessing a dataset from an electronic database, the dataset comprising data collected from one or more previous patients and spinal surgical strategy employed for the one or more previous patients; dividing the dataset into one or more categories based on spinal surgery domain knowledge; standardizing the data in the first subcategory; selecting a model algorithm to the data in the first subcategory; inputting a first set of input values from the first subcategory into the model algorithm to train the predictive model based on a first set of output values from the first subcategory; inputting a second set of input values from the second subcategory into the trained predictive model and comparing results generated by the trained predictive model with a second set of output values from the second subcategory; and storing the trained predictive model for implementation, wherein the post-operative parameters comprise one or more of pelvic tilt, lumbar lordosis, thoracic kyphosis, or sagittal vertical axis.

In certain embodiments, the one or more medical images of the spine comprise one or more of a sagittal x-ray image, a frontal x-ray image, a flexion x-ray image, an extension x-ray image, or a MRI image. In certain embodiments, the one or more medical images comprises one or more two-dimensional x-ray images, and wherein the system is further caused to calibrate the one or more two-dimensional x-ray images and generate a composite three-dimensional image based on the one or more two-dimensional x-ray images.

In some embodiments, a system for developing one or more patient-specific spinal implants comprises: one or more computer readable storage devices configured to store a plurality of computer executable instructions; and one or more hardware computer processors in communication with the one or more computer readable storage devices and configured to execute the plurality of computer executable instructions in order to cause the system to: access one or more medical images of a spine of a patient; determine, from the one or more medical images, a length of an anterior longitudinal ligament for a vertebral segment of interest and a length of a posterior longitudinal ligament for the vertebral segment of interest; determine, from the one or more medical images, a length of an anterior curve for the vertebral segment of interest and a length of a posterior curve for the vertebral segment of interest; simulate, on the one or more medical images, implantation of one or more cages to one or more intervertebral spaces within the vertebral segment of interest, wherein the simulation of implantation of the one or more cages further comprises: increasing a posterior height of each of the one or more cages until the length of the posterior curve substantially matches or does not exceed the length of the posterior longitudinal ligament; and increasing lordosis of each of the one or more cages while maintaining the length of the anterior curve shorter than the anterior longitudinal ligament; determine, based at least in part on the simulation of implantation of the one or more cages, one or more dimensions of each of one or more patient-specific cages for the vertebral segment of interest, wherein the one or more dimensions of each of the one or more patient-specific cage comprises posterior height and anterior height thereof; generate cage manufacturing or selection data instructions, based at least in part on the determined one or more dimensions of each of the one or more patient-specific cages, for use by a cage manufacturing or selection apparatus for producing or selecting the one or more patient-specific cages for the one or more intervertebral spaces, wherein the one or more patient-specific cages for the one or more intervertebral spaces are produced or selected from a pre-existing range of cages based at least in part on the generated cage manufacturing or selection data instructions; determine, from the one or more medical images, for each vertebra within the vertebral segment of interest, a screw insertion axis projected length on a sagittal plane and vertebral body width; determine, based at least in part from predetermined spinal anatomical data, literature, or surgeon preferences, for each vertebra within the vertebral segment of interest, an assumed or predetermined angulation of an implanted screw in reference to an endplate to which the screw is configured to be attached to, an assumed or predetermined angle between a vertebra axis and a pedicle axis on a transverse plane, an assumed or predetermined ratio between screw length and screw insertion axis length, and an assumed or predetermined ratio between vertebral body width and pedicle width; generate one or more desired lengths of one or more patient-specific screws for insertion in each vertebra within the vertebral segment of interest based at least in part on the determined screw insertion axis projected length on the sagittal plane, the determined vertebral body width, the assumed or predetermined angle between the vertebra axis and the pedicle axis on the transverse plane, and the assumed or predetermined ratio between screw length and screw insertion axis length; generate one or more desired diameters of the one or more patient-specific screws for insertion in each vertebra within the vertebral segment of interest based at least in part on the determined screw insertion axis projected length on the sagittal plane, the determined vertebral body width, and the assumed or predetermined ratio between vertebral body width and pedicle width; and generate screw manufacturing or selection data instructions, based at least in part on the determined one or more desired lengths and desired diameters, for use by a screw manufacturing or selection apparatus for producing or selecting from a pre-existing range of screws the one or more patient-specific screws.

In certain embodiments, at least one of the one or more patient-specific screws comprises one or more sensors, wherein the one or more sensors are configured to provide intraoperative tracking data, wherein the intraoperative tracking data comprises orientation and position data of a portion of the spine of the patient in substantially real-time, wherein the intraoperative tracking data is configured to assist a surgical procedure. In certain embodiments, the one or more patient-specific screws are configured to be inserted into one or more vertebra using a surgical tool, wherein the surgical tool comprises one or more sensors, wherein the one or more sensors are configured to provide intraoperative tracking data, wherein the intraoperative tracking data comprises orientation and position data of a portion of the spine of the patient in substantially real-time, wherein the intraoperative tracking data is configured to assist a surgical procedure.

In certain embodiments, the system is further caused to: simulate, on the one or more medical images, implantation of a spinal rod to the vertebral segment of interest, wherein the simulation of implantation of the spinal rod further comprises: identifying one or more reference points along the vertebral segment of interest; and rotating one or more portions of the one or more medical images around the identified one or more reference points to obtain a desired surgical output curvature of the spine of the patient; determine, based at least in part on the simulation of implantation of the spinal rod, one or more dimensions of a patient-specific spinal rod for the vertebral segment of interest, wherein the one or more dimensions of the patient-specific spinal rod comprises a diameter and curvature thereof; generate spinal rod manufacturing or selection data instructions, based at least in part on the determined one or more dimensions of the patient-specific spinal rod, for use by a spinal rod manufacturing or selection apparatus for producing or selecting the patient-specific spinal rod for the vertebral segment of interest, wherein the patient-specific spinal rod for the vertebral segment of interest is produced or selected from a range of pre-existing spinal rods based at least in part on the generated spinal rod manufacturing data instructions.

In certain embodiments, the desired surgical output curvature of the spine is determined based at least in part on one or more predicted post-operative parameters, wherein the system is further caused to generate a prediction of the one or more post-operative parameters by: analyzing the one or more medical images to determine one or more pre-operative variables relating to the spine of the patient, wherein the one or more pre-operative variables comprise at least one of UIL, LIL, age of the patient, pelvic incidence pre-operative values, pelvic tilt pre-operative values, lumbar lordosis pre-operative values, thoracic kyphosis pre-operative values, or sagittal vertical axis pre-operative values; and generating a prediction of one or more post-operative variables based at least in part on applying a predictive model, wherein the predictive model is generated by: accessing a dataset from an electronic database, the dataset comprising data collected from one or more previous patients and spinal surgical strategy employed for the one or more previous patients; dividing the dataset into one or more categories based on spinal surgery domain knowledge; standardizing the data in the first subcategory; selecting a model algorithm to the data in the first subcategory; inputting a first set of input values from the first subcategory into the model algorithm to train the predictive model based on a first set of output values from the first subcategory; inputting a second set of input values from the second subcategory into the trained predictive model and comparing results generated by the trained predictive model with a second set of output values from the second subcategory; and storing the trained predictive model for implementation, wherein the post-operative parameters comprise one or more of pelvic tilt, lumbar lordosis, thoracic kyphosis, or sagittal vertical axis.

In certain embodiments, the one or more medical images of the spine comprise one or more of a sagittal x-ray image, a frontal x-ray image, a flexion x-ray image, an extension x-ray image, or a MRI image. In certain embodiments, the one or more medical images comprises one or more two-dimensional x-ray images, and wherein the system is further caused to calibrate the one or more two-dimensional x-ray images and generate a composite three-dimensional image based on the one or more two-dimensional x-ray images.

In some embodiments, a system for developing one or more patient-specific spinal implants comprises: one or more computer readable storage devices configured to store a plurality of computer executable instructions; and one or more hardware computer processors in communication with the one or more computer readable storage devices and configured to execute the plurality of computer executable instructions in order to cause the system to: access one or more medical images of a spine of a patient; determine, from the one or more medical images, a height of each of one or more discs on a vertebral segment of interest; determine, for each of the one or more discs on the vertebral segment of interest, disc height as a percentage of total disc height of the vertebral segment of interest and/or disc angulation as a percentage of total disc angulation of the vertebral segment of interest; analyze the determined disc height percentage and/or determined disc angulation percentage of each of the one or more discs on the vertebral segment of interest by comparing the determined disc height percentage and/or determined disc angulation percentage of each of the one or more discs on the vertebral segment of interest with predetermined disc height percentages and/or predetermined disc angulation percentages of one or more corresponding discs of an asymptomatic population, wherein the predetermined disc height percentages and/or the predetermined disc angulation percentages of one or more corresponding discs of an asymptomatic population are updated periodically and/or continuously; simulate, on the one or more medical images, implantation of one or more cages to one or more intervertebral spaces within the vertebral segment of interest based at least in part on the comparison of the determined disc height percentage and/or the determined disc angulation percentage of each of the one or more discs on the vertebral segment of interest with predetermined disc height percentages and/or predetermined disc angulation percentages of the one or more corresponding discs of the asymptomatic population; determine, based at least in part on the simulation of implantation of the one or more cages, one or more dimensions of each of one or more patient-specific cages for the vertebral segment of interest, wherein the one or more dimensions of each of the one or more patient-specific cage comprises posterior height, anterior, and/or angulation height thereof; generate cage manufacturing or selection data instructions, based at least in part on the determined one or more dimensions of each of the one or more patient-specific cages, for use by a cage manufacturing or selection apparatus for producing or selecting the one or more patient-specific cages for the one or more intervertebral spaces, wherein the one or more patient-specific cages for the one or more intervertebral spaces are produced or selected from a pre-existing range of cages based at least in part on the generated cage manufacturing or selection data instructions; determine, from the one or more medical images, for each vertebra within the vertebral segment of interest, a screw insertion axis projected length on a sagittal plane and vertebral body width; determine, based at least in part from predetermined spinal anatomical data, literature, or surgeon preferences for each vertebra within the vertebral segment of interest, an assumed or predetermined angulation of an implanted screw in reference to an endplate to which the screw is configured to be attached to, an assumed or predetermined angle between a vertebra axis and a pedicle axis on a transverse plane, an assumed or predetermined ratio between screw length and screw insertion axis length, and an assumed or predetermined ratio between vertebral body width and pedicle width; generate one or more desired lengths of one or more patient-specific screws for insertion in each vertebra within the vertebral segment of interest based at least in part on the determined screw insertion axis projected length on the sagittal plane, the determined vertebral body width, the assumed or predetermined angle between the vertebra axis and the pedicle axis on the transverse plane, and the assumed or predetermined ratio between screw length and screw insertion axis length; generate one or more desired diameters of the one or more patient-specific screws for insertion in each vertebra within the vertebral segment of interest based at least in part on the determined screw insertion axis projected length on the sagittal plane, the determined vertebral body width, and the assumed or predetermined ratio between vertebral body width and pedicle width; and generate screw manufacturing or selection data instructions, based at least in part on the determined one or more desired lengths and desired diameters, for use by a screw manufacturing or selection apparatus for producing or selecting from a pre-existing range of screws the one or more patient-specific screws.

In certain embodiments, at least one of the one or more patient-specific screws comprises one or more sensors, wherein the one or more sensors are configured to provide intraoperative tracking data, wherein the intraoperative tracking data comprises orientation and position data of a portion of the spine of the patient in substantially real-time, wherein the intraoperative tracking data is configured to assist a surgical procedure.

In certain embodiments, the system is further caused to: simulate, on the one or more medical images, implantation of a spinal rod to the vertebral segment of interest, wherein the simulation of implantation of the spinal rod further comprises: identifying one or more reference points along the vertebral segment of interest; and rotating one or more portions of the one or more medical images around the identified one or more reference points to obtain a desired surgical output curvature of the spine of the patient; determine, based at least in part on the simulation of implantation of the spinal rod, one or more dimensions of a patient-specific spinal rod for the vertebral segment of interest, wherein the one or more dimensions of the patient-specific spinal rod comprises a diameter and curvature thereof; generate spinal rod manufacturing or selection data instructions, based at least in part on the determined one or more dimensions of the patient-specific spinal rod, for use by a spinal rod manufacturing or selection apparatus for producing or selecting the patient-specific spinal rod for the vertebral segment of interest, wherein the patient-specific spinal rod for the vertebral segment of interest is produced or selected from a range of pre-existing spinal rods based at least in part on the generated spinal rod manufacturing data instructions.

In certain embodiments, the desired surgical output curvature of the spine is determined based at least in part on one or more predicted post-operative parameters, wherein the system is further caused to generate a prediction of the one or more post-operative parameters by: analyzing the one or more medical images to determine one or more pre-operative variables relating to the spine of the patient, wherein the one or more pre-operative variables comprise at least one of UIL, LIL, age of the patient, pelvic incidence pre-operative values, pelvic tilt pre-operative values, lumbar lordosis pre-operative values, thoracic kyphosis pre-operative values, or sagittal vertical axis pre-operative values; and generating a prediction of one or more post-operative variables based at least in part on applying a predictive model, wherein the predictive model is generated by: accessing a dataset from an electronic database, the dataset comprising data collected from one or more previous patients and spinal surgical strategy employed for the one or more previous patients; dividing the dataset into one or more categories based on spinal surgery domain knowledge; standardizing the data in the first subcategory; selecting a model algorithm to the data in the first subcategory; inputting a first set of input values from the first subcategory into the model algorithm to train the predictive model based on a first set of output values from the first subcategory; inputting a second set of input values from the second subcategory into the trained predictive model and comparing results generated by the trained predictive model with a second set of output values from the second subcategory; and storing the trained predictive model for implementation, wherein the post-operative parameters comprise one or more of pelvic tilt, lumbar lordosis, thoracic kyphosis, or sagittal vertical axis.

In certain embodiments, the one or more medical images of the spine comprise one or more of a sagittal x-ray image, a frontal x-ray image, a flexion x-ray image, an extension x-ray image, or a MRI image. In certain embodiments, the one or more medical images comprises one or more two-dimensional x-ray images, and wherein the system is further caused to calibrate the one or more two-dimensional x-ray images and generate a composite three-dimensional image based on the one or more two-dimensional x-ray images.

In some embodiments, a system for providing intraoperative tracking to assist spinal surgery comprises: two or more active sensors, wherein each of the two or more active sensors comprises one or more accelerometers and/or one or more gyroscopes; two or more attachment devices, wherein each of the two or more attachment devices comprises one or more of said active sensors, a power source, and a wireless transmitter, wherein the two or more attachment devices are configured to be attached to two or more vertebrae in a configuration such that two of three axes of position data to be collected by the two or more active sensors are on a plane assumed to be parallel, or substantially parallel with a determinate angle, to a sagittal plane of a patient for spinal surgery, wherein when the two or more attachment devices are attached to two or more vertebrae during spinal surgery, each of the two or more active sensors are configured to provide position and/or orientation data of each of the two or more vertebrae to which each of the two or more attachment devices are attached to; one or more computer readable storage devices configured to store a plurality of computer executable instructions; and one or more hardware computer processors in communication with the one or more computer readable storage devices and configured to execute the plurality of computer executable instructions in order to cause the system to: receive the position and/or orientation data from the wireless transmitter of each of the two or more attachment devices in substantially real-time; dynamically determine, based at least in part on the position and/or orientation data and using gravity as a common reference among the position and/or orientation data received from the wireless transmitter of each of the two or more attachment devices, the position and/or orientation of the two or more vertebrae to which the two or more attachment devices are attached to; dynamically generate one or more performance metrics for spinal surgery based at least in part on comparing the determined position and orientation of the two or more vertebrae to which the two or more attachment devices are attached to with a predetermined surgical plan; and dynamically generate, based at least in part on the generated one or more performance metrics, guidance instructions for performing spinal surgery.

In certain embodiments, the one or more active sensors are configured to be an inertial measurement unit with six degrees of freedom. In certain embodiments, the one or more active sensors are configured to be an inertial measurement unit with nine degrees of freedom. In certain embodiments, the two or more attachment devices comprises a vertebral anchor. In certain embodiments, the two or more attachment devices comprises a surgical tool. In certain embodiments, the two or more attachment devices comprises a vertebral screw. In certain embodiments, the vertebral screw is a mono-axial screw comprising at least one sensor. In certain embodiments, the vertebral screw is a poly-axial screw comprising at least one sensor.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

A better understanding of the devices and methods described herein will be appreciated upon reference to the following description in conjunction with the accompanying drawings, wherein:

FIG. 2 is a flowchart illustrating an example embodiment(s) of pre-operative imaging analysis and/or case simulation for developing patient-specific spinal treatments, operations, and procedures;

FIG. 3 is a flowchart illustrating an example embodiment(s) of implant production, case support, and/or data collection for developing patient-specific spinal treatments, operations, and procedures;

FIG. 4 is a flowchart illustrating an example embodiment(s) of data collection, machine learning, and/or predictive modeling for developing patient-specific spinal treatments, operations, and procedures;

FIGS. 7A and 7B illustrate example embodiments of spinal rods that can be produced and/or selected using certain embodiment(s) of systems, devices, and methods for patient-specific spinal treatments, operations, and procedures;

FIG. 7C illustrates an example embodiment of a cage(s) that can be produced and/or selected using certain embodiment(s) of systems, devices, and methods for patient-specific spinal treatments, operations, and procedures;

FIG. 7D illustrates an example embodiment of a screw(s) that can be produced and/or selected using certain embodiment(s) of systems, devices, and methods for patient-specific spinal treatments, operations, and procedures;

FIG. 8 is a flowchart illustrating an example embodiment(s) of cage and/or screw design, production, modification, and/or selection;

FIG. 9B illustrates an example embodiment(s) of cage design, production, modification, and/or selection;

FIG. 9C illustrates an example embodiment(s) of cage design, production, modification, and/or selection;

FIG. 10B illustrates an example embodiment(s) of cage design, production, modification, and/or selection;

FIG. 10C illustrates an example embodiment(s) of cage design, production, modification, and/or selection;

FIG. 12B is a schematic diagram illustrating certain aspect(s) of an example embodiment(s) of screw design, production, modification, and/or selection;

FIGS. 14A-14E illustrate example embodiments of tools and/or sensors that can be used for intraoperative tracking;

FIG. 15 is a flowchart illustrating an example embodiment(s) of predictive modeling;

FIG. 16 is a schematic diagram illustrating an embodiment of a system for developing patient-specific spinal treatments, operations, and procedures.

DETAILED DESCRIPTION

Figure 1:
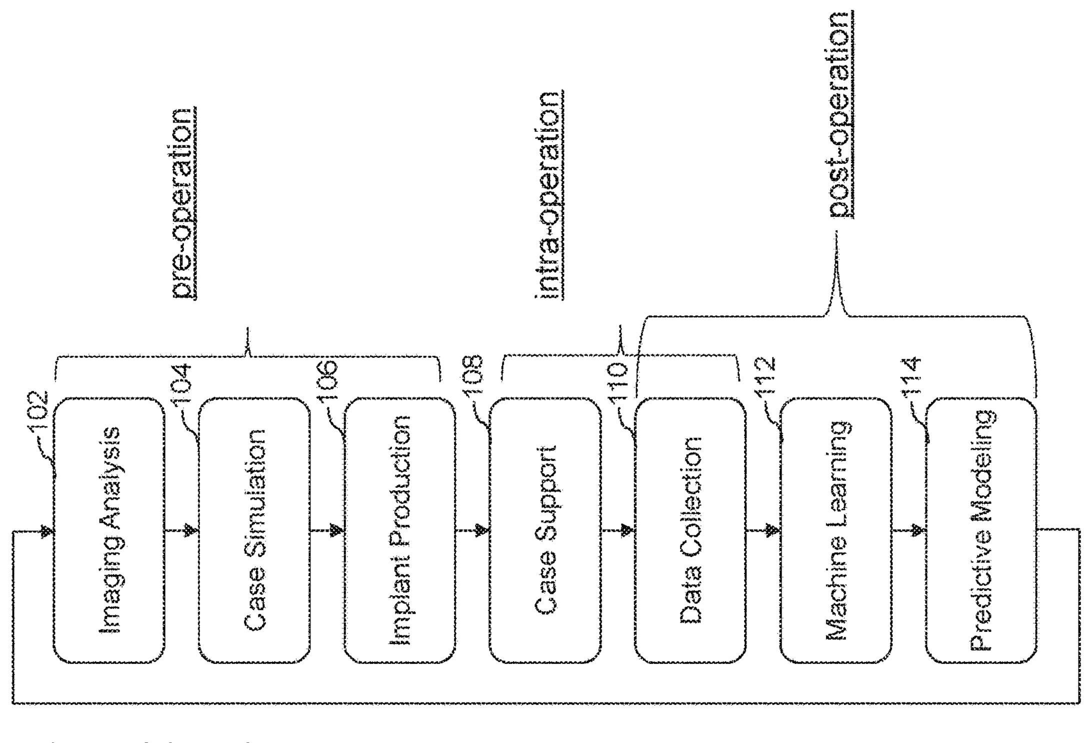
FIG. 1 is a flowchart illustrating an overview of an example embodiment(s) of an iterative virtuous cycle for developing patient-specific spinal treatments, operations, and procedures.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Spinal surgery is one of the most frequently performed surgical procedures worldwide. Generally speaking, spinal surgery may involve implantation of one or more implants, such as spinal rod(s), cage(s), and/or one or more screw(s) to correct the curvature of the spine of a patient and to prevent further deterioration. As such, correspondence between one or more spinal implants and patient anatomy can be a key factor in obtaining successful results from surgery. In particular, the particular curvature, dimensions, shape and/or size of one or more spinal rods, cages, and/or screws can be crucial to obtain successful surgical results.

Various embodiments described herein relate to systems, methods, and devices for developing patient-specific spinal treatments, operations, and procedures. In some embodiments, systems, methods, and devices described herein for developing patient-specific spinal treatments, operations, and procedures can comprise an iterative virtuous cycle. The iterative virtuous cycle can further comprise preoperative, intraoperative, and postoperative techniques or processes. For example, the iterative virtuous cycle can comprise imaging analysis, case simulation, implant production, case support, data collection, machine learning, and/or predictive modeling. One or more techniques or processes of the iterative virtuous cycle can be repeated.

In particular, there can be a desired surgical outcome that is particular to each patient. For example, based on the current state of a patient's spine, it can be known from past data, experience, and/or literature, that a particular patient's spine should be corrected in a certain way and/or degree. In turn, in order to obtain such corrective results, it can be advantageous to design, generate, and/or other formulate specific dimensions and/or other variables pertaining to one or more implants that are specific to the particular patient. For example, there can be one or more desirable variables and/or parameters for one or more spinal rods, cages, and/or screws for implantation for a specific patient. As such, certain systems, devices, and methods described herein are configured to utilize one or more medical images of a patient and analyze the same to determine one or more desired parameters and/or variables of one or more spinal rods, cages, and/or screws for implantation. Based on the determined one or more desired parameters and/or variables, certain systems, devices, and methods described herein can be further configured to manufacture, produce, modify, select, provide guidance for selection of, and/or generate instructions to manufacture, produce, modify, and/or select one or more spinal rods, cages, and/or screws that are specifically customized for a particular patient.

In addition to designing, producing, and/or otherwise obtaining an ideal or desired spinal implant, it can be equally, if not more, important that such implant is correctly implanted according to a desired and/or predetermined surgical plan. In other words, even if one or more spinal rods, cages, and/or screws are produced, selected, or otherwise obtained for a specific patient, its effects can be limited if the implantation or other surgical procedure is not conducted according to a desired or predetermined plan. As such, it can be advantageous to be able to ensure or at least increase the chances that surgery or a procedure thereof is performed as desired. To such effect, certain systems, devices, and methods described herein provide intraoperative tracking to provide guidance and/or performance evaluation during spinal surgery.

Further, although every patient is different and can have unique spinal conditions, some spinal conditions can be more similar than others. Also, certain individual characteristics of patients' spinal conditions can be more similar than others. As such, it can be advantageous to be able to analyze data relating to specific patient spinal conditions pre-operation and/or post-operation and utilize the same in order to predict the outcome of spinal surgery for a new patient. The predictive analysis can also be used in generating a patient-specific surgical plan, which can comprise one or more parameters and/or variables for one or more spinal rods, cages, and/or screws. Accordingly, certain systems, methods, and devices disclosed herein are configured to utilize predictive modeling to generate predictive surgical outcome(s) and/or patient-specific surgical plan(s).

Iterative Virtuous Cycle

FIG. 1 is a flowchart illustrating an overview of an example embodiment(s) of an iterative virtuous cycle for developing patient-specific spinal treatments, operations, and procedures. As illustrated in FIG. 1, some embodiments of the systems, methods, and devices comprise one or more processes that can form an iterative virtuous cycle. For example, an iterative virtuous cycle can comprise one or more of the following: (1) imaging analysis 102; (2) case simulation 104; (3) implant production 106; (4) case support 108; (5) data collection 110; (6) machine learning 112; and/or (7) predictive modeling 114. Certain embodiments may comprise any subset of the aforementioned processes. Further, one or more processes or techniques of a virtuous iterative cycle can be repeated.

Certain processes or techniques of the virtuous iterative cycle can be performed at different points in time. For example, imaging analysis, case simulation, and/or implant production can be performed pre-operation. Case support and/or data collection may be performed during operation or intra-operation. Lastly, some data collection, machine learning, and/or predictive modeling can be performed post-operation. The whole virtuous iterative cycle and/or portions thereof can be repeated for the same and/or different patient in certain embodiments.

FIG. 2 is a flowchart illustrating an example embodiment (s) of pre-operative imaging analysis and case simulation for developing patient-specific spinal treatments, operations, and procedures. Imaging analysis can relate to analysis of one or more medical images. For example, one or more x-ray images of a patient, such as a frontal x-ray and sagittal x-ray image, may be analyzed. In other embodiments, the one or more medical images can comprise an MRI scan, other x-ray image, CT scan, and/or any other medical image. The analysis of the one or more medical images can comprise drawing one or more rod designs as an overlay onto the one or more medical images. For example, in some embodiments, one or more rods with particular curvatures can be drawn as an overlay onto one or more x-ray images.

As illustrated in FIG. 2, in some embodiments, a medical imaging system can be configured to obtain and/or access one or more medical images of a patient at block 202. The one or more medical images can be two-dimensional and/or three-dimensional. The one or more medical images can be a sagittal view x-ray, a frontal view x-ray, a flexion x-ray, extension x-ray, a CT scan, and/or MRI scan of the spine of a patient. The medical facility client system can be configured to access and/or obtain the one or more medical images for output to a main server system for developing patient-specific spinal treatments, operations, and/or procedures.

At block 204, the main server system can be configured to receive and/or access the one or more medical images from the medical facility client system. For example, the one or more medical images can be electronically transmitted over the Internet in some embodiments. In other embodiments, one or more medical images can be inputted to the main server system offline, for example through a portable electronic storage medium, image film, or the like.

In embodiments in which CT and/or MRI scans are utilized, a complete three-dimensional reconstruction of the spine may be obtained directly from the CT and/or MRI scan itself. This can be useful for further analysis, such as determining one or more parameters and/or variables from the medical image(s), to generate appropriate and/or desired spinal treatments, operations, and/or procedures specific to a patient. However, CT or MRI scans may not be available for all patients due to the added expense and general availability of such modalities.

Rather, in some embodiments, the system can be configured to utilize one or more x-ray images, which are more widely available, to determine one or more parameters and/or variables in order to generate appropriate and/or desired spinal treatments, operations, and/or procedures specific to a patient. In some embodiments, the system is configured to analyze one or more two-dimensional x-ray images, such as sagittal view, front view, flexion, and/or extension images, separately and/or in combination for further analysis, for example to determine one or more parameters and/or variables. In certain embodiments, the system can be configured to combine one or more two-dimensional x-ray images, such as those describe above, to obtain a three-dimensional reconstruction of the spine for further analysis. For example, the system can be configured to combine a frontal x-ray view and a sagittal x-ray view for flexion and/or extension states. In other embodiments, the system can be configured to utilize a combination of one or more x-ray, MRI, and/or CT images.

In order to effectively utilize a plurality of medical images, the system can be configured to calibrate the plurality of medical images at block 206. More specifically, a common point of reference among the plurality of medical images can be identified and used for calibration and analysis. The system can be configured to identify a common point of reference among a plurality of medical images either automatically and/or by manual input from a user. For example, a central point of the sacrum endplate or vertebra can be identified as a common point of reference on a plurality of medical images. In particular, the center point of the sacrum vertebra on a frontal view x-ray image and a sagittal view x-ray image can be identified.

Further, in certain embodiments, the plurality of medical images can be scaled for consistency among the plurality of images. The calibration process can comprise identifying a common part, portion, and/or shape of the spine of the patient in a plurality of x-ray images and adjusting the scale of one or more of the plurality of x-ray images based on such commonality. For example, if the L3 plate length is chosen as a common feature, the length of the L3 plate can be measured on each of a plurality of x-ray images, and the x-ray images can be scaled to match such length.

The calibration process or technique can be fully or partially automated. In some embodiments, the calibration and/or adjustment processes can be automated by extracting the colon spine and/or measuring the central plate for example. After a plurality of medical images are calibrated, the system can be configured to generate a composite three-dimensional image at block 208 for further analysis. In other embodiments, a single medical image or scan is used, thereby not requiring any calibration.

The system can be configured to analyze the one or more medical images at block 210. Image analysis can comprise identifying one or more endplates, identifying the distance and/or curvature between one or more endplates, drawing one or more lines between one or more endplates, or the like. The one or more parameters can be obtained by the system automatically and/or by manual input. In addition, image analysis can further comprise modifying one or more medical images, for example by rotating one or more portions thereof, for example around an identified reference point and/or axis, to mimic a desired surgical outcome of the spine. In some embodiments, one or more image analysis processes can be performed prior to and/or after image modification such as rotation of one or more portions of the one or more medical images.

Analysis of the one or more medical images can depend on a number of factors, such as parameters and/or variables identified by surgeons, literature, and/or a historical database of the system. Accordingly, as illustrated in FIG. 2, the system at block 210 can be configured to communicate with one or more of a surgeon database 212, literature database 214, plan database 216, and/or operation database 218 in analyzing the one or more medical images. Each or all of the surgeon database 212, literature database 214, plan database 216, and/or operation database 218 can be configured to be updated continuously and/or periodically.

The surgeon database 212 can comprise preferences of a particular surgeon, for example certain surgical procedures or choices a particular surgeon routinely utilizes or favors and certain parameters of the spine that may be required to meet such surgeon preferences. Based on such determination, the system can be configured to analyze the one or more medical images to meet the preferences of a particular surgeon for example.

The literature database 214 can comprise one or more medical literatures, for example related to spinal surgery. As medical research is developed, additional parameters of the spine can be identified as being helpful in surgical planning. In addition, more real-life patient data can be made available, which can include pre-operative and/or post-operative data. As such, in certain embodiments, the literature database 214 can be used by the system to identify certain parameters, variables, and/or additional data of the spine that the system can utilize in analyzing the one or more medical images.

The plan database 216 and/or operation database 218 can comprise internal data of the system. In other words, the plan database 216 can comprise data related to one or more previous spinal surgical plans developed by the system. Similarly, the operation database 218 can comprise data related to actual spinal surgeries previously performed, including surgeries performed utilizing the system. Such data related to previously planned and/or executed spinal surgeries can also provide or identify parameters for the system to identify and/or determine as part of analyzing the one or more medical images.

After image analysis, surgical planning can be performed as part of case simulation at block 220. Surgical planning can comprise, for example, the design, production, modification, and/or selection of one or more spinal rods, screws, and/or cages to be used for a particular patient, for example based on the analysis of one or more medical images. More specifically, in certain embodiments, a surgical plan generated by the system can comprise one or more of the length, diameter, curvature, angulation, and/or other dimension of an implant, such as a spinal rod, screw, and/or cage. For example, the system can be configured to draw and/or allow a user to draw a spinal rod of a particular curvature as an overlay onto the one or more medical images. In particular, in some embodiments, the system can be configured to draw a spline on the spine on one or more medial images and obtain a global measurement of the spine as drawn. The system can be also configured to obtain local data, such as the corner of every vertebra for analysis. In certain embodiments, the system can be configured to generate a surgical plan comprising design and/or selection of a range, root, length and/or diameter of one or more spinal screws. Moreover, in certain embodiments, the generated surgical plan can comprise a design, shape, size, material, or the like of specific implant, such as a body device or cage.

Similar to image analysis, the system can be configured to communicate with one or more of a surgeon database 212, literature database 214, plan database 216, and/or operation database 218 in conducting surgical planning. For example, the system can be configured to take into account surgeon-specific preferences in planning. The system can also be configured to consider medical literature. The system can also be configured to consider its internal database comprising previously determined and executed surgical plans and operations. The system can be configured to identify one or more previous spinal surgeries conducted utilizing the system that may be similar and/or other provide guidance to the current patient case, based on age, severity of deformation, bone strength or density, or the like. The system can be configured to look in one or more databases to identify similar cases that were previously performed, identify the surgical strategies previously used in those cases, and identify the results to assist in planning. For example, in some embodiments, the system can take into account the trajectory and/or insertion depth of a screw(s) and/or the position of cages. More specifically, the trajectory and/or insertion depth of a screw from one or more previous surgeries can be used as an input in determining a desired screw length, trajectory, and/or insertion depth for a current surgery. In some embodiments, the system can be configured to determine a recommended implant design, positioning, and/or material(s) for a spinal rod, screw(s), or cage(s) based on previously collected data. For example, the previously collected data may be selected from certain cases comprising particular clinical results and/or bone quality and/or age of a patient.

In some embodiments, the generated surgical plan can comprise a particular design and/or curvature of a spinal rod for a particular patient, including rod diameter, material, length, curvature or the like. For example, for the upper vertebrae, the system may recommend using a cervical thoracic rod(s). In some embodiments, only one plan is designed and provided to a surgeon. In other embodiments, more than one plan can be designed and provided to a surgeon for final determination. For example, the number of surgical plans developed by a system for a single set of medical images of a single patent can comprise two, three, four, five, six, seven, eight, nine, and/or ten plans. In some embodiments, the system can be configured to develop and provide a surgeon with three plans. For example, the system can be configured to provide a first plan based on surgeon-inputted strategy and/or objectives. A second plan generated by the system can be based purely on scientific literature, and a third plan can be based on internal data of previously planned surgeries by the system. In particular, previously collected data can be analyzed to determine which strategies or plans had high success rates, over 90% for example, based on clinical outcomes such as angulation measurements for similar patients. The system can be further configured to receive a selection from a surgeon between one or more plans developed for a single patient. In other words, the system can be configured to generate a plurality of alternative surgical plans for a single patient.

In some embodiments, the system can be configured to provide case simulation guidance, for example to a surgeon, as part of developing patient-specific spinal treatments, operations, and procedures. In certain embodiments, the system can be configured to generate one or more surgical plans based on a surgeon's strategy and/or objectives that may have been previously inputted into the system. Additionally or alternatively, the surgical plan design can be data-driven, for example based on scientific literature and/or other data from previous surgeries. The scientific literature can be from 10-20 or more surgeons and/or can be continuously and/or periodically updated. The scientific literature can also be based on internal data collected from previous cases generated by the system. The system can also utilize machine-learning in some embodiments to continuously improve its surgical planning based on previous internal data and/or scientific literature. Surgical planning can also be based on big data and may utilize one or more big data processing techniques.

Objectives of spinal realignment can include, for example, surgeon-inputted guidelines, correction of thoracic kyphosis, age-related objectives, and/or future theory around sitting position. For example, growth of the spine can be considered in the planning stage for younger patients. Further, surgical balance of a patient may be dependent on the age of the patient. Case simulation capabilities of the system can include surgeon-inputted guidelines and/or strategy, strategy based on Smith-Petersen Osteotomy (SPO) (s), strategy based on Pedicle Subtraction Osteotomy (PSO) and SPO(s), strategy based on cage(s), and/or strategy based on cage(s) and SPO(s), and/or any combination of the above. Additional simulations can include Spondylolisthesis correction, compensatory mechanism of the thoracic area, and/or compression/distraction as requested and/or necessary. Some examples of surgeon inputs can include a type of spinal surgery, insertion of screws at certain portions, conducting a PSO at a certain level, conducting an SPO at a certain level, insertion of a cage at a particular portion, or the like.

Figure 5:
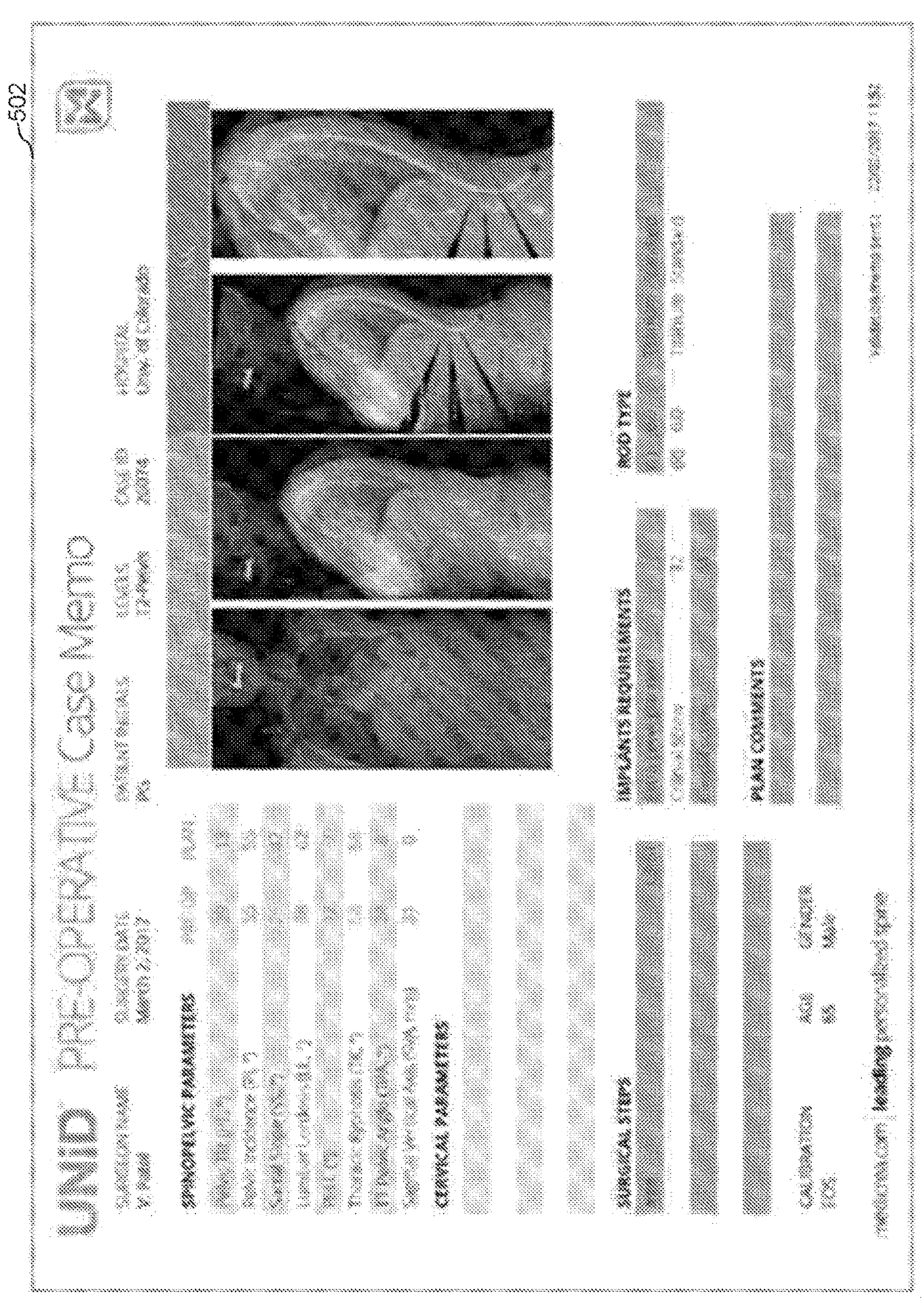
FIG. 5 illustrates an example embodiment(s) of case simulation delivery for developing patient-specific spinal treatments, operations, and procedures.
Figure 6:
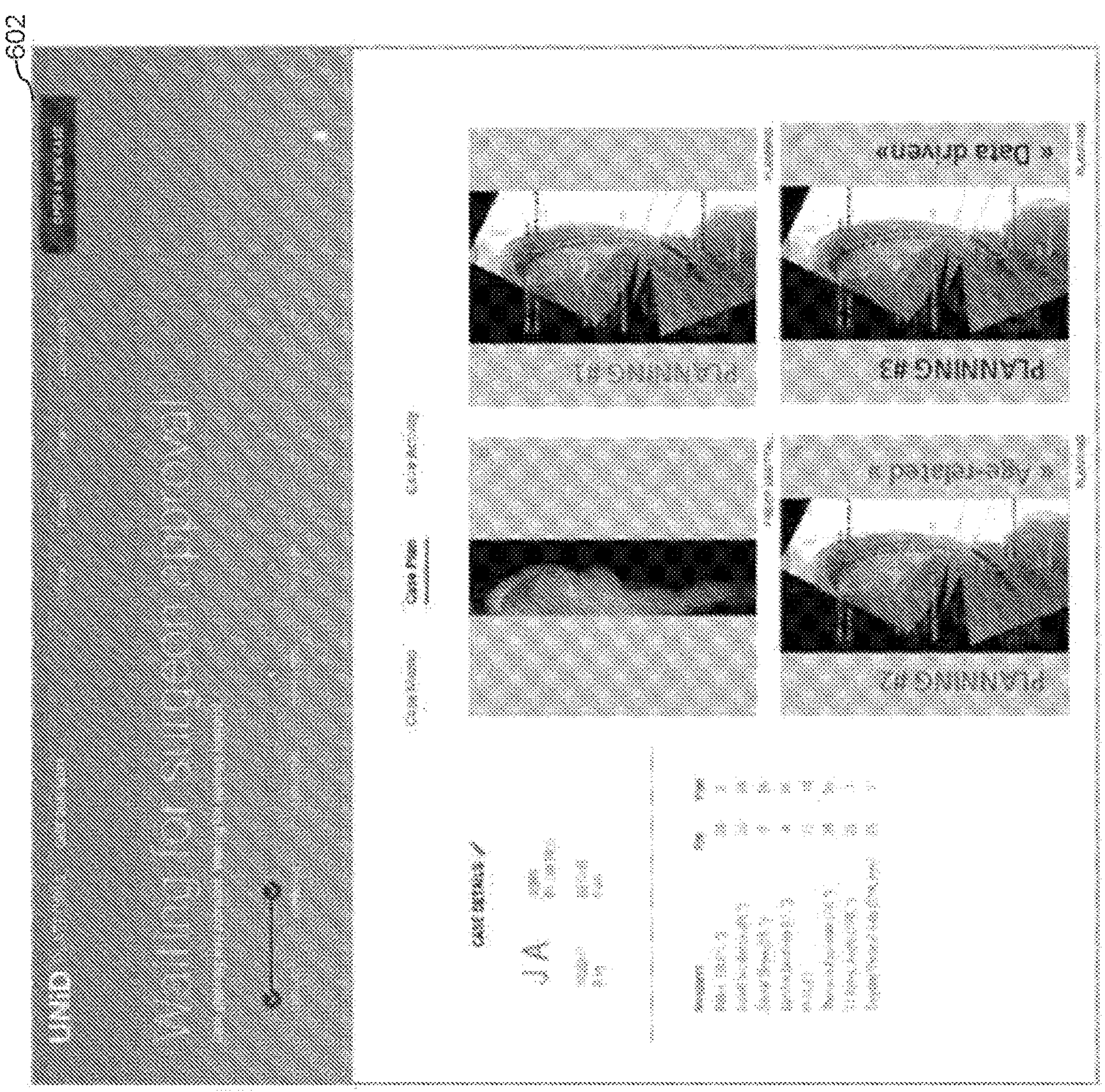
FIG. 6 illustrates an example embodiment(s) of case simulation delivery for developing patient-specific spinal treatments, operations, and procedures.

In some embodiments, a surgical plan generated by the system can comprise one or more pre-operative images and/or surgical plan images. FIGS. 5 and 6 illustrate example embodiments of case simulation delivery for developing patient-specific spinal treatments, operations, and procedures. As illustrated in FIGS. 5 and 6, as part of the planning process, the system can be configured to produce one or more plan images, in which a spinal rod, one or more screws, and/or one or more cages can be depicted on one or more modified or analyzed pre-operative images. For example, as part of the planning process, the system can be configured to partition a medical image into one or more portions and rotate such portions with respect to one another to obtain a depiction of post-operative results or objectives. In certain embodiments, the system is configured to identify each vertebra and rotate the same to obtain a post-operative estimated result or curvature of the spine. Rotation of each vertebra and/or one or more portions of a medical image that may comprise one or more vertebrae can be data-driven based on historical data and/or automated in certain embodiments. An overlay of a spinal rod can be added onto such planning image to provide a visual depiction of the surgical plan.

The surgical plan can also comprise one or more pre-operative and/or planned spinopelvic parameters, such as pelvic tilt (PT), pelvic incidence (PT), sacral slope (SS), lumbar lordosis (LL), PI-LL, thoracic kyphosis (TK), T1 pelvic angle, and/or sagittal vertical axis (SVA). The surgical plan can also comprise one or more cervical parameters, surgical steps, implant requirements, such as screws and/or rod type.

Referring back to FIG. 2, the system can be configured to electronically transmit the generated one or more surgical plans or otherwise allow a user to view or access the one or more surgical plans. For example, in some embodiments, a user access point system can be configured to receive one or more surgical plans and/or steps thereof at block 222. The user access point system can be a personal computer (PC), smartphone, tablet PC, or any other electronic device used by one or more medical personnel. The one or more generated plans can be sent to one or more medical personnel by e-mail, application message or notification, or the like.

The user access point system can be configured to display the one or more surgical plans and/or steps thereof at block 224. In some embodiments, a PDF or other viewable copy of the actual surgical plan can be transmitted to the user access point system for viewing. For example, FIG. 5 illustrates an example surgical plan in the form of a PDF memo that can be sent to medical personnel through one or more electronic communications methods, such as e-mail. In other embodiments, a link can be transmitted to a medical personnel or user access point system. By activating the link, the user access point system can be configured to display the one or more generated surgical plans, for example on a webpage or application page. For example, FIG. 6 illustrates an example surgical plan on a system platform, such as a webpage or application page viewable to one or more medical personnel by the system.

As briefly discussed above, a single surgical plan can comprise one or more steps, such as a PSO, SPO, cage insertion, and/or screw insertion. Each step of the plan can relate to a particular surgical procedure and/or result starting from a pre-operative state. For example, a surgical plan can comprise one, two, three, four, five, six, seven, eight, nine, ten, or more steps. All steps of a surgical plan can be made viewable to a user by the system. In some embodiments, the system and/or user access point system can be configured to allow a user to "deactivate" one or more steps, in order for example. In other embodiments, the system can be configured to allow a user to "deactivate" all steps of a plan at once to essentially view a pre-operative state.

In some embodiments, the image analysis, case simulation, and/or surgical planning can utilize one or more three-dimensional medical images to generate a three-dimensional plan. In certain embodiments, one or more two-dimensional medical images can be combined and/or otherwise utilized to generate a three-dimensional plan. For example, one or more x-ray images from different views, such as sagittal and/or frontal views, can be combined to generate a three-dimensional composite image, which can in turn be utilized to generate a three-dimensional surgical plan. More specifically, in some embodiments, a frontal x-ray image and a sagittal x-ray image can be combined using one or more scaling methods discussed above to form a composite three-dimensional image after scaling and/or coordination. In some embodiments, a generated three-dimensional plan can be used to determine one or more desired parameters and/or variables for one or more patient-specific spinal implants, such as spinal rod(s), cage(s), and/or screw(s) in three dimensions.

The systems, methods, and devices described herein can also be used to design, select, and/or produce other patient-specific implants as well, such as cages. In particular, CT scanning and/or three-dimensional printing can be utilized for the design, selection, and/or production of patient-specific cages. One or more features or techniques relating to composite x-ray images described herein can also be used for developing patient-specific cages. EOS x-ray imaging systems can also be used in connection with any embodiment herein.

Referring back to FIG. 2, in some embodiments, the user access point system can be configured to receive input from one or more medical personnel at block 226 regarding the generated one or more plans. For example, one or more medical personnel may select and/or validate one of a plurality of surgical plans developed by the system. Additionally, and/or alternatively, one or more medical personnel may request that a particular surgical plan be modified, for example by inserting comments and/or changing certain parameters and/or variables. The user access point system can be configured to relay or transmit such input to the main server system, which can further be configured to modify the one or more surgical plans at block 228 based on input received from the one or more medical personnel. At block 230, the system can be configured to present the final surgical plan(s) to one or more medical personnel, such as a surgeon, through a user access point system.

Subsequently, in certain embodiments, the system can be configured to produce, modify, and/or select, for example from pre-existing inventory, one or more patient-specific spinal rods, cages, and/or screws for implantation. For example, the system can be configured to produce, modify, and/or select one or more spinal rods that can be bent or otherwise desirable and/or specific to a particular patient prior to surgery. The one or more spinal rods can be configured to be used in minimally invasive surgery (MIS). In certain embodiments, an added benefit can be that real-time x-ray during surgery can be minimized or not used altogether to minimize radiation by the patient. Further, in some embodiments, the system can be configured to produce, modify, and/or select one or more cages and/or screws desirable and/or otherwise specific to a particular patient prior to surgery.

FIG. 3 is a flowchart illustrating an example embodiment(s) of implant production, case support, and data collection for developing patient-specific spinal treatments, operations, and procedures. In some embodiments, a computing system at an implant production and/or selection facility can be configured to access and/or receive a final surgical plan or a plurality thereof at block 302, for example via the Internet or a portable electronic storage medium. The implant production facility can be configured to produce, modify, and/or select one or more parts for the surgical procedure at block 304. For example, the implant production facility can be configured to produce a spinal rod(s), cage(s), and/or screw(s) based on specifications and/or materials specified in the surgical plan(s). Similarly, the implant production facility can be configured to select and/or modify one or more pre-produced spinal rods, cages, and/or screws based on specifications and/or materials specified in the one or more surgical plans.

In some embodiments, a spinal rod, cage, and/or screw can be produced from one or more different materials. The particular material to be used for a particular patient-specific rod(s), screw(s), and/or cage(s) can depend on data and/or can be selected by a surgeon. The particular material can also depend on the particular patient's height, weight, age, bone density, and/or bone strength, among others.

FIGS. 7A and 7B illustrate example embodiments of spinal rods that can be produced and/or selected, for example from a pre-existing range of spinal rods, using certain embodiment(s) of systems, devices, and methods for patient-specific spinal treatments, operations, and procedures. In some embodiments, the system can be configured to design, select, and/or produce one or more of thoraco lumbar rods, cervico thoracic rods, MIS rods, and/or 3D bent rods. In certain embodiments, a spinal rod can be made of titanium, cobalt-chrome alloy, and/or any other material.

As discussed above, in some embodiments, the system can be configured to produce, select, and/or modify a rod that is bent in one or more directions. Generally, it can be difficult, if not impossible, for a surgeon to bend a rod in even one direction, let alone more than one direction, using tools prior to or during surgery. In contrast, by utilizing a composite of two-dimensional x-ray images and/or three-dimensional medical images, the system can be configured to produce, and/or select from pre-existing inventory, a rod that is bent or curved in more than one direction, for example sideways and also in a sagittal direction.

FIG. 7C illustrates an example embodiment of a cage(s) that can be produced and/or selected, for example from a pre-existing range of cages, using certain embodiment(s) of systems, devices, and methods for patient-specific spinal treatments, operations, and procedures. FIG. 7D illustrates an example embodiment of a screw(s) that can be produced and/or selected, for example from a pre-existing range of screws, using certain embodiment(s) of systems, devices, and methods for patient-specific spinal treatments, operations, and procedures.

Referring back to FIG. 3, one or more medical personnel can select one or more implants, such as spinal rod(s), cage(s), and/or screw(s) for implantation at block 306 that was produced, modified, and/or selected by the implant production facility based on the surgical plan at block 304.

In some embodiments, one or more medical personnel can attach and/or activate one or more sensors for intraoperative tracking at block 308. The one or more sensors can be located in one or more screws and/or nuts for attaching to a patient's vertebrae and/or tools for attaching the same. One or more sensors that can be used in certain embodiments are discussed in more detail below. In some embodiments, for spinal surgeries, a sensor can be placed in or attached to every vertebra. This can be advantageous for providing accurate data. However, this may not be desirable in some situations due to the size of data. For example, a large amount of unnecessary data can be collected, when the angle of the vertebrae can be one of the most important parameters. As such, a sensor may be attached to only a subset of vertebrae that can provide valuable position and/or angular data of the spine.

In some embodiments, the system can be configured to utilize data collected from one or more sensors inside or attached to one or more screws implanted into the vertebrae instead of relying on imaging techniques, for example assuming that an implanted screw will be parallel to an endplate, in order to provide intraoperative tracking. In other words, angulation of a screw in a sagittal plane can be assumed to be equal or substantially equal to the vertebra angulation. In some embodiments, a top portion of a screw can comprise an active or passive sensor. The top portion can be broken off later during surgery in some embodiments such that the sensors can be re-used. The one or more screws comprising one or more sensors can be inserted into every vertebra or a subset thereof. For example, in some embodiments, sensors can be attached to all 20 vertebrae. In other embodiments, sensors can be attached to only a subset thereof, for example two or more sensors attached to the upper lumbar and/or two or more attached to the lower vertebra. The sensors can then be utilized for providing data relating to the position and/or angle or orientation of the vertebrae in six degrees of freedom (or nine degrees of freedom) in translation and rotation in real-time, near real-time, and/or substantially real-time. The raw data collected by the one or more sensors can be transmitted to a computer system to translate the raw data into tracking the position and/or orientation of one or more vertebrae, for example to assist in determining a spinal curvature and/or surgical correction.

Based on real-time, near real-time, and/or substantially intraoperative tracking or monitoring, the system can be configured to track the position and/or orientation or angulation of the vertebrae and/or screw(s). In other words, in some embodiments, correction of the spine during surgery can be monitored in real-time, near real-time, and/or substantially real-time. Referring again to FIG. 3, in certain embodiments, tracking data corresponding to the position and/or angulation of each vertebra can be transmitted to the main server system and/or a client system at the medical facility at block 310.

In certain embodiments, after one or more medical personnel inserts one, two, or more screws into the spine of a patient, the main server system and/or medical facility client system can be configured to track, analyze, and/or store movement of the different vertebrae during the correction and other operating procedure data at block 312. One or more medical personnel can thus visualize or otherwise track the position, orientation, correction and/or angulation of the vertebrae in real-time, near real-time, and/or substantially real-time and determine when desirable conditions, for example matching a pre-determined surgical plan, have been obtained. Such live-tracking can provide substantial assistance to the medical personnel. For example, without intraoperative tracking, a surgeon may believe that a 30 degree correction can be obtained when PSS is performed; however, in reality, a performed PSS may only result in a 10 degree correction. By providing intraoperative tracking or monitoring, in such situations, the surgeon can make further corrections as necessary before closing up the operation.

In certain embodiments, the system can be configured to conduct analysis of the tracked data by comparing the same to a pre-determined surgical plan. To do so, the system can retrieve data from the plan database 216 and/or operation database 218. Based on such comparison and/or analysis, the system can be configured dynamically generate and/or provide guidance to the surgeon during the operation in real-time and/or near real-time in block 314. For example, based on the tracked data, the system can be configured to instruct or guide the surgeon to change the angle of one or more vertebra based on the tracked data to obtain a curvature of the spine closer to the pre-determined planned.

The system can further be configured to provide an audible and/or visible alert and/or guidance to the surgeon. The audible and/or visible alert and/or guidance can comprise instructions to the surgeon to perform the surgery in a particular way or degree and/or alert the surgeon when the position and/or angulation of one or more vertebrae is within a predetermined threshold. For example, the system can be configured to provide an alert when the position and/or angulation of one or more screws and/or vertebrae is within about 1%, about 2%, about 3%, about 4%, about 5%, about 10%, about 15%, about 20%, about 25% of the predetermined plan and/or when within a range defined by two of the aforementioned values. In certain embodiments, the system can be configured to provide a visual depiction of the position, location, orientation, and/or angulation of each vertebra on a display based on the tracked data to guide the surgeon.

Once an acceptable level of angulation of the vertebrae if obtained, the surgeon can insert a spinal rod and/or tighten the screws to the rod and lock all parts for example to complete the surgery at block 316. In certain embodiments, the surgeon can then remove and/or deactivate the one or more sensors at block 318.

The system can further be configured to collect and/or utilize postoperative data in certain embodiments, for example to provide predictive modeling and/or other post-operation features or services. Moreover, in some embodiments, the system can be configured to take into account a level of sophistication and/or preferences of a surgeon to provide surgeon-specific recommendations for future cases. In certain embodiments, comparison and/or analysis of preoperative, intraoperative, and/or postoperative data and/or surgeon input can be used to determine a skill level and/or strategic preferences of a surgeon. The particular skill level of the surgeon and/or strategic preferences can be used to develop subsequent surgical planning for that surgeon. In addition, in some embodiments, data relating to growth of the spine and/or other subsequent developments, such as relating to curvature, can also be obtained from one or more postoperative x-ray images. Such long-term effects can also be utilized in preparing subsequent planning.

In some embodiments, as part of predictive modeling and/or machine learning, the system can be configured to analyze one or more different plans that were developed for a particular case. For example, in some embodiments, a first generated plan can be based on the strategy and/or objectives of a surgeon. A second generated plan for the same case can be based on data from scientific literature. A third generated plan for the same case can be based on historical data collected by the system through performance of surgical procedures. As more data is collected, and as more feedback and input are given and received from surgeons, and/or as more scientific research is conducted, the one or more generated plans and/or particular features thereof for a single case may converge. Certain parameters that converge more so than others can be utilized more heavily by the system in subsequent planning stages. Further, in certain embodiments, the system can be configured to compare a given case to previous cases in the planning stage. For example, the system can be configured to parse one or more databases to find one or more spines that match a given case and/or certain features thereof to make certain recommendations and/or predictions for planning.

FIG. 4 is a flowchart illustrating an example embodiment(s) of data collection, machine learning, and predictive modeling for developing patient-specific spinal treatments, operations, and procedures. In some embodiments, the system can be configured to retrieve preoperative, intraoperative, and/or postoperative data at block 402 from a plan database 216 and/or operation database 218.

In particular, in some embodiments, the system can be configured to collect one or more sets of data comprising one or more quantitative parameters and/or one or more x-ray images or other medical images. The one or more quantitative parameters can comprise, for each or one or more vertebra, and for each or one or more of pre-operation, planning stage, and/or post-operation, pelvic tilt (PT), pelvic incidence (PT), sacral slope (SS), lumbar lordosis (LL), PI-LL, thoracic kyphosis (TK), T1 pelvic angle, and/or sagittal vertical axis (SVA). The one or more x-ray images can be from pre-operation, planning stage, post-operation, and/or one or more years post-operation. The data collected can be used to build a database for future reference for data-driven and/or partially data-driven planning purposes for example.

In some embodiments, post-operation data can be collected continuously and/or periodically. For example, post-operation data, one or more parameters or variables thereof, and/or one or more medical images, such as x-ray images, of a patient's spine can be collected at or prior to three months post-operation, at or around six months post-operation, at or around one year post-operation, at or around two years post-operation, at or around three years post-operation, at or around four years post-operation, at or around five years post-operation, at or around ten years post-operation, at or around fifteen years post-operation, at or around twenty years post-operation, and/or between any of the aforementioned values and/or within a range defined by two of the aforementioned values.

In certain embodiments, the system can be further configured to retrieve surgeon inputted data and/or literature-based data at block 404. The surgeon-based data and/or literature-based data can be retrieved from the surgeon database 212 and the literature database 214 as described above.

In some embodiments, the system can be configured to analyze the preoperative, intraoperative, and/or postoperative data at block 406 and/or generate a report or other statistics at block 408. For example, in some embodiments, the system can be configured to compare one or more x-ray images from the planning stage, the operation stage, and post-operation. In order to provide an accurate comparison, the system can be configured to calibrate one or more x-ray images taken from different points in time in a similar manner as described above in relation to calibration of one or more x-ray images from different views. For example, a common point of reference, such as the center point of the sacrum endplate, can be selected on each of the x-ray images taken from different points in time. A length of a common feature, such as a plate length, can also be identified and used as a basis for scaling the x-ray images.

Based on calibrated x-ray images, the system can be configured to generate a report comprising an overlay of the spine of a patient pre-operation, intra-operation, and/or post-operation. One or more post-operative x-ray images may be provided, for example after 1 month from surgery, 6 months from surgery, 1 year from surgery, 2 years from surgery, 3 years from surgery, 5 years from surgery, 10 years from surgery, or the like. The x-ray images taken from different points in time and/or overlay(s) thereof can provide a visual sense of how closely the surgery was performed and/or how closely the surgical results were to the surgical plan.

The generated report can further comprise one or more sacral parameters, such as SVA, PI, LL, PI-LL, PT, or the like. The generated report can also comprise a percentage of achievement in comparison to the surgical plan. Accordingly, by comparing pre-operative and post-operative data, data relating to strengths and/or weaknesses of results of the surgical plan can be obtained. Further, by comparing pre-operative and intraoperative data, data relating to strengths and/or weaknesses of implementation by a particular surgeon can also be obtained.

The system can be configured to transmit the generated report and/or statistics to the surgeon who performed the surgery. For example, a user access point system of the surgeon can receive such generated report and/or statistics at block 410. After reviewing, the surgeon may provide input at block 412 through the user access point system. For example, the surgeon may provide input that certain procedures and/or selections could be improved. The surgeon may also provide and/or change general preferences based on the report. All such data can be stored in a database of the system for future reference. Such analysis can then be used for subsequent pre-operating planning and/or case simulation at block 414.

In certain embodiments, the system can also be configured to utilize machine learning techniques or processes. For example, the system can be configured to learn from previous plans and surgeries based on classification of a patient's severity, age, weight, height, and/or any other personal feature. The system can be configured to extract data from such machine learning database and/or process.

Cage/Screw Planning Overview

As discussed herein, in certain embodiments, the system can be configured to design, produce, modify, and/or provide guidance for selection of one or more patient-specific screws and/or cages to provide increased effectiveness of spinal surgery and/or to control cost. For example, one or more patient-specific screws and/or cages can be selected from a pre-existing range or inventory of screws and/or cages. In particular, in some embodiments, the system can be configured to design, produce, modify, and/or provide guidance for selection of one or more screws and/or cages to be used for a specific patient at a specific anatomical site, such as a particular vertebra and/or intervertebral space, based at least in part on analysis of one or more medical images. For example, the system can be configured to design a specific screw(s) for insertion into a specific vertebra and/or a specific cage(s) for insertion into a specific intervertebral space. In some embodiments, one or more processes and/or techniques described herein in relation to cage and/or screw planning, design, production, and/or selection can be utilized in combination and/or in conjunction with one or more other processes and/or techniques relating to cage, screw, and/or spinal rod planning, design, production, and/or selection and/or intraoperative tracking and/or predictive modeling, such as one or more such processes and techniques described herein. For example, in certain embodiments, a cage and/or screw design and/or planning technique can be used in conjunction with a spinal rod design and/or planning technique to ensure and/or maximize compatibility between the system-generated cage, screw, and/or spinal rod design and/or one or more design parameters thereof.

In particular, in some embodiments, the system can be configured to provide and/or recommend screw selection and/or one or more design parameters and/or dimensions thereof, including for example the diameter and/or length of one or more screws, as determined based in part on analysis of one or more x-ray images, MRI slices, and/or other medical image. Similarly, in some embodiments, the system can be configured to provide and/or recommend cage selection and/or one or more design parameters and/or dimensions thereof, including for example a footprint, posterior height, anterior height, width, length, and/or lordosis, as determined based in part on analysis of one or more x-ray images, MRI slices, and/or other medical image.

In certain embodiments, a surgical plan and/or image analysis output generated by the system can comprise one or more of a length(s), diameter(s), dimension(s), and/or angulation of an implant, such as a cage(s) and/or screw(s). More specifically, in some embodiments, the system can be configured to determine and/or generate a desired length and/or diameter of a screw, for example for insertion into a particular vertebra of a particular patient. In certain embodiments, the system can be configured to determine and/or generate a desired design, shape, size, and/or angulation of a specific interbody device, such as a cage, for example for insertion into a particular intervertebral space of a particular patient.

As such, in some embodiments, the system can be configured to design and/or determine one or more desired parameters of a patient-specific spinal cage(s) and/or screw(s) based on one or more specifications of a generated surgical plan(s), in order to ensure optimal and/or desired correspondence between one or more implants and the specific anatomy of a given patient. Accordingly, in certain embodiments, this process can reduce related costs by decreasing the necessary inventory of screws and/or cages that must be manufactured and/or kept in stock. Related costs can even further be reduced due to reduced sterilization costs of the same. An additional advantage can relate to decreased surgery time and simplification of surgical procedures, thereby increasing efficiency of surgery. For example, in some embodiments, the system can be configured to determine and/or generate certain criteria and/or dimensions for possibly acceptable screws and/or cages for use in a surgery for a particular patient. Based on such determination, in certain embodiments, a personalized caddie comprising a fewer selection of cages and/or screws, as determined prior to surgery, can be provided at the time of surgery.

In certain embodiments, the system can be configured to determine one or more desired parameters for one or more patient-specific screws and/or cages for a particular vertebral segment of interest using one or more processes or techniques described herein. For example, for one or more patient-specific screws, the system can be configured to determine a length, diameter, material, and/or type of one or more screws that are optimal and/or desired for a particular vertebra of a particular patient. For one or more patient-specific cages, the system can be configured to determine posterior height, anterior height, global height, angulation, material, and/or type of one or more cages that are optimal and/or desired for a particular intervertebral space(s) for a particular vertebral segment of interest. Based on the determined one or more desired parameters for one or more patient-specific cages and/or screws, in certain embodiments, the system can be configured to determine a range of acceptable cages and/or screws, for example from pre-existing inventory, for implantation and/or use in spinal surgery for a patient. For example, in some embodiments, a range of acceptable cages and/or screws can be defined by a range within about ±1% margin of error, about ±2% margin of error, about ±3% margin of error, about ±4% margin of error, about ±5% margin of error, about ±10% margin of error, about ±15% margin of error, about ±20% margin of error, about ±25% margin of error, and/or about ±30% margin of error from the determined one or more desired parameters for one or more patient cages and/or screws. In certain embodiments, a range of acceptable cages and/or screws can be defined by a range of margin of error between two of the aforementioned values.

FIG. 8 is a flowchart illustrating an example embodiment(s) of cage and/or screw design, production, modification, and/or selection. As illustrated in FIG. 8, in some embodiments, a medical facility client system is configured to access and/or obtain one or more two-dimensional and/or three-dimensional medical images at block 802. The one or more medical images can comprise one or more sagittal and/or frontal view x-ray images, flexion and/or extension x-ray images, CT images, MRI images, and/or medical images obtained using one or more other imaging modalities. In certain embodiments, a main server system can be configured to receive one or more two-dimensional and/or three-dimensional medical images from the medical facility client system at block 804, for example in a similar manner as described in relation to FIG. 2. In particular, one or more features described in relation to FIG. 2 relating to receiving and/or accessing medical images can be applicable to one or more process illustrated in FIG. 8 as well.

In some embodiments, the system can be configured to calibrate and/or scale one or more two-dimensional and/or three-dimensional medical images at block 806, for example to generate one or more composite medical images at block 808, for example in a similar manner as described in relation to FIG. 2. In particular, one or more features described in relation to FIG. 2 relating to calibrating and scaling medical image(s) and generating a composite image(s) thereof can be applicable to one or more processes illustrated in FIG. 8 as well.

In certain embodiments, the system can be further configured to conduct one or more analyses of the one or more medical images at block 810. For example, in some embodiments, the system can be configured to utilize posterior longitudinal ligament (PLL)-based analysis, anterior longitudinal ligament (ALL)-based analysis, combined ALL and PLL-based analysis, and/or mid-plate-based analysis for planning and/or designing patient-specific cages as will be described in more detail below. In any embodiments described herein, the system can be configured to further adjust any resulting parameters of a patient-specific cage(s), such as posterior height, anterior height, global height, and/or angulation, to ensure that the resulting spinal correction after implantation and/or simulated implantation of the patient-specific cage(s) does not overstretch the ALL and/or PLL and/or result in an ALL and/or PLL that is longer compared to the same before surgery. As such, in certain embodiments, the system can be configured to utilize the pre-operative ALL and/or PLL length as a not-to-exceed threshold(s) in specifying one or more design parameters for one or more patient-specific cages, such as posterior height, anterior height, and/or angulation of the one or more patient-specific cages, for example as a system check after determining one or more parameters for one or more patients-specific cages. For example, the system can be configured to ensure that, for a vertebral segment of interest, the resulting ALL and/or PLL length after implantation and/or simulated implantation of an intervertebral cage(s) does not exceed about 100% of the pre-operative ALL and/or PLL length, about 95% of the pre-operative ALL and/or PLL length, about 90% of the pre-operative ALL and/or PLL length, about 85% of the pre-operative ALL and/or PLL length, about 80% of the pre-operative ALL and/or PLL length, about 75% of the pre-operative ALL and/or PLL length, about 70% of the pre-operative ALL and/or PLL length, about 65% of the pre-operative ALL and/or PLL length, and/or about 60% of the pre-operative ALL and/or PLL length. In certain embodiments, the system can be configured to ensure that, for a vertebral segment of interest, the resulting ALL and/or PLL length after implantation and/or simulated implantation of an intervertebral cage(s) does not exceed a percentage of the pre-operative ALL and/or PLL length that is between two of the aforementioned values.

In some embodiments, analysis of the one or more medical images for purposes of cage and/or screw planning can also depend on a number of factors, such as parameters and/or variables identified by surgeons, surgeon preferences, spinal anatomical data, literature, and/or a historical surgery database of the system. Accordingly, as illustrated in FIG. 8, the system at block 810 can be configured to communicate with one or more of a surgeon database 212, literature database 214, plan database 216, and/or operation database 218 in analyzing the one or more medical images. Each or all of the surgeon database 212, literature database 214, plan database 216, and/or operation database 218 can be configured to be updated continuously and/or periodically.

In certain embodiments, based at least in part on the analyses conducted in block 810, the system can be configured to generate one or more desired parameters for a patient-specific cage(s) and/or screw(s) at block 812. For example, in some embodiments, the system can be configured to specify one or more of the following patient-specific parameters for one or more screws to be used in spinal surgery: root, length, and/or diameter. In addition, in certain embodiments, the system can be configured to specify one or more of the following patient-specific parameters for one or more cages to be implanted: type, design, shape, size, material, width, height, angulation, orientation, and/or length.

In some embodiments, a computing system at an implant production facility and/or medical facility client system can be configured to access and/or receive the generated desired one or more parameters for a patient-specific cage(s) and/or screw(s), for example via the Internet or a portable electronic storage medium. In certain embodiments, the implant production and/or selection facility and/or medical facility client system can be configured to produce, modify, and/or provide guidance for selection of one or more patient-specific screws and/or cages at block 814, based at least in part on the generated one or more desired parameters thereof.

Cage Planning-Posterior Approach

In certain embodiments, the system can be configured to provide cage planning and/or cage design, as part of case support for example. The system can be configured to determine certain cage(s) that are likely to fit a certain patient and recommend such one or more cage(s). More specifically, in some embodiments, the system can be configured to determine and/or focus on the length(s) of one or more ligaments, such as a posterior longitudinal ligament (PLL) and/or an anterior longitudinal ligament (ALL), that can be used as a guideline to ensure not to over-distract a particular patient's spine and/or attempt to over-correct the spine beyond its physiological capability. More specifically, for cage selection, it can be important not to select a cage(s) that may result in overstretching the spine beyond the length of a particular patient's longitudinal ligament(s). Accordingly, in some embodiments, the system is configured to measure one or more dimensions of one or more longitudinal ligaments, rather than simply measuring a straight line along the spinal column.

Figure 9A:
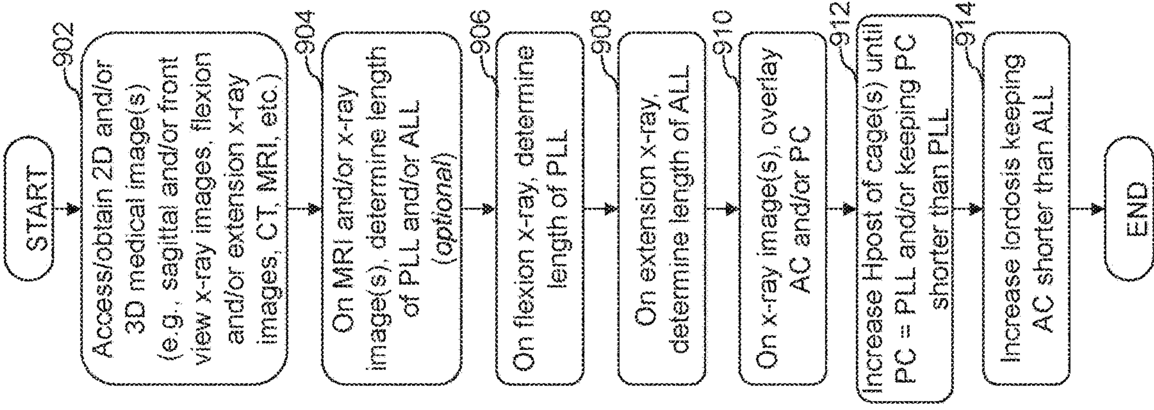
FIG. 9A is a flowchart illustrating an example embodiment(s) of cage design, production, modification, and/or selection.

FIG. 9A is a flowchart illustrating an example embodiment(s) of cage design, production, modification, and/or selection. As illustrated in FIG. 9A, in some embodiments, the system can be configured to utilize a posterior approach or a posterior-anterior approach. More specifically, in certain embodiments, the system is configured to access and/or obtain one or more two-dimensional and/or three-dimensional medical images, for example of a patient's spine, at block 902. The one or more medical images can comprise one or more sagittal and/or frontal view x-ray images, flexion and/or extension x-ray images, CT images, MRI images, and/or medical images obtained using one or more other imaging modalities.

In some embodiments, the system can be configured to measure the length of one or more ligaments from the one or more medical images. In order to account for maximum length, in some embodiments, the system is configured to determine an extended ligament length, for example from one or more medical images taken from when the patient was in an extension state. In certain embodiments, the system can be configured to measure the anterior and/or posterior length of a ligament accounting for both the horizontal and vertical lengths.

In certain embodiments, the system can be configured to utilize only a measurement of an anterior longitudinal ligament (ALL) in designing one or more patient-specific cages. For example, an ALL length for a vertebral segment of interest can be used as a maximum threshold for a resulting anterior curve (AC) after implanting one or more intervertebral cages in the vertebral segment of interest. In some embodiments, in contrast to an ALL curve that follows the anterior longitudinal ligament, AC can refer to a curve that follows an anterior boundary of the vertebral column and/or that goes through one or more anterior corners of one or more vertebrae. In certain embodiments, AC may not comprise rigid angles, for example may not be elbow-shaped, as illustrated in the example x-ray image 922 of FIG. 9C. More specifically, the system can be configured to ensure that, for a vertebral segment of interest, the resulting AC length after implantation and/or simulated implantation of an intervertebral cage does not exceed about 100% of the ALL length, about 95% of the ALL length, about 90% of the ALL length, about 85% of the ALL length, about 80% of the ALL length, about 75% of the ALL length, use, about 70% of the ALL length, about 65% of the ALL length, and/or about 60% of the ALL length. In other words, one or more of the above-identified values can be used by the system as a not-to-exceed threshold for correcting the spine of a patient, for example as a system check after determining one or more parameters for one or more patients-specific cages. In certain embodiments, the system can be configured to ensure that, for a vertebral segment of interest, the resulting AC length after implantation and/or simulated implantation of an intervertebral cage does not exceed a percentage of the ALL length between two of the aforementioned values.

In certain embodiments, the system can be configured to utilize only a measurement of posterior longitudinal ligament (PLL) in designing one or more patient-specific cages. For example, a PLL length for a vertebral segment of interest can be used as a maximum threshold for a resulting posterior curve (PC) after implanting one or more intervertebral cages in the vertebral segment of interest. In some embodiments, in contrast to a PLL curve that follows the posterior longitudinal ligament, PC can refer to a curve that follows a posterior boundary of the vertebral column and/or that goes through one or more posterior corners of one or more vertebrae. In certain embodiments, PC may not comprise rigid angles, for example may not be elbow-shaped, as illustrated in the example x-ray image 922 of FIG. 9C. More specifically, the system can be configured to ensure that, for a vertebral segment of interest, the resulting PC length after implantation and/or simulated implantation of an intervertebral cage does not exceed about 100% of the PLL length, about 95% of the PLL length, about 90% of the PLL length, about 85% of the PLL length, about 80% of the PLL length, about 75% of the PLL length, use, about 70% of the PLL length, about 65% of the PLL length, and/or about 60% of the PLL length. In other words, one or more of the above-identified values can be used by the system as a not-to-exceed threshold for correcting the spine of a patient, for example as a system check after determining one or more parameters for one or more patients-specific cages. In certain embodiments, the system can be configured to ensure that, for a vertebral segment of interest, the resulting PC length after implantation and/or simulated implantation of an intervertebral cage does not exceed a percentage of the PLL length between two of the aforementioned values.

In certain embodiments, the system can be configured to utilize measurements of both the posterior longitudinal ligament (PLL) and the anterior longitudinal ligament (ALL) in designing one or more patient-specific cages. For example, PLL and ALL lengths for a vertebral segment of interest can be used as a maximum threshold(s) for a resulting posterior curve (PC) and anterior curve (AC) after implanting one or more intervertebral cages in the vertebral segment of interest. More specifically, the system can be configured to ensure that, for a vertebral segment of interest, the resulting PC and/or AC length after implantation and/or simulated implantation of an intervertebral cage does not exceed about 100% of the PLL and/or ALL length, about 95% of the PLL and/or ALL length, about 90% of the PLL and/or ALL length, about 85% of the PLL and/or ALL length, about 80% of the PLL and/or ALL length, about 75% of the PLL and/or ALL length, use, about 70% of the PLL and/or ALL length, about 65% of the PLL and/or ALL length, and/or about 60% of the PLL and/or ALL length. In other words, one or more of the above-identified values can be used by the system as a not-to-exceed threshold for correcting the spine of a patient, for example as a system check after determining one or more parameters for one or more patients-specific cages. In certain embodiments, the system can be configured to ensure that, for a vertebral segment of interest, the resulting PC and/or AC length after implantation and/or simulated implantation of an intervertebral cage does not exceed a percentage of the PLL and/or ALL length between two of the aforementioned values.

More specifically, in certain embodiments, the system can be configured to determine lengths of one or more ligaments of a patient, such as the posterior longitudinal ligament (PLL) and/or anterior longitudinal ligament (ALL), from one or more MRI images and/or x-ray images. The one or more x-ray images can be dynamic, such as flexion and/or extension x-rays. In the illustrated embodiment in FIG. 9A, the system can be configured to determine the length of a patient's PLL and/or ALL of a particular vertebral segment on one or more MRI, x-ray and/or dynamic x-ray images at block 904, although this process may be optional in certain embodiments.

In certain embodiments, from one or more MRI images, the system can be configured to obtain the length(s) of one or more ligaments, such as ALL and/or PLL, through direct measurement of the ligaments. FIG. 9B illustrates an example embodiment(s) of cage design, production, modification, and/or selection. In particular, in the example embodiment illustrated in FIG. 9B, an MRI image 920 is provided on which the system is configured to determine lengths of both the ALL and PLL. In the illustrated example, the length of the PLL of a particular vertebral segment is determined to be roughly 61.5 mm, and the length of an ALL of the same particular vertebral segment is determined to be roughly 64.3 mm.

Further, in some embodiments, from one or more x-ray images and/or dynamic x-ray images, the system can be configured to estimate and/or determine the length(s) of one or more ligaments, such as ALL and/or PLL, such as through estimating a range of motion of one vertebra against another considering one intervertebral space. For example, from an x-ray image taken when a patient is in a flexed position, the system can be configured to estimate and/or determine a PLL length for a particular vertebral segment of the patient.

As such, referring back to FIG. 9A, in certain embodiments, the system can be configured to determine and/or estimate the length of a particular patient's PLL along a particular vertebral segment on a flexion x-ray image at block 906. FIG. 9B further illustrates a flexion x-ray image 916, on which the system is configured to estimate and/or determine the length of the PLL along a particular vertebral segment. In the illustrated example, the length of the PLL along a particular vertebral segment is determined to be roughly 61.5 mm.

Referring back to FIG. 9A, in some embodiments, the system can be configured to determine and/or estimate the length of a particular patient's ALL along a particular vertebral segment on an extension x-ray image at block 908. FIG. 9B further also illustrates an extension x-ray image 918, on which the system is configured to estimate and/or determine the length of the ALL along a particular vertebral segment. In the illustrated example, the length of the ALL along a particular vertebral segment is determined to be roughly 64.3 mm.

Based at least in part on such measurements taken from one or more MRI images and/or x-ray or dynamic x-ray images, the system can further be configured to determine and/or take into account the anterior and posterior height of a cage(s), and further take into account angulation and/or positioning in certain embodiments, in designing and/or determining one or more patient-specific cages. As such, in certain embodiments, by taking into account an assessment of the length(s) of one or more ligaments, the system can ensure that a generate surgical plan does not over-distract a patient's spine.

More specifically, referring back to FIG. 9A, the system can be configured to overlay, draw, and/or allow a user to overlay and/or draw one or more anterior curves (AC) along the anterior column and/or one or more posterior curves (PC) along the posterior column on an x-ray image, such as a postural x-ray image, at block 910 for further analysis. In certain embodiments, the system can be configured to identify one or more curves along the AC and/or PC automatically and/or semi-automatically, for example without displaying and/or overlaying the same on a display.

FIG. 9C illustrates an example embodiment(s) of cage design, production, modification, and/or selection. In particular, in the example embodiment illustrated in FIG. 9C, a postural x-ray image 922 is provided on which the system is configured to simulate implanting a cage(s) with particular dimensions to a vertebral segment. In the illustrated example in particular, the system can be configured to overlay a posterior curve and/or an anterior curve. In the illustrated example, the PC is identified and/or drawn as going through the 4 posterior vertebra corner, and the AC is identified and/or drawn as going through the 4 anterior vertebra corner. In the illustrated example, the AC for a particular vertebral segment of interest is determined to be roughly 59.4 mm, and the PC for the particular vertebral segment of interest is determined to be roughly 56.5 mm.

Referring back to FIG. 9A, in some embodiments, the system can be configured to increase the posterior height (Hpost) of one or more cages until the length of PC equals the length of PLL on an x-ray image, such as a postural x-ray image, at block 912 for further analysis. As such, at block 912, in certain embodiments, the system can be configured to modify the postural x-ray image on which the AC and/or PC was drawn by increasing Hpost of a proposed cage for implantation until the length of the PC equals the length of the PLL. In certain embodiments, the system can be configured to increase Hpost of one or more cages until the length of PC equals the length of PLL automatically and/or semi-automatically, for example without displaying and/or overlaying the same on a display. In some embodiments, the system can be configured to increase Hpost of one or more cages while ensuring that the PC is shorter than or equal to or substantially equal to the PLL.

FIG. 9C further illustrates a postural x-ray image 924 on which the system is configured to increase Hpost of a proposed cage in a particular intervertebral space for implantation until the length of PC becomes equal to the length of PLL. In the illustrated example, the Hpost of a proposed cage is increased until the PC curve length and PLL length are both determined and/or estimated to be roughly 61.5 mm. Further, in the illustrated example, the length of the AC is determined to be roughly 62.1 mm, and the length of the ALL is determined to be roughly 64.3 mm.

Referring back to FIG. 9A, in some embodiments, the system can be configured to increase lordosis, while keeping the AC length shorter than or at least equal to the ALL length for a particular vertebral segment of interest at block 914. As such, at block 914, in certain embodiments, the system can be configured to further modify the postural x-ray image on which the AC and/or PC was drawn and/or on which Hpost of a proposed cage was increased, for example by increasing lordosis. In certain embodiments, the system can be configured to increase lordosis, while keeping the AC length shorter than or at least equal to the ALL length automatically and/or semi-automatically, for example without displaying and/or overlaying the same on a display.

FIG. 9C further illustrates a postural x-ray image 926 on which the system is configured to increase lordosis while keeping the AC length shorter than or at least equal to the ALL length for a particular vertebral segment of interest. In the illustrated example, the PC length and PLL length are both determined and/or estimated to be roughly 61.5 mm, as previously determined in the postural x-ray image 924. Further, in the illustrated example, by increasing lordosis in the manner described above, the AC length is determined to be roughly 64 mm, and the length of the ALL is determined to be roughly 64.3 mm. Based at least in part on the modified and/or identified PC, PLL, AC, and/or ALL, the system can be configured to determine, design, and/or estimate one or more dimensions of a patient-specific cage, such as anterior height (Hant), posterior height (Hpost), and/or lordosis, for example to maximize spinal correction results without overstretching the patient's spine. For example, in the illustrated example, it can be determined and/or estimated that a patient-specific cage should comprise a Hant of roughly 10 mm, Hpost of roughly 7 mm, and/or lordosis of about 6°.

As such, in some embodiments, when designing and/or planning patient-specific cage(s), the system can be configured to determine, estimate, and/or define the anterior and/or posterior height of one or more patient-specific cages by assessing and/or analyzing the length(s) of one or more spinal ligaments, such as ALL and/or PLL, in order to not over-distract the spine. Further, in certain embodiments, the system can also be configured to determine, estimate, and/or define angulation of one or more patient-specific cages by taking into account positioning of such one or more cages, for example on a postural x-ray or other medical image. In some embodiments, such determined one or more cage parameters, such as posterior height, anterior height, global height, length, width, angulation, or the like, can be used by the system to design, produce, and/or select, for example from a pre-existing range or inventory, one or more patient-specific cages.

In some embodiments, the system can be configured to utilize a mathematical approach in calculating and/or estimating a desired posterior height, anterior height, global height, and/or angulation of one or more patient-specific cages, without utilizing a trial-and-error type approach. For example, in certain embodiments, the system can be configured to calculate and/or estimate a posterior height of one or more patient-specific cages by subtracting a length of a PC from a length of a PLL of a particular vertebral segment of interest, such as a segment that includes two vertebrae and an intervertebral space in between. Similarly, in some embodiments, the system can be configured to calculate and/or estimate an anterior height of one or more patient-specific cages by subtracting a length of an AC from a length of an ALL of a particular vertebral segment of interest, such as a segment that includes two vertebrae and an intervertebral space in between. Further, in some embodiments, the system can be configured to take an average of the difference between PC and PLL for a particular vertebral segment of interest and the difference between AC and ALL for the particular vertebral segment to calculate and/or estimate a height or global height of one or more patient-specific cages.

Cage Planning-Anterior Approach

Figure 10A:
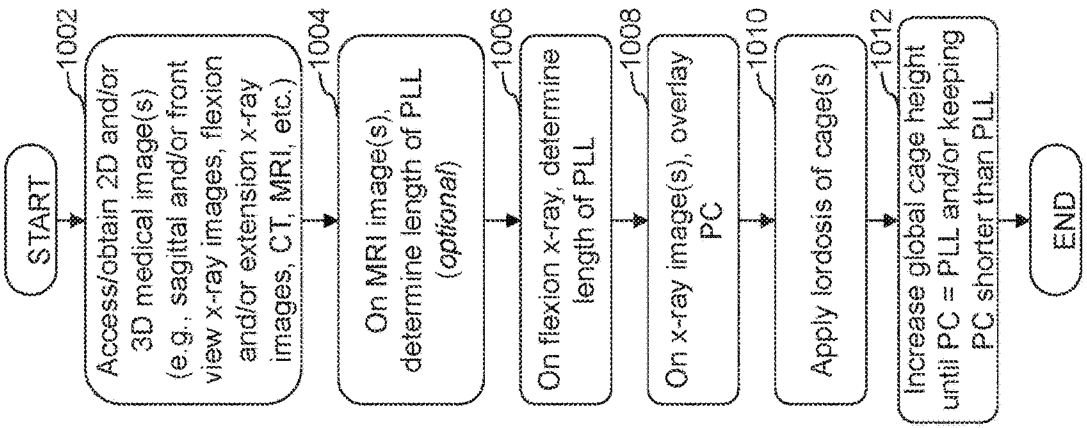
FIG. 10A is a flowchart illustrating an example embodiment(s) of cage design, production, modification, and/or selection.

In some embodiments, the system can be configured to utilize an anterior or posterior approach in measuring one or more ligament lengths and using the same in designing or determining one or more dimensions of a patient-specific cage to ensure that the patient spine is not overstretched as a result of surgery. FIG. 10A is a flowchart illustrating an example embodiment(s) of cage design, production, modification, and/or selection. In particular, as illustrated in FIG. 10A, in some embodiments, the system can be configured to utilize an anterior approach.

More specifically, in certain embodiments, the system is configured to access and/or obtain one or more two-dimensional and/or three-dimensional medical images, for example of a patient's spine, at block 1002. The one or more medical images can comprise one or more sagittal and/or frontal view x-ray images, flexion and/or extension x-ray images, CT images, MRI images, and/or medical images obtained using one or more other imaging modalities.

In some embodiments, the system can be configured to determine lengths of one or more ligaments of a patient, such as the posterior longitudinal ligament (PLL) and/or anterior longitudinal ligament (ALL), from one or more MRI images and/or x-ray images. The one or more x-ray images can be dynamic, such as flexion and/or extension x-rays. In the illustrated embodiment in FIG. 10A, the system can be configured to determine the length of a patient's PLL for a particular vertebral segment on one or more MRI, x-ray and/or dynamic x-ray images at block 1004, although this process may be optional in certain embodiments.

In certain embodiments, from one or more MRI images, the system can be configured to obtain the length(s) of one or more ligaments, such as ALL and/or PLL, through direct measurement of the ligaments. FIG. 10B illustrates an example embodiment(s) of cage design, production, modification, and/or selection. In particular, in the example embodiment illustrated in FIG. 10B, an MRI image 1016 is provided on which the system is configured to determine the length of the PLL for a vertebral segment of interest. In the illustrated example, the length of the PLL of a particular vertebral segment is determined to be roughly 61.5 mm.

In addition, in some embodiments, from one or more x-ray images and/or dynamic x-ray images, the system can be configured to estimate and/or determine the length(s) of one or more ligaments, such as ALL and/or PLL, such as through estimating a range of motion of one vertebra against another considering intervertebral spacing. For example, from a flexion x-ray image, the system can be configured to estimate and/or determine a PLL length for a particular vertebral segment of the patient.

As such, referring back to FIG. 10A, in certain embodiments, the system can be configured to determine and/or estimate the length of a particular patient's PLL along a particular vertebral segment on a flexion x-ray image at block 1006. FIG. 10B further illustrates a flexion x-ray image 1014, on which the system is configured to estimate and/or determine the length of the PLL along a particular vertebral segment. In the illustrated example, the length of the PLL along a particular vertebral segment is determined to be roughly 61.5 mm.

In some embodiments, the system can be configured to overlay, draw, and/or allow a user to overlay and/or draw one or more anterior curves (AC) along the anterior column and/or one or more posterior curves (PC) along the posterior column (PC) on an x-ray image, such as a postural x-ray image. Referring back to FIG. 10A, in certain embodiments, the system can be configured to overlay, draw, and/or allow a user to overlay and/or draw one or more posterior curves for a particular vertebral segment of interest at block 1008. In certain embodiments, the system can be configured to identify one or more posterior curves and/or anterior curves automatically and/or semi-automatically, for example without displaying and/or overlaying the same on a display.

FIG. 10C illustrates an example embodiment(s) of cage design, production, modification, and/or selection. In particular, in the example embodiment illustrated in FIG. 10C, a postural x-ray image 922 is provided on which the system is configured to simulate implanting a cage(s) with particular dimensions to a vertebral segment. In the illustrated example in particular, the system can be configured to overlay a PC. In the illustrated example, the posterior curve is identified and/or drawn as going through the 4 posterior vertebra corner. In the illustrated example, the posterior curve for a particular vertebral segment of interest is determined to be roughly 56.5 mm.

Referring back to FIG. 10A, in some embodiments, the system can be configured to apply and/or increase lordosis of a cage(s) at block 1010. As such, at block 1010, in certain embodiments, the system can be configured to further modify the postural x-ray image on which the posterior curve was drawn, for example by applying and/or increasing lordosis of a simulated cage. In certain embodiments, the system can be configured to apply and/or increase lordosis of the cage automatically and/or semi-automatically, for example without displaying and/or overlaying the same on a display.

FIG. 10C further illustrates a postural x-ray image 1020 on which the system is configured to apply and/or increase lordosis of a cage(s). In the illustrated example, by applying lordosis of a cage for a particular intervertebral space, it can be determined that the cage lordosis is roughly 9° and that the PC for a vertebral segment of interest is roughly 54.7 mm.

Referring back to FIG. 10A, in some embodiments, the system can be configured to increase the cage height, for example globally, until PC equals PLL on an x-ray image, such as a postural x-ray image, at block 1012. As such, at block 1012, in certain embodiments, the system can be configured to modify a postural x-ray image on which a PC curve was drawn and/or cage lordosis was applied, by increasing global cage height for a particular intervertebral space until the length of the PC curve equals the length of PLL for a particular vertebral segment. In certain embodiments, the system can be configured to increase global cage height until PC equals PLL automatically and/or semi-automatically, for example without displaying and/or overlaying the same on a display. In some embodiments, the system can be configured to increase global cage height while ensuring that the PC is shorter than or equal to or substantially equal to the PLL.

FIG. 10C further illustrates a postural x-ray image 1022 on which the system is configured to increase global height for a cage(s) in a particular intervertebral space(s) until PC becomes equal to PLL. In the illustrated example, Hant of the proposed cage is determined to be roughly 12 mm, and Hpost of the proposed cage is determined to be roughly 8 mm, after globally increasing the cage height until the PC length equals the PLL length for the particular vertebral segment of interest. Further, in the illustrated example, lordosis is still maintained at 9°, and the lengths of the PC and PLL are determined to be roughly 61.5 mm after globally increasing the cage height accordingly.

As such, in some embodiments, when designing and/or planning patient-specific cage(s), the system can be configured to determine, estimate, and/or define the anterior and/or posterior height of one or more patient-specific cages by assessing and/or analyzing the length of a single spinal ligament, such as either ALL or PLL, in order to not over-distract the spine. Further, in certain embodiments, the system can also be configured to determine, estimate, and/or define angulation of one or more patient-specific cages by taking into account positioning of such one or more cages, for example on a postural x-ray or other medical image. In some embodiments, such determined one or more cage parameters, such as anterior height, posterior height, global height, length, width angulation, or the like, can be used by the system to design, produce, and/or select, for example from a pre-existing range or inventory, one or more patient-specific cages.

Cage Planning-Mid-Plate Analysis

Figure 11A:
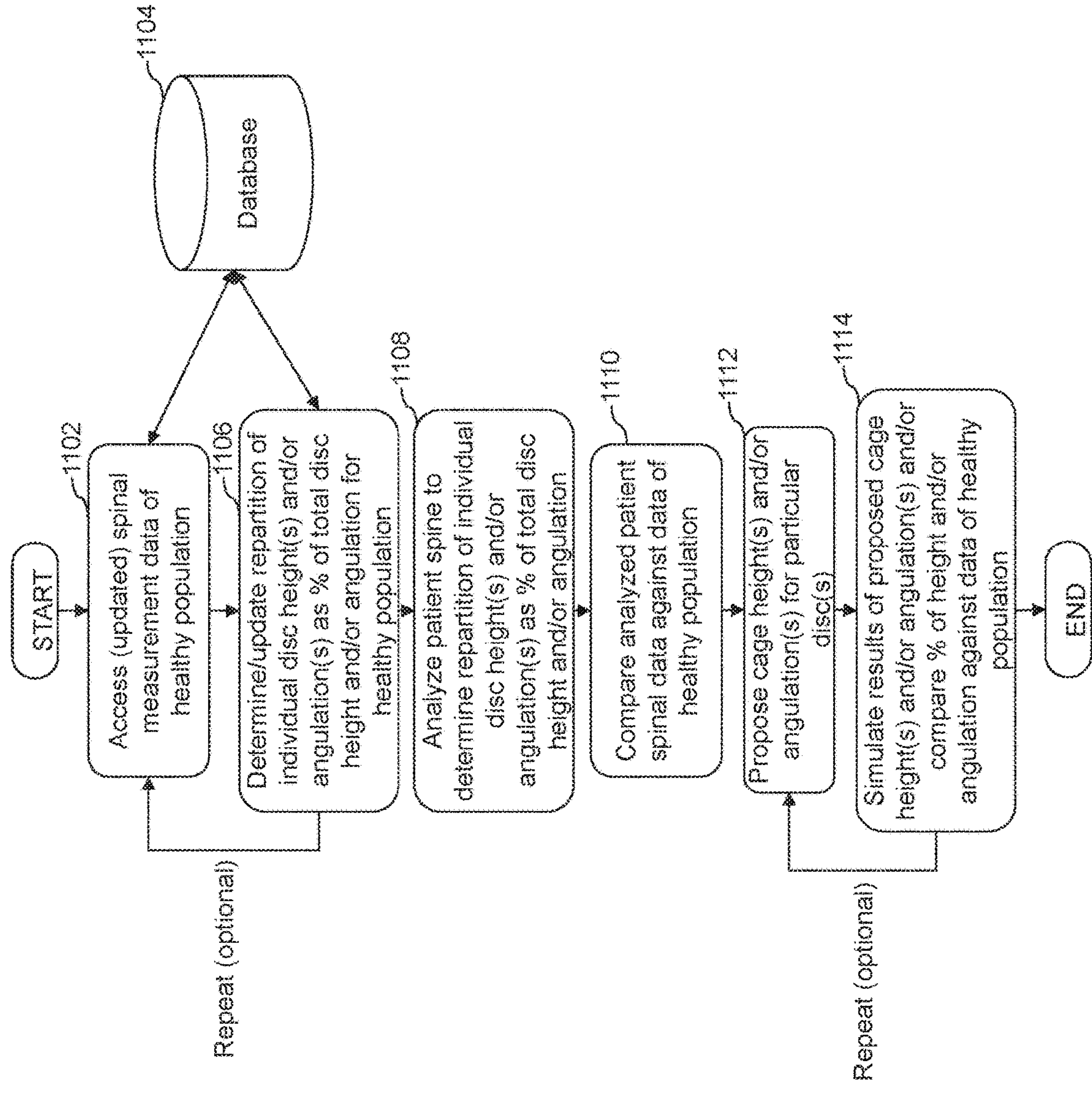
FIG. 11A is a flowchart illustrating an example embodiment(s) of cage design, production, modification, and/or selection.
Figure 11B:
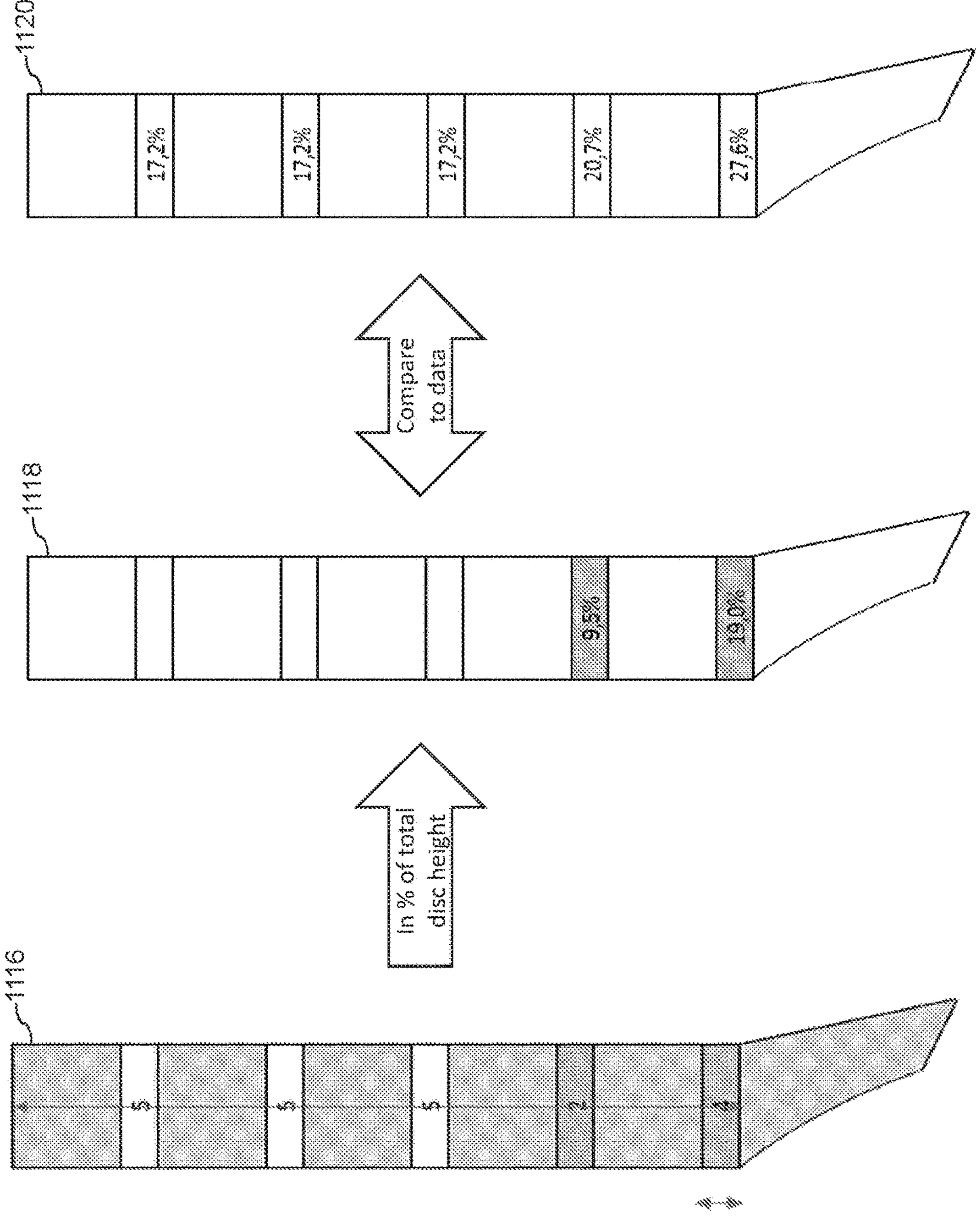
FIG. 11B is a schematic diagram illustrating an example embodiment(s) of cage design, production, modification, and/or selection.

In some embodiments, the system can be configured to analyze and/or other focus on a curve connecting the middle of one or more vertebral endplates for designing or determining one or more dimensions of a patient-specific cage, for example to ensure that the patient spine is not overstretched or over-distracted as a result of surgery. FIG. 11A is a flowchart illustrating an example embodiment(s) of cage design, production, modification, and/or selection. FIG. 11B is a schematic diagram illustrating an example embodiment(s) of cage design, production, modification, and/or selection. In particular, as illustrated in FIGS. 11A and 11B, in some embodiments, the system can be configured to utilize a mid-plate approach.

More specifically, in certain embodiments, the system can be configured to measure the height of one or more discs along a curve crossing the middle of the vertebrae endplates, for example taking into account both vertical and/or horizontal displacement. Based on the determined one or more disc height measurements, the system can be configured to calculate the mean repartition of each of the disc heights as a percentage of the total disc height, such as along the spine or portion of the spine, for example lumbar spine as illustrated in the example embodiment of FIG. 11B. In some embodiments, the system can be configured to obtain the position and/or undulation of one or more mid-plate positions along the curve. Such data can be compared to historical data from previous cases and/or to data from scientific literature for predictive planning purposes, such as to design and/or determine one or more dimensions, such as global height and/or angulation, of one or more patient-specific cages.

In some embodiments, the system can be configured to utilize a data-driven technique and/or process for cage planning. In particular, in certain embodiments, the system can be further configured to compare and/or analyze such percentage(s) against data obtained and/or pre-existing from a healthy and/or asymptomatic population. In particular, in certain embodiments, if the calculated percentage of a particular disc height for a particular patient is different compared to that of the healthy population, the system can be configured to determine that a cage(s) needs to be implanted for that disc(s). Based on such analysis, the system can further be configured to determine one or more dimensions for a patient-specific cage(s) for that disc(s) to restore an acceptable disc height, measured as a percentage of the total disc height for example. In addition, in certain embodiments, the same and/or similar technique or process can also be applied to define repartition of angulations among cages to obtain a defined global angle correction.

Referring back to FIG. 11A, in some embodiments, the system can be configured to access spinal measurement data of a healthy or asymptomatic population at block 1102. In some embodiments, the system can comprise a database 1104 that has stored data collected from a healthy and/or asymptomatic population, including data related to the height and/or angulation of one or more particular discs as a percentage of total disc height and/or as a percentage of total angulation. Such database 1104 can be internal or external to the system. Such database 1104 may be built by the system or may be imported into and/or otherwise accessed by the system.

In certain embodiments, the database 1104 can be updated continuously and/or periodically. In particular, in some embodiments, the system can be configured to determine and/or update repartition of individual disc height(s) and/or angulation(s) as a percentage of total disc height and/or angulation for a healthy population at block 1106, for example as new and/or updated healthy population spinal data is made available. This process can be repeated in some embodiments continuously and/or periodically in order to update the database 1104.

More specifically, in order to build a reference database of a healthy and/or asymptomatic population, the system can be configured to measure and/or otherwise determined individual disc height along a straight line or curve crossing the middle of the vertebrae. In addition and/or alternatively, in certain embodiments, the system can be configured to measure the disc height along an anterior and/or posterior line. In some embodiments, the system can be configured to automatically measure or determine the disc height(s) based on a medical image(s). In other embodiments, the disc height(s) are determined manually.

Based on the determined disc height and/or angulation measurement(s), the system can be configured to determine the mean repartition of all disc heights and/or angulation as a percentage(s) of the total disc height and/or angulation. By doing so, the system can be configured to obtain reference percentage(s) of repartition of disc heights for a healthy population, as illustrated in schematic 1120 of FIG. 11B. In addition, the same and/or similar technique or process can also be applied to define repartition of angulations among cages to obtain a defined global angle correction.

This reference data 1120 can subsequently be used for comparison with specific patient data to determine recommended cage(s) for that patient. In particular, referring back to FIG. 11A, the system can be configured to analyze one or more detail images of a patient, such as x-ray, MRI, CT, or the like, to determine repartition of one or more disc heights and/or angulations as a percentage of the patient's total disc height and/or angulation at block 1108.

In order to do so, referring to schematic 1116 of FIG. 11B, the system can be configured to determine the height of one or more individual discs of a patient along a mid-plate curve, for example based on one or more medical images of a vertebral segment of interest of the patient. In some embodiments, one or more disc heights of a particular patient can be measured or obtained pre-operation. In certain embodiments, the system can be configured to obtain measurement of a patient's lumbar disc height, automatically or manually from one or more medical images, by level and/or total. Based on such measurement, the system can be configured to determine that a particular patient may need a cage replacement for one or more discs for example if there is a large discrepancy compared to data from a healthy population. In the illustrated embodiment 1116, the system may determine that a patient may need cage replacements at L4L5 and/or L5S1.

As discussed, in certain embodiments, the system can be configured to use the measured or determined individual disc heights and/or angulations to calculate percentage(s) of each disc height and/or angulation compared to the total sum of disc heights and/or angulations at block 1108. For example, in the example embodiment illustrated in FIG. 11B, and in particular in schematic 1118, the height of L4L5 and L5S1 as a percentage(s) of the total lumbar spine disc height can be determined to be roughly 9.5% and 19.0%.

In some embodiments, the system can further be configured to compare and/or analyze such percentage(s) against the data obtained from a healthy population at block 1110. For example, in the example illustrated in FIG. 11B and in particular in schematic 1120, the disc height of L4L5 and L5S1 as a percentage(s) of the total lumbar spine disc height can correspond to 20.7% and 27.6% for a healthy population.

If the calculated percentage of a particular disc height for a particular patient is too low compared to the healthy population, the system can be configured to determine that cage(s) must be implanted for that disc to restore an acceptable disc height. In certain embodiments, if a particular disc height of a particular patient is below a predetermined threshold value when compared to the healthy population, the system can be configured to recommend cage implantation of a certain height or range of heights. For example, in some embodiments, the system can be configured propose one or more cage heights, such as anterior and/or posterior cage heights, for replacing a particular disc at block 1112 of FIG. 11A.

In some embodiments, the system can be further configured to simulate results of one or more proposed cage heights and/or angulations and/or compare the simulated results in terms of percentage of one or more cage heights and/or angulations against data collected from a healthy population at block 1114. Based on such simulation results, the system can be configured to generate modified proposed height(s), angulation(s), and/or other dimensions for one or more cages. As such, in some embodiments, the system can further be configured to compare and/or analyze such percentages against the database of an asymptomatic population. Based on such comparison, if the difference between such values is below a predetermined threshold, the system can be configured to accept or finalize the cage planning proposal. However, if the difference is above a certain predetermined threshold, the system can be configured to reject the cage planning proposal and continue to refine the proposal, for example by increasing and/or decreasing one or more heights, angulations, or other dimensions of a cage. As such, the system, in some embodiments, can be configured to apply an iterative process or technique. In some embodiments, such determined one or more cage parameters, such as posterior height, anterior height, global height, length, width, angulation, or the like, can be used by the system to design, produce, and/or select, for example from a pre-existing range or inventory, one or more patient-specific cages.

Screw Planning

As discussed herein, in certain embodiments, the system can be configured to design, produce, modify, and/or provide guidance for selection of one or more patient-specific screws. This can be advantageous by substantially reducing costs by decreasing the inventory of screws that need to be manufactured and/or kept in stock. Related costs can even further be reduced due to reduced sterilization costs. An additional advantage can be decreased surgery time and simplification of surgical procedures for the surgeon and staff as fewer screws, cages, and/or sets thereof are provided as a personalized caddie for each surgery, thereby increasing efficiency of the surgery.

For example, as opposed to providing every single available screw or sets of screws, which can amount to 400 or 500 or more screws for a typical deformity tray, some embodiments can allow provision of only about 10 screws, about 20 screws, about 30 screws, about 40 screws, about 50 screws, about 60 screws, about 70 screws, about 80 screws, about 90 screws, about 100 screws, about 110 screws, about 120 screws, about 130 screws, about 140 screws, about 150 screws, about 160 screws, about 170 screws, about 180 screws, about 190 screws, about 200 screws, and/or a number of screws within a range defined by two of the aforementioned values for an operation that generally requires only about 2 to 60 screws for example. As a non-limiting example, in some embodiments, for a 5 level surgery, the system can be configured to provide selection and/or recommendation to include a maximum of 72 screws with particular dimensions in a personalized caddie.

As such, in some embodiments, the system is configured to assess one or more adequate dimensions to design patient-specific screws and/or other implants from analysis of and/or measurements obtained from one or more medical images, such as two-dimensional x-ray images and/or MRI sagittal slice(s). In certain embodiments, the system can be configured to combine one or more measurements obtained from one or more medical images with literature and/or data driven additions to obtain sufficient accuracy and/or precision to substantially define patient-specific screw designs and/or one or more dimensions thereof.

Figure 12A:
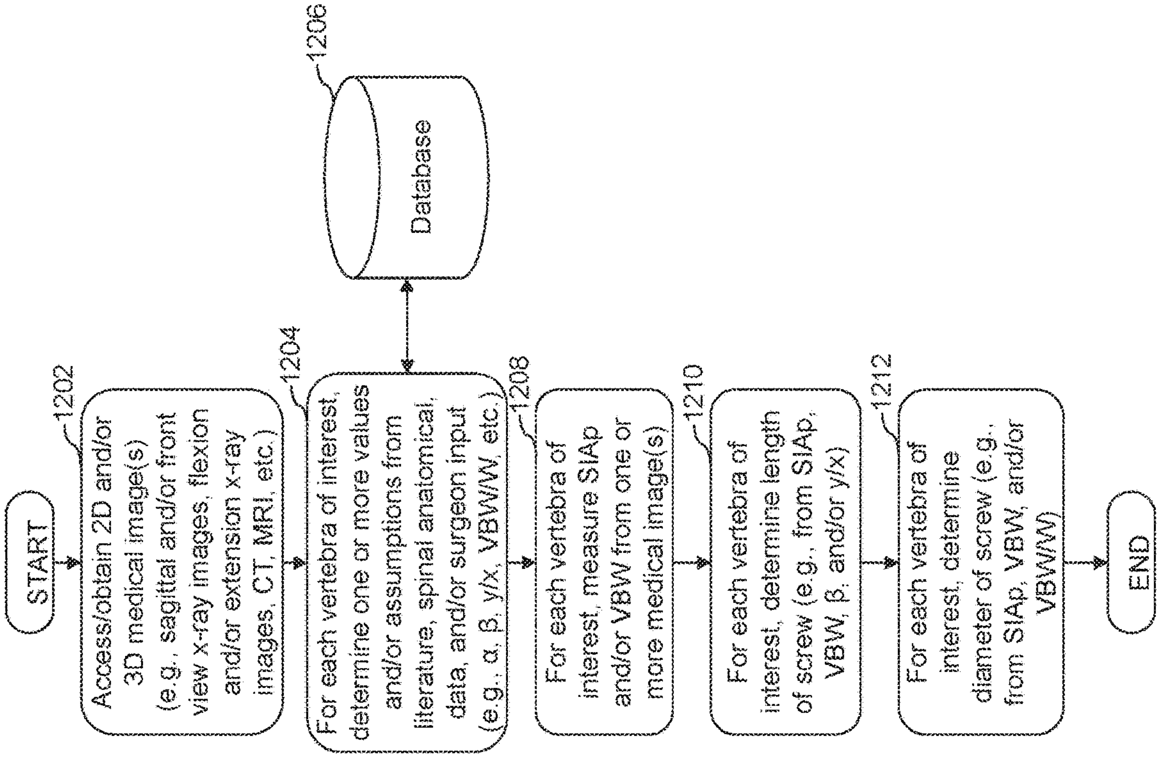
FIG. 12A is a flowchart illustrating an example embodiment(s) of screw design, production, modification, and/or selection.

FIG. 12A is a flowchart illustrating an example embodiment(s) of screw design, production, modification, and/or selection. In particular, as illustrated in FIG. 12A, the system, in some embodiments, can be configured to design and/or determine one or more dimensions of a patient-specific screw(s) for insertion into a particular vertebra, which can be used to design, produce, modify, and/or select one or more patient-specific screws.

In certain embodiments, the system is configured to access and/or obtain one or more two-dimensional and/or three-dimensional medical images, for example of a patient's spine, at block 1202. The one or more medical images can comprise one or more sagittal and/or frontal view x-ray images, flexion and/or extension x-ray images, CT images, MRI images, and/or medical images obtained using one or more other imaging modalities. As such, in some embodiments, screw selection and/or design can be based on three-dimensional imaging scan data, such as a CT scan. Based on a CT scan, the system can be configured slice a vertebra to which a screw will be inserted and determine precise measurements of each required screw, such as the length and/or diameter of the screw. However, to do so, three-dimensional multi-planar reconstruction (MPR) may be required, which can be time-consuming. Also, a CT scan can be necessary, which is not a routine image.

In some embodiments, patient-specific screw design, selection, and/or recommendation can be based on three-dimensional medical images and/or two-dimensional medical images, as described above in relation to FIG. 2. For example, in some embodiments, the system can be configured to utilize one or more sagittal x-ray images only to obtain certain measurements. In certain embodiments, the system can be configured to utilize a sagittal x-ray image and a frontal x-ray image to obtain a composite three-dimensional image as described above to obtain more accurate screw length and/or diameter estimates. In some embodiments, the system can be configured to utilize a full three-dimensional image to obtain certain measurements.

In certain embodiments, the system can be configured to utilize one or more two-dimensional x-ray and/or MRI image data. X-ray images can be routine and widely available. In some embodiments, the system can be configured to provide one or more precise specifications and/or dimensions of one or more patient-specific screws based on analysis of one or more two-dimensional x-ray images and/or MRI slices. In certain embodiments, the system can be configured to combine one or more measurements obtained from one or more two-dimensional x-ray images and/or MRI slices with one or more measurements and/or other features from the literature and/or other data to obtain increased accuracy and/or precision, for example in order to at least substantially decrease the total number of screws that may be required for a particular surgery.

More specifically, in some embodiments, the system can be configured to utilize one or more features derived from spinal anatomical data, scientific/medical literature, surgeon preference or other input, and/or other data in order to obtain certain values and/or assumptions in determining one or more parameters or variables for designing patient-specific screws. Referring back to FIG. 12A, in some embodiments, the system can be configured to determine and/or obtain one or more values and/or assumptions at block 1204 based at least in part on scientific or medical literature, spinal anatomical data, and/or surgeon preference or input that can be stored in a database 1206. The one or more values and/or assumptions can be specific for each vertebra of interest. For example, in certain embodiments, the system can be configured to obtain one or more values and/or assumptions regarding angulation of a screw in a sagittal plane in reference to an endplate of the vertebra in which the screw is inserted in (α), angle between vertebra axis and pedicle axis on a transverse plane (β) which can be level-specific, ratio between screw length and screw insertion axis length (y/x), and/or ratio between vertebral body width (VBW) and minimum pedicle width (W) which can be level-specific.

FIG. 12B is a schematic diagram illustrating certain aspect(s) of an example embodiment(s) of screw design, production, modification, and/or selection. In particular, as illustrated in schematic 1214 of FIG. 12B, in some embodiments, the system can be configured to assume and/or obtain angulation a of an implanted screw in reference to an endplate in which the screw is inserted. For example, in some embodiments, it can be assumed that an implanted screw will be parallel to an endplate based on scientific literature and/or spinal anatomical data. In other words, angulation a of a screw in a sagittal plane can be assumed to be equal or substantially equal to the considered vertebra (and upper vertebral endplate) angulation. As such, in certain embodiments, this angulation a can be assumed to be zero, for example based on scientific literature and/or spinal anatomical data. In some embodiments, the system can be configured to assign any other angle value to angulation a, for example based on surgeon habits and/or preferences and may be surgeon-specific.

Further, as illustrated in schematic 1216, in certain embodiments, the system can be configured to obtain and/or assume an angle β between the vertebra axis and the pedicle axis (in transverse plane) at each level, for example from scientific literature and/or spinal anatomical data. This angle β between the vertebra axis and the pedicle axis (in transverse plane) can be level-specific. In some embodiments, the system can be configured to assign any other angle value to angle β, for example based on surgeon habits and/or preferences and may be surgeon-specific.

Similarly, as illustrated in schematic 1218, in some embodiments, the system can be configured to obtain and/or assume a ratio (y/x) between screw length and screw insertion axis length (SIA), for example based on scientific literature and/or spinal anatomical data. For example, in some embodiments, the system can be configured to assume 70% penetration of the vertebral body by a screw for optimal bone screw anchorage, as may be suggested by scientific literature. In certain embodiments, SIA may be surgeon-specific and/or may depend on a preference and/or surgical goal of a particular patient. Surgeon preferences can also be considered for screw orientation in a transverse plane (in line with pedicle, convergent or even divergent). Based on a data-driven process, scientific literature, and/or surgeon preference, the system can be configured to assume SIA to be about 10%, about 20%, about 30%, about 40%, about 50%, about 60%, about 70%, about 80%, about 90%, and/or within a range defined by two of the aforementioned values.

Further, as illustrated in schematic 1220, in certain embodiments, the system can be configured to obtain and/or assume a ratio between vertebral body width (VBW) and minimum pedicle width (W), for example from scientific literature and/or spinal anatomical data. The ratio between VBW and W can be level-specific. As such, the system can be configured to obtain a ratio between VBW and W for each level vertebra in certain embodiments. In some embodiments, the system can be configured to assign any other angle value to VBW, W, and/or a ratio thereof, for example based on surgeon habits and/or preferences and may be surgeon-specific.

Referring back to FIG. 12A, in some embodiments, the system can be configured to measure one or more parameters from the one or medical images at block 1208. In particular, the system can be configured to measure from the one or more medical images, one or more of a screw insertion axis (SIA) projected length on the sagittal plane (SIAp) and/or vertebral body width (VBW) for each vertebra of interest. In particular, in certain embodiments, SIAp and/or VBW measurement(s) can be obtained from a sagittal x-ray image and/or an MRI slice for each vertebra of interest. In certain embodiments, the length of an endplate can be measured from a sagittal x-ray image. In some embodiments, the length from a pedicle entry to an anterior wall of the vertebra can be obtained. In certain embodiments, both endplate length and length from a pedicle entry to an anterior wall of the vertebra can be measured for each vertebra of interest.

In certain embodiments, based on such assumptions and data from scientific literature and/or surgeon input and further based on SIAp and/or VBW, the system can be configured to determine and/or estimate the length and/or diameter of each patient-specific screw. In particular, in some embodiments, the system at block 1210 can be configured to determine the length(s) of each screw(s) for each level(s) of interest based in part on SIAp, VBW, angle between vertebrae axis and pedicle axis, and/or screw penetration ratio. In certain embodiments, the system at block 1212 can be configured to determine the diameter(s) of each screw(s) for each level(s) of interest based in part on SIAp, VBW, and/or ratio between VBW and a minimum pedicle width (W). In some embodiments, the VBW to W ratio can be assumed from the literature to be about 10%, about 20%, about 30%, about 40%, about 50%, about 60%, about 70%, about 80%, about 90%, and/or within a range defined by two of the aforementioned values.

In certain embodiments, the system can be configured to determine a length between a point of insertion of a screw on a vertebra and an opposing outer boundary of the vertebra or endplate thereof and use the same or a percentage of such length as a not-to-exceed value for a desired length of a screw that is determined by the system for a particular vertebra, for example as a system check after determining one or more parameters for one or more patients-specific screws. For example, the system can be configured to ensure that, for a particular vertebra of interest, the length of a screw to be implanted in that vertebra, as determined by the system, does not exceed about 100%, about 95%, about 90%, about 85%, about 80%, about 75%, about 70%, about 65%, about 60%, and/or a percentage in between two of the aforementioned values of a determined length between a point of insertion of a screw on that vertebra and an opposing outer boundary of the vertebra or endplate thereof. In some embodiments, the system can be configured to determine a minimum pedicle width (W) and utilize the same or a percentage thereof as a not-to-exceed value for a desired width of a screw that is determined by the system for a particular vertebra, for example as a system check after determining one or more parameters for one or more patients-specific screws. For example, the system can be configured to ensure that, for a particular vertebra of interest, the width of a screw to be implanted in that vertebra, as determined by the system, does not exceed about 100%, about 95%, about 90%, about 85%, about 80%, about 75%, about 70%, about 65%, about 60%, and/or a percentage in between two of the aforementioned values of a determined minimum pedicle width (W).

As such, in some embodiments, the system can be configured to determine a desired diameter and/or length of a screw(s) to obtain sufficient anchorage for one or more vertebra of interest and/or every vertebra or a subset thereof for a specific patient and/or a specific vertebra thereof. Screw design, recommendation, and/or selection of certain screws prior to surgery can be based on any one of the patient-specific features and/or analysis discussed above. In certain embodiments, the system can be further configured to design, recommend, plan, and/or select one or more patient-specific screws (and/or a material, type, length, and/or width thereof) based on a determine bone quality, bone density, age of patient, and/or gender of patient. In certain embodiments, the diameter of a patient-specific screw, as determined by the system, can range from about 3.5 mm to about 10.5 mm. In some embodiments, such determined one or more screw parameters, such as length, diameter, material, anchorage, or the like, can be used by the system to design, produce, and/or select, for example from a pre-existing range or inventory, one or more patient-specific screws.

Intraoperative Tracking Sensors

Generally speaking, certain intraoperative imaging such as fluoroscopy and/or CT scans can be used for intraoperative assessment of spinal curvatures and/or correction thereof. However, such processes generally only provide instantaneous vision/assessment of spinal curvatures. As such, it can be advantageous to allow live-tracking of spinal curvatures/angulations to provide substantial assistance to the surgeon, thereby further allowing the surgeon to make further corrections to the spine as may be necessary under live control. At the same time, certain live-tracking devices, such as those that may be based on optoelectronic passive sensors, may disturb the surgeon's workflow as many additional steps may be required compared to usual surgery.

Accordingly, in some embodiments described herein, systems, device, and methods are provided that allow for intraoperative monitoring. In particular, in certain embodiments, the system can be configured to track a surgeon's performance in real-time, near real-time, and/or in substantially real-time and further compare the same to the preoperative planning, while adding only a minor footprint on surgery workflow.

In some embodiments, the system can allow a surgeon to manipulate a patient's spine and follow one or more positions and/or one or more orientations of one or more sensors that are attached to one or more vertebrae. One or more sensors attached to one or more vertebrae can be configured to provide tracking data relating to one or more positions and/or orientations of the vertebra the sensor is attached to. As such, in certain embodiments, based on such tracking data and/or guidance data derived therefrom, the surgeon can then manipulate the patient's spine until one or more sensor readings show that the positioning of the spine is optimal, desirable, and/or matches a predetermined plan.

In some embodiments, intraoperative imaging processes or techniques, such as fluoroscopy and/or CT scans can be used for intraoperative imaging. For example, in certain embodiments, intraoperative fluoroscopy can be used to assess the position of screws regarding anatomy structures to provide intraoperative tracking. In certain embodiments, one or more sensors can be used in conjunction with one or more infrared cameras and/or electromagnetic detection. In some embodiments, the position(s) and/or orientation(s) of the one or more sensors and/or bones can be identified by use of active sensors. In certain embodiments, one or more passive sensors can also be used.

In some embodiments, the system can be configured to identify the position(s) and/or orientation(s) of one or more pedicle screws, and in turn one or more bones and/or vertebrae to which the one or more pedicle screws are attached thereto, by use of one or more active sensors. As such, in certain embodiments, the system is configured to utilize one or more active sensors, without the need for any receivers to interpret the position, orientation, and/or angulation of one or more sensors on a common axes system. In other words, in some embodiment, the whole intraoperative tracking system and/or device may include only one or more sensors and one or more computer devices or systems treating the signal of the one or more sensors and displaying one or more measurements obtained therefrom.

In some embodiments, a sensor, as the term is used herein, can comprise a power source, such as a battery, a wireless transmitter, and one or more active and/or passive sensors for real-time tracking. In certain embodiments, the one or more sensors can comprise one or more accelerometers and/or one or more gyroscopes to provide one or more inertial measurement units, such as in 6 degrees of freedom (DOF) and/or 9 DOF. In some embodiments, the system can comprise one or more active sensors which are configured to be an inertial measurement unit in 6 DOF and/or 9 DOF. In some embodiments in which the system is configured to utilize one or more passive sensors, visual tracking can be utilized to provide intraoperative tracking in real-time, near real-time, and/or in substantially real-time. In other embodiments in which only active sensors are used, the system can be configured not to rely on visual tracking. Rather, the system can utilize wireless transmission of motion data for intraoperative tracking in real-time, near real-time, and/or in substantially real-time.

In certain embodiments, the system can be configured to determine relative orientation and/or position of two or more sensors attached to a patient's spine to measure and/or calculate spinal curvature, for example by interpreting independent sensor data. In particular, in some embodiments, the system can be configured to interpret independent sensor data obtained from two or more sensors, using the gravity force vector as a common reference. In certain embodiments, two of the three axes of each central units can be assumed or considered to be on a plane parallel or substantially parallel with a determinate angle to the sagittal plane of the patient lying on the operating table. In other words, in certain embodiments, the position and/or orientation of two or more sensors can be configured such that two of the three axes of position data to be collected by each sensor are on or assumed to be on a plane parallel or substantially parallel to the sagittal plane of a patient lying on the operating table. As such, the right positioning of the inertial unit can be mechanically obtained through a sensor/implant interface in some embodiments.

Figure 13A:
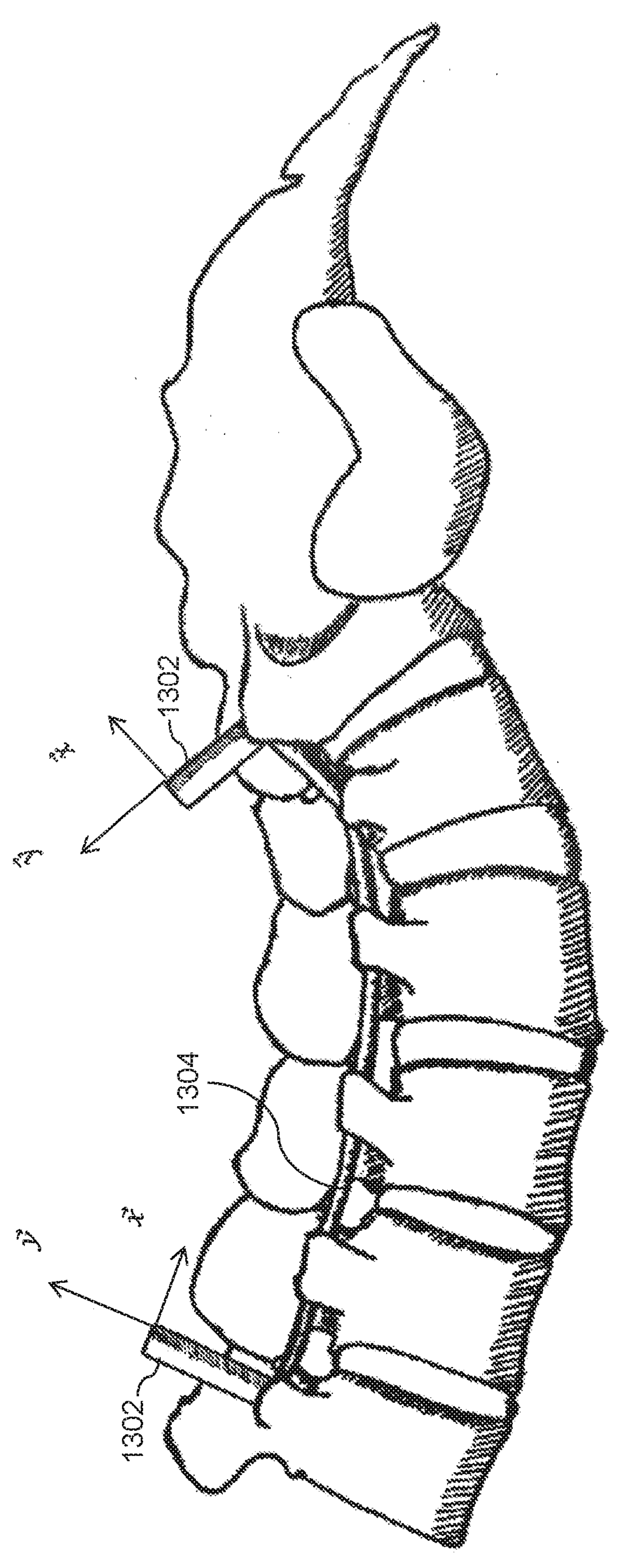
FIG. 13A is a schematic illustrating an example embodiment(s) of intraoperative tracking.
Figures 13B, 13C, 13D, 13E:
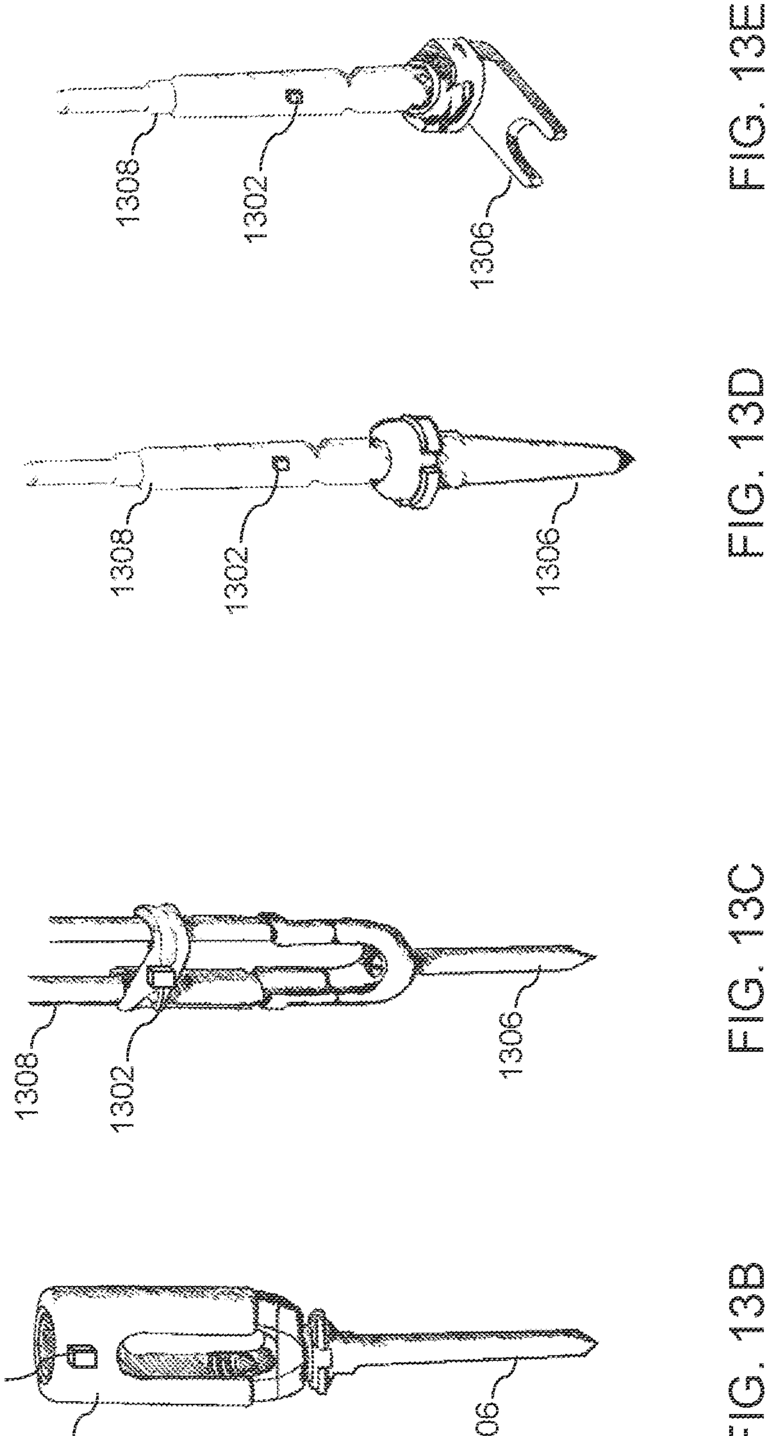
FIGS. 13B-13G illustrate example embodiments of screws and/or sensors that can be used for intraoperative tracking.

In some embodiments, one or more sensors can be attached to every vertebra, for example through one or more interfaces provided via one or more implants/screws and/or directly to bone structures. In certain embodiments, one or more sensors can be attached to only a portion of the vertebrae. As such, in some embodiments, one or more sensors may be attached to only a subset of vertebra that can provide valuable position and/or angular data of the spine. FIG. 13A is a schematic illustrating an example embodiment(s) of intraoperative tracking. As illustrated in FIG. 13A, in some embodiments, one or more sensors 1302 may be attached only to certain vertebrae, for example to which a spinal road 1304 is implanted. For example, in certain embodiments, one or more sensors may be attached to S1, L1 and T4 vertebrae to assess L1-S1 lordosis and/or T4-T12 kyphosis.

In some embodiments in which one or more sensors are directly linked and/or attached to one or more screws, the system can be configured to assume that angulation of a screw in a sagittal plane is substantially equal to the vertebra (or superior endplate) angulation. Optionally, in certain embodiments, intraoperative fluoroscopic images can be used to assess the position of screws regarding anatomic structures, such as vertebral endplates, in the sagittal plane, as well as other planes in some embodiments.

Figure 13G:
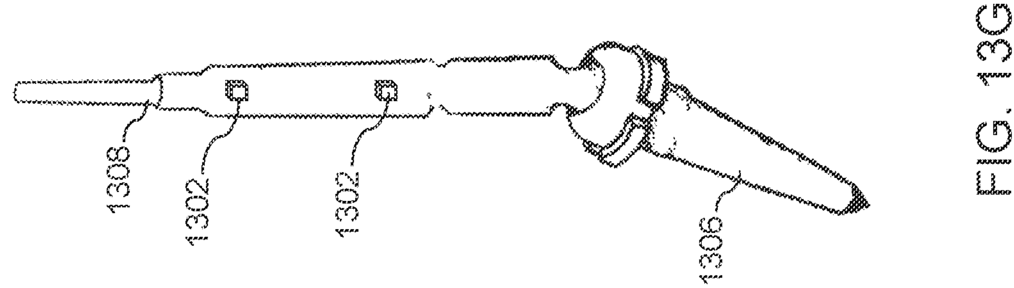
Figure 13F:
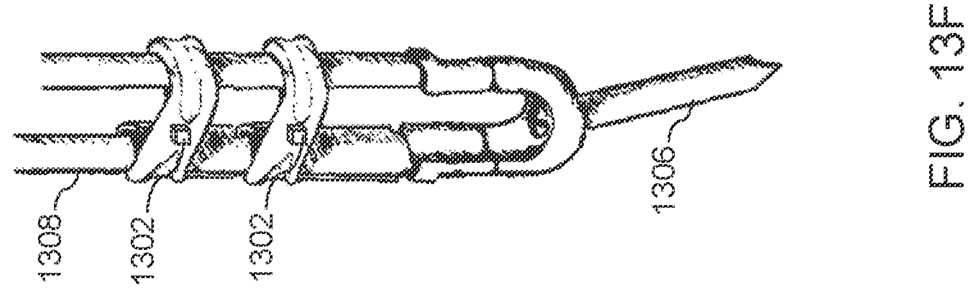

FIGS. 13B-13G illustrate example embodiments of screws and/or sensors that can be used for intraoperative tracking. In some embodiments, one or more screws and/or other implants can be mono-axial and/or poly-axial. FIGS. 13B-13E illustrate example embodiments of mono-axial screws, while FIGS. 13F-G illustrate example embodiments of poly-axial screws.

In certain embodiments where one or more mono-axial screws are used, the system can be configured to follow the position and/or angle of every implanted screw, thereby following the position of a vertebrae based on the screw position. A mono-axial screw may comprise only one sensor 1302, based on the assumption that every movement of the screw is due to rigid movement of the vertebrae. In certain embodiments, a mono-axial screw may comprise one or more sensors 1302.

In some embodiments, a poly-axial screw can comprise one or more sensors and/or two or more sensors 1302, for example to be able to determine if a particular motion or movement is due to rigid movement of the vertebrae itself or at least partially or wholly because of motion between the different portions of the screws, such as in and outside the vertebra, or non-rigid movement. In some embodiments, the system can be configured to determine that a particular movement is rigid movement if there is correlation between the two or more sensor readings.

In some embodiments, a top portion of a screw and/or other implant can comprise one or more active and/or passive sensors. In certain embodiments, the top portion of a screw and/or other implant can also comprise a power source, such as a battery, and/or wireless transmitter, as well as one or active and/or passive sensors. In some embodiments, the top portion can be broken off later during surgery and not implanted. The sensor 1302, or at least one or more portions thereof, can then be reused, thrown away, and/or repurposed for future use. For example, in the illustrated example embodiments in FIGS. 13B-13E, the system can be configured to utilize one or more monoaxial screws, polyaxial screws, and/or other implants, each comprising an attaching portion 1306 and a top portion 1308. The top portion 1308 can comprise a single sensor 1302 for certain screws. Similarly, in the illustrated example embodiments in FIGS. 13F-G, the system can be configured to utilize one or more poly-axial screws and/or other implants, each comprising an attaching portion 1306 and a top portion 1308. As illustrated, in certain embodiments, the top portion 1308 can comprise two or more sensors 1302 each for certain screws.

In some embodiments, an intraoperative tracking system or device can require at least two or more screws to be attached to the vertebrae, wherein each of the two or more screws comprises at least one sensor. In certain embodiments, an intraoperative tracking system or device can require at least one, two, three, four, five, six, seven, eight, nine, and/or ten screws comprising one or more sensors to be attached to the vertebrae. In some embodiments, an intraoperative tracking system or device can require a certain range of numbers of screws comprising at least one sensor, wherein the range is defined by two of the aforementioned values.

In certain embodiments, once one, two, three, four, and/or more screws comprising at least one sensor are attached to the vertebrae, the system can be configured to obtain one or more sensor readings of the current position(s), orientation(s), and/or angle(s) of one or more screws and thus vertebrae. Based on the reading(s) from the one or more sensors and/or guidance generated therefrom, a surgeon can further manipulate the patient's spine as desired. For example, in some embodiments, the intraoperative tracking system and/or device can be configured to continuously and/or periodically provide updated tracking data and/or analysis therefrom, such that the surgeon can manipulate the patient's spine until one or more sensor readings show that one or more positioning and/or orientation of the spine are optimal and/or matches or substantially matches a predetermined plan.

In some embodiments, the system can also be configured to provide tips, guidance, and/or suggestions to the surgeon to manipulate the spine in a certain manner and/or direction, for example to reach and/or more closely follow the predetermined plan. In some embodiments, a surgeon can implant the spinal rod through the one, two, three, four, and/or more screws once an optimal or desired configuration of the spine is obtained. In certain embodiments, after rod implantation, the top portion of screw that comprises the one or more sensors can be broken off.

In certain embodiments, the one or more sensors are not provided as part of screws; rather one or more surgical tools, which can eventually be used to attach screws to the vertebrae, can comprise one or more sensors. For example, a screwdriver, nut driver, or other specific or usual surgical tool configured to attach a pedicle screw, anchorage, and/or other implant can comprise one or more active and/or passive sensors for intraoperative tracking purposes. In some embodiments, an intraoperative tracking system can require at least one, two, three, four, five, six, seven, eight, nine, and/or ten surgical tools to comprise one or more sensors. In certain embodiments, an intraoperative tracking system or device can require a certain range of numbers of tools to comprise at least one sensor, wherein the range is defined by two of the aforementioned values.

In some embodiments, a surgical tool comprising one or more sensors for intraoperative tracking purposes can comprise a button or other signaling mechanism that measures and/or stores the current position and/or orientation data of the surgical tool, for example in 6 DOF and/or 9 DOF. As such, in certain embodiments, once a screw, anchorage, or other implant is put in place, such as attached to a vertebra, using such surgical tool, the surgeon or other medical personnel can activate the sensor in the tool, thereby detecting and/or providing orientation and/or position data at that time. As such, in some embodiments, the intraoperative tracking system can be configured to provide data frozen in time rather than providing real-time tracking data.

Figure 14E:
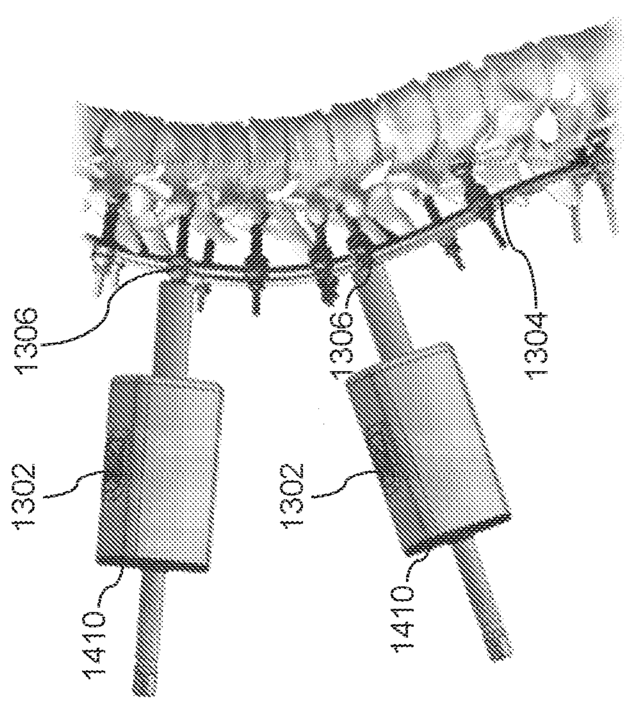

FIGS. 14A-14E illustrate example embodiments of tools and/or sensors that can be used for intraoperative tracking. As illustrated in FIG. 14A, in some embodiments, a screwdriver 1400 can comprise one or more sensors 1302 and/or other electronic components for intraoperative tracking. In certain embodiments, as illustrated in the example embodiment of FIG. 14A, the one or more sensors 1302 and/or other electronic components can be located in a shaft 1402 of a screwdriver. In some embodiments, as illustrated in the example embodiment of FIG. 14B, the one or more sensors 1302 and/or other electronic components can be located in a handle 1404 of a screwdriver. Further, as illustrated in the example embodiment of FIG. 14C, a nut driver 1406 can comprise one or more sensor 1302, for example in the shaft 1408 and/or in the handle.

Figure 14D:
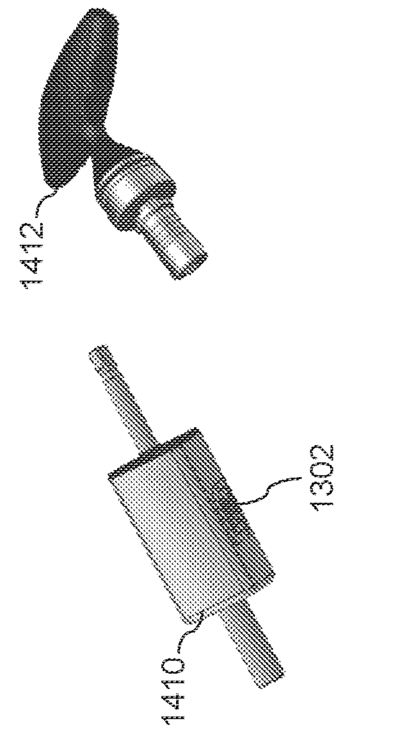

In some embodiments, as illustrated in the example embodiments of FIGS. 14D and 14E, an additional housing structure 1410 configured to be coupled to a screw 1306, nut, anchorage, and/or other implant can comprise one or more active and/or passive sensors 1302. In certain embodiments, the additional housing structure 1410 can also comprise a power source, such as a battery, and/or wireless transmitter, as well as one or active and/or passive sensors 1302. In some embodiments, the additional housing structure 1410 can be configured to be used and/or coupled to a removable handle 1412. The additional housing structure 1410 can be attached to a screw 1306 and/or other pedicle anchorage or implant. As the spine is adjusted during surgery, the one or more sensors 1302 can provide data relating to the orientation and/or position of the screw 1306 as the additional housing structure 1410 is still attached to the screw 1306. After the spine is adjusted to an acceptable level, a spinal rod 1304 can be inserted, and the screw 1306 and/or other pedicle anchorage or implant can be affixed to the vertebrae using the removable handle 1412, after which, the additional housing structure 1410 can then be removed. In some embodiments, the additional housing structure 1410 can provide additional space or volume for the one or more sensors, power source, and/or wireless transmitter to be placed.

Predictive Modeling

In some embodiments, the system is configured to generate one or more predictive models or algorithms for surgical operations. In certain embodiments, the one or more predictive models and/or algorithms are configured to predict one or more surgical parameters and/or variables that may result from a surgical procedure, for example of the spine. In some embodiments, the predictive models and/or algorithms are configured to generate a surgical plan for achieving desired surgical outcomes. For example, the systems disclosed herein can be configured to access preoperative patient input data and generate a surgical plan for implanting a spinal rod into the patient where the generated surgical plan that is personalized for the patient is configured to generate an optimal post-surgical spine curvature for the particular patient.

When a patient undergoes surgery by a doctor, the surgical outcomes can be generally determined based on the surgeon's estimations and prior surgical experience. For example, when a spinal rod is implanted into a patient, the surgeon can analyze the patient's body and other characteristics. Based on these observations, the surgeon can provide a general estimate and/or select certain surgical parameters that the surgeon believes will result in a better spinal curvature for the patient post-surgery. However, in reality, the surgeon's estimations and selected surgical parameters may not result in the most desired or optimal surgical outcomes.

For example, when performing a spinal surgery for improving a patient's spinal curvature, the doctor can select a curvature for the spinal rod to be implanted into a patient. The rod curvature selection can be determined and/or estimated by the surgeon based on the doctor's observations of the patient, and such determinations and estimations may result in the patient having a spine curvature that is less than optimal after the surgery. Accordingly, it can be beneficial for a surgeon and/or a patient to have a system that could predict surgical parameters post-surgery based on pre-operative patient characteristics. For example, it would be helpful to determine, before performing spinal surgery, one or more optimal surgical parameters that should be utilized in a surgical plan in order to achieve the optimal spinal curvature post-surgery for a particular patient with certain characteristics. Certain systems, methods, and devices disclosed herein are configured to address the foregoing issues.

In particular, in some embodiments, the system can be configured to access pre-operative patient characteristics and input one or more such variables into a predictive algorithm. In certain embodiments, the system can be configured to utilize the predictive algorithm to generate one or more surgical plans having one or more specific surgical parameters that are predicted to generate an optimal post-surgical outcome for the patient. For example, the system can be configured to receive one or more patient characteristics, such as preoperative spinal curvatures and angles, patient age, genetic mapping or genetic conditions, and/or other variables. In particular, the existence of certain genes may have a correlation with a particular condition, such as scoliosis, and/or surgical outcome. The system can be configured to utilize such patient characteristics and/or variables for inputting into a predictive algorithm. The system can be configured to output based on the predictive algorithm specific surgical parameters, such as the optimal spinal rod curvature and/or instrumentation positions and/or other variables for achieving the optimal spinal curvature post-surgery for the patient.

In some embodiments, the system is configured to utilize the one or more predictive algorithms to generate a predictive post-surgical outcome. For example, the system can be configured to access one or more patient characteristics as well as surgical parameters that a surgeon intends to use in a surgical plan. In some embodiments, the system can be configured to utilize the predictive algorithm to determine the post-surgical outcome that will result from the surgical parameters associated with the surgical plan. For example, the system can be configured to access patient characteristics, such as preoperative spinal curvature and/or angles, patient age, genetic conditions, and/or any other variable. The system can also be configured to access the curvature of the spinal rod that the surgeon intends to implant into the patient. In some embodiments, the system can be configured to generate a predictive post-surgical spinal curvature for the patient based on the inputted of variables, in this example, the patient characteristics and the curvature of the spine rod to be implanted into the patient.

As one of ordinary skill will appreciate, the systems disclosed herein can be applied to a myriad of surgical procedures and is not intended to be limited to spinal surgeries. For example, the systems disclosed herein can be applied to any kind of surgery, including but not limited orthopedic surgeries, such as, neck, head, hand, foot, leg, and arm surgeries.

In some embodiments, the system is configured to generate a predictive model for predicting post-surgical parameters. In some embodiments, the system is configured to generate the predictive model by selecting a dataset comprising preoperative and/or postoperative data for one or more patients. As a non-limiting example, in some embodiments, the system is configured to identify all cases with PJK (proximal junctional kyphosis) and remove such cases from the dataset. In some embodiments, the system is configured to remove all pediatric cases from the dataset. In some embodiments, removal of the pediatric cases can be based on prior knowledge of the cases in the dataset.

In some embodiments, the system is configured to split data based on instrumented levels into different groups. For example, the system can be configured to split the dataset into a first group wherein there is instrumentation at L1-L5 and at S1—Iliac, and into a second group wherein there is instrumentation at T10-T12 and at S1—Iliac. For each group, the system, in some embodiments, is configured to split data into a training set and a testing set (for example, ~75% of the data for the training set and ~25% of the data for the testing set).

In some embodiments, the system is configured to select one or more input parameters, for example, age, PI pre-op value, PT pre-op value, LL pre-op value, TK pre-op value, SVA pre-op value, lower instrumented level, upper instrumented level, LL post-op target value, surgeon, weight, shape of the preoperative spline, preoperative x-ray, or the like. In some embodiments, the system is configured to standardize the range of input parameters and/or utilize a scaling methodology.

In some embodiments, the system is configured to standardize the data based on the training set. In some embodiments, the system is configured to select a first model type from a plurality of model types, such as for example linear models, neural networks, deep learning, SVR, or the like. In some embodiments, the system is configured to select the best model using cross validation. In some embodiments, the system is configured to perform cross validation by splitting the data set into a new training set and a new testing set. In some embodiments, the system is configured to train the model with the new training set and evaluate the results with the new testing set.

In some embodiments, the system is configured to repeat the training process until each data has been once and only once in a testing set. In some embodiments, the system is configured to train the model selected with the training set. In some embodiments, the system is configured to utilize a linear model named least-angle regression (LARS) with regularization and variable selection algorithm least absolute shrinkage and selection operator (LASSO). In some embodiments, the system is configured to test the trained model with the testing set to determine whether the trained model satisfies an accuracy threshold level. In some embodiments, the system is configured to utilize the trained model to compare with a proposed surgical plan to determine whether the surgical plan is optimal for the patient and/or will produce optimal post-operative surgical results for the patient having certain patient characteristics.

FIG. 15 is a flowchart illustrating an example embodiment(s) of predictive modeling. In the illustrated example embodiment, the system can be configured to access and/or retrieve one or more preoperative, intraoperative, and/or postoperative data sets at block 1502. The one or more datasets can be accessed and/or retrieved from one or more databases, such as the plan database 216 and/or operation database 218 among others.

In certain embodiments, the system can be configured to determine whether the retrieved or accessed dataset comprises postoperative data at block 1504. If a dataset comprises postoperative data, the system can be configured to identify one or more variables of interest, such as those described herein, from the postoperative data and/or related preoperative and/or intraoperative datasets at block 1506. Based in part on the identified one or more variables, the system can be configured to train a predictive modeling algorithm at block a 1508 according to one or more processes or techniques described herein. This training process and/or technique and/or portion thereof can be repeated as necessary. For example, in certain embodiments, the system can be configured to repeat the training algorithm and/or a portion thereof as additional data becomes available, such as data from an additional patient and/or additional postoperative data from a known patient or the like.

In some embodiments, if the retrieved or accessed dataset is for a new case, and as such does not comprise postoperative data the system can be configured to apply one or more predictive modeling algorithms to such input preoperative data. In particular, in certain embodiments, the system can be configured to identify one or more variables from the input preoperative data and/or compare the same with one or more other datasets at block 1510. In some embodiments, based on the comparison and/or other data analysis, the system can apply one or more predictive modeling algorithms to the input preoperative data. Subsequently, in some embodiments, the system can be configured to generate one or more predicted surgical outcomes and/or plan and/or one or more variables thereof based on the predictive model at block 1512. In certain embodiments, based at least in part on the resulting surgical plan and/or one or more variables thereof, the system can be configured to produce, modify, select, and/or provide guidance for selection of one or more spinal implants at block 1514, such as spinal rods, cages, and/or screws.

Other Embodiments for Predictive Modeling

In some embodiments, the system is configured to perform a computer-implemented method that is configured to generate a predictive model for determining post-operative parameters, such as thoracic kyphosis or pelvic tilt, wherein the computer-implemented method comprises accessing a dataset from an electronic database, the dataset comprising data about the patient (for example, an X-ray images or clinical information) and the surgery strategy (for example, upper instrumented vertebra, lower instrumented vertebra, or the like). In some embodiments, the computer-implemented method is configured to define in the dataset which parameters should be inputs of the model and which parameters should be outputs of the model. For example, outputs of the model can be the parameters that the system is configured to be predicted.

In some embodiments, the system is configured to optionally divide the dataset into a plurality of categories based on the spinal surgery domain knowledge, for example, the dataset can be configured to separate adult cases and pediatric cases. In some embodiments, the system can be configured to generate a predictive model for each category. In some embodiments, the system is configured to separate the data into a first subcategory and a second subcategory, wherein the first subcategory is used for training and the second subcategory is for testing the predictive model. In some embodiments, the system is configured to standardize the data using the first category.

In some embodiments, the system is configured to select a model algorithm, for example, neural network, support vector regression, linear models, or the like. In some embodiments, the system is configured to select the model based on using a cross validation strategy. In some embodiments, the system is configured to input one or more input values into the model based on the first subcategory to train the statistical models based on the output values of the first subcategory. In some embodiments, the system is configured to input one or more input data values in the generated trained model and compare the outputs generated by the model with the output values of the first subcategory. In certain embodiments, based on the foregoing comparison, a model is generated and the performance of the model is known. In some embodiments, the system is configured to store the first trained statistical model in a data repository. In some embodiments, the system comprises a computer processor and electronic memory. In certain embodiments, one or more of the above-identified processes or techniques are repeated for each of the categories defined by when dividing the dataset based on a spinal surgery domain knowledge block as described above.

In some embodiments, the system is configured to perform a computer-implemented method for generating a predictive model for estimating post-operative parameters, wherein the computer-implemented method comprises accessing a dataset from an electronic database, the dataset comprising data collected from one or more patients and spinal surgical strategy employed for the one or more patients. In some embodiments, the system is configured to divide the dataset into one or more categories based on spinal surgery domain knowledge. In some embodiments, the system is configured to for each category, separate the data into a first subcategory and a second subcategory, wherein the first subcategory is used for training and the second subcategory is for testing the predictive model.

In some embodiments, the system is configured to standardize the data in the first subcategory. In some embodiments, the system is configured to select a model algorithm to the data in the first subcategory. In some embodiments, the system is configured to input a first set of input values from the first subcategory into the model algorithm to train the predictive model based on a first set of output values from the first subcategory. In some embodiments, the system is configured to input a second set of input values from the second subcategory into the trained predictive model and comparing results generated by the trained predictive model with a second set of output values from the second subcategory. In some embodiments, the system is configured to store in a data repository the trained predictive model for implementation or future use. In some embodiments, the post-operative parameters comprise one or more of thoracic kyphosis or pelvic tilt. In some embodiments, the system comprises a computer processor and electronic memory.

In some embodiments, the data collected from one or more patients comprise one or more of an x-ray or clinical information. In some embodiments, the surgical strategy employed for the one or more patients comprises data relating to one or more of upper instrumented vertebra or lower instrumented vertebra. In some embodiments, the spinal surgery domain knowledge comprises one or more of adult cases or pediatric cases. In some embodiments, the model algorithm comprises one or more of a neural network, support vector regression, or linear model or the like. In some embodiments, the model algorithm is selected using a cross-validation strategy.

In some embodiments, the system is configured to perform a computer-implemented method for generating a predictive model for estimating post-operative thoracic kyphosis and pelvic tilt parameters, wherein the computer-implemented method comprises accessing a dataset from an electronic database, the dataset comprising data from spinal surgeries, wherein the spinal surgeries involve at least an upper instrumented vertebra and a lower instrumented vertebra. In some embodiments, the system is configured to analyze the dataset to divide the dataset into a plurality of categories, the plurality of categories comprising a first category comprising data from surgeries, wherein the upper instrumented vertebra is positioned between L1 and L5 vertebrae and the lower instrumented vertebra is positioned between S1 and iliac.

In some embodiments, the system is configured to select the first category, and access the data from the surgeries, the data comprising one or more of patient ages, pelvic incidence pre-operative values, pelvic tilt pre-operative values, lumbar lordosis pre-operative values, thoracic kyphosis pre-operative values, sagittal vertical axis pre-operative values, lower instrumented vertebra values, upper instrumented vertebra values, or lumbar lordosis post-operative target values for each of the surgeries in the first category. In some embodiments, the system is configured to standardize the data in the first category.

In some embodiments, the system is configured to separate the data into a first subcategory and a second subcategory, wherein the first subcategory is used for training and the second subcategory is for testing the predictive model for determining the post-operative thoracic kyphosis and pelvic tilt parameters. In some embodiments, the system is configured to input pre-operative data values in the first subcategory into a plurality of statistical models to train the statistical models based on the post-operative data values. In some embodiments, the system is configured to input pre-operative data values in the second subcategory into the plurality of trained statistical models and comparing output values from the plurality of trained statistical models with post-operative data values in the second subcategory.

In some embodiments, the system is configured to select a first trained statistical model from the plurality of trained statistical models, wherein the first trained statistical model generated an output values nearest to the post-operative data values based on the comparing. In some embodiments, the system is configured to store in electronic memory the first trained statistical model. In some embodiments, the system comprises a computer processor and electronic memory.

In some embodiments, the system is configured to perform a computer-implemented method for generating a surgical plan based on a predictive model for estimating post-operative parameters, the computer-implemented method comprising accessing one or more medical images of a portion of a spine of a patient. In some embodiments, the system is further configured to analyze the one or more medical images to determine one or more pre-operative variables relating to the spine of the patient, wherein the one or more pre-operative variables comprise at least one of UIL, LIL, age of the patient, pelvic incidence pre-operative values, pelvic tilt pre-operative values, lumbar lordosis pre-operative values, thoracic kyphosis pre-operative values, or sagittal vertical axis pre-operative values. In some embodiments, the system is configured to generate a prediction of one or more post-operative variables based at least in part on applying a predictive model, wherein the predictive model is generated by one or more of the following processes.

In some embodiments, the predictive model is configured to access a dataset from an electronic database, the dataset comprising data collected from one or more previous patients and spinal surgical strategy employed for the one or more previous patients. In some embodiments, the predictive model is configured to divide the dataset into one or more categories based on spinal surgery domain knowledge. In some embodiments, the predictive model is configured to standardize the data in the first subcategory.

In some embodiments, the predictive model is configured to select a model algorithm to the data in the first subcategory. In some embodiments, the predictive model is configured to input a first set of input values from the first subcategory into the model algorithm to train the predictive model based on a first set of output values from the first subcategory. In some embodiments, the predictive model is configured to input a second set of input values from the second subcategory into the trained predictive model and comparing results generated by the trained predictive model with a second set of output values from the second subcategory.

In some embodiments, the post-operative parameters of the predictive model comprise one or more of thoracic kyphosis or pelvic tilt. In some embodiments, the system is configured to generate a surgical plan based at least in part on the predicted one or more post-operative variables generated by the predictive model. In some embodiments, the surgical plan comprises at least one of a number of cages for implantation, location of implantation of cages, length of a spinal rod for implantation, or curvature of the spinal rod. In some embodiments, the system comprises a computer processor and electronic memory.

In some embodiments, the system is configured to perform a computer-implemented method for generating a surgical plan based on a predictive model for estimating post-operative thoracic kyphosis and pelvic tilt parameters, the computer-implemented method comprising accessing one or more medical images of a portion of a spine of a patient. In some embodiments, the system is further configured to analyze the one or more medical images to determine one or more pre-operative variables relating to the spine of the patient, wherein the one or more pre-operative variables comprise at least one of UIL, LIL, age of the patient, pelvic incidence pre-operative values, pelvic tilt pre-operative values, lumbar lordosis pre-operative values, thoracic kyphosis pre-operative values, or sagittal vertical axis pre-operative values. In some embodiments, the system is configured to generate a prediction of one or more post-operative variables based at least in part on applying a predictive model, wherein the predictive model is generated by one or more of the following processes.

In some embodiments, the predictive model is configured to access a dataset from an electronic database, the dataset comprising data from spinal surgeries, wherein the spinal surgeries involve at least an upper instrumented vertebra and a lower instrumented vertebra. In some embodiments, the predictive model is configured to analyze the dataset to divide the dataset into a plurality of categories, the plurality of categories comprising a first category comprising data from surgeries, wherein the upper instrumented vertebra is positioned between L1 and L5 vertebrae and the lower instrumented vertebra is positioned between S1 and iliac.

In some embodiments, the predictive model is configured to select the first category, and access the data from the surgeries, the data comprising one or more of patient ages, pelvic incidence pre-operative values, pelvic tilt pre-operative values, lumbar lordosis pre-operative values, thoracic kyphosis pre-operative values, sagittal vertical axis pre-operative values, lower instrumented vertebra values, upper instrumented vertebra values, or lumbar lordosis post-operative target values for each of the surgeries in the first category. In some embodiments, the predictive model is configured to standardize the data in the first category.

In some embodiments, the predictive model is configured to separate the data into a first subcategory and a second subcategory, wherein the first subcategory is used for training and the second subcategory is for testing the predictive model for determining the post-operative thoracic kyphosis and pelvic tilt parameters. In some embodiments, the predictive model is configured to input pre-operative data values in the first subcategory into a plurality of statistical models to train the statistical models based on the post-operative data values. In some embodiments, the predictive model is configured to input pre-operative data values in the second subcategory into the plurality of trained statistical models and comparing output values from the plurality of trained statistical models with post-operative data values in the second subcategory.

In some embodiments, the predictive model is configured to select a first trained statistical model from the plurality of trained statistical models, wherein the first trained statistical model generated an output values nearest to the post-operative data values based on the comparing. In some embodiments, the predicted one or more post-operative variables comprises at least one of lumbar lordosis post-operative target values, thoracic kyphosis post-operative values, or sagittal vertical axis post-operative values. In some embodiments, the system is configured to generate a surgical plan based at least in part on the predicted one or more post-operative variables. In some embodiments, the surgical plan comprises at least one of a number of cages for implantation, location of implantation of cages, length of a spinal rod for implantation, or curvature of the spinal rod. In some embodiments, the system comprises a computer processor and electronic memory.

Data Elements/Parameters for Predictive Modeling

In some embodiments, in order to perform one or more processes or techniques relating to predictive modeling, the system can be configured to receive, access, and/or obtain one or more of the following data elements or parameters that can be collected from one or more patients.

In particular, in certain embodiments, the system can be configured to receive, access, and/or obtain one or more demographic characteristics, such as for example, age at surgery, gender, height, weight, activity level, date of narcotics, disability, education, home care requirements, insurance coverage, job, race, date of return to work/school/sport, socioeconomic status, and/or the like.

In some embodiments, the system can be configured to receive, access, and/or obtain one or more patient-reported outcomes, such as for example, Oswestry Disability Index (ODI), Neck Disability Index (NDI), Scoliosis Research Society (SRS-22), Nurick, and/or the like.

In certain embodiments, the system can be configured to receive, access, and/or obtain one or more radiographic parameters, such as for example, preoperative and/or postoperative data such as T4-T12 TK (=Thoracic Kyphosis), L1-S1 LL (=Lumbar Lordosis), Lateral C7 to Sacrum SVA (=Sagital Vertical Axis), PT (=Pelvic Tilts), PI (Pelvic Incidence), L1-SITK (=Thoracic Kyphosis), and/or the like.

In some embodiments, the system can be configured to receive, access, and/or obtain one or more other radiographic parameters as well, such as Apical Translation ThL/Lumbar Curve—CSVL, C2T1 Pelvic Angle (=CTPA, °), C2C7 SVA (mm) (=Sagital Vertical Axis), Cervical Lordosis, Lenke Classification, Proximal Jonctionnal Kelphosis (PJK), Rod Tracing, SS, T1 Slope (TIS, °) T1 Tilt Angle and Direction, T10-L2, T12-S1 Lombar Lordodis, T2-T12, T2-T5, T5-T12 Thoracic Kyphosis, Th Apex, Th Bend, Th Curve, Th Curve Levels, (Th/L Lumbar Apex, Th/L Lumbar Curve, Th/L Lumbar Curve Direction of curve, Th/L Lumbar Curve Levels), T1 Pelvic Angle (TPA), Anatomical Kyphosis, Anatomical Lordosis, Cobb Angles, Coordinates of all vertebra corners in the sagittal and coronal planes and the femoral heads, Pre-op or post-operative data like Apical Translation Th Curve-C7 Plumb, Apical Translation Th Curve—CSVL, Computerized tomography Performed, Disc Angulation Below Espace Instrumental Vertebral (EIV), EIV Angulation, EIV Translation, Coronal C7 to CSVL, TIS-CL (°), TH CUrve—Direction od Curve, Tri-Radiate Cartilage, Upper Th Bend, Upper Th Curve, Upper Th Curve—Direction of Curve, Upper Th Curve—Levels, External Auditory Meadus, Pelvic Obliquity, Pelvic Version, Acetabular Index, and/or the like.

In some embodiments, the systems disclosed herein can be configured to generate spinal surgical strategies comprising one or more surgical data parameters, such as Instrumentation Material, Instrumentation Size, Instrumentation Type, Lowermost Instrumented, MIS (=Minimal Invasive Surgery), Number of Levels, Osteotomies Performed, Rod Bending Degrees and/or Angles, Rod Cutting Parameters, Uppermost Instrumented Parameters, Upper Instrumented Vertebrae (UIV), Lower Instrumented Vertebrae (LIV), Surgeon, surgical techniques (in some embodiments, use machine learning algorithms to analyze surgeon's surgical techniques to be able to simulate the surgery and the rod that will match surgeon's expectations), radiography as an image, scanner, MRI (image or set of images), and/or the like.

In an example embodiment, a first set of input values for preoperative and/or postoperative data can include the following: T4-T12 TK (=Thoracic Kyphosis), L1-S1 LL (=Lumbar Lordodis), Lateral C7 to Sacrum (SVA) (=Sagittal Vertical Axis), Lowermost Instrumented Vertebrae (LIV), Uppermost Instrumented Vertebrae (UIV), Pelvic Tilt, Age at the time of surgery, and Pelvic Incidence (PI).

In an example embodiment, a first set of output values for preoperative and/or postoperative data can include the following: T4-T12 TK (=Thoracic Kyphosis), L1-S1 LL (=Lumbar Lordosis), and Pelvic Tilt.

System

FIG. 16 is a schematic diagram illustrating an embodiment of a system for developing patient-specific spinal treatments, operations, and procedures. In some embodiments, a main server system 1602 may be comprised of an image analysis module 1604, a case simulation module 1606, an intra-operative tracking module 1608, a data utilization module 1610, a predictive modeling module 1628, a plan database 1612, an operation database 1614, a surgeon database 1616, and/or a literature database 1618. The main server system can be connected to a network 1620. The network can be configured to connect the main server to one or more implant production facility systems 1626, one or more medical facility client systems 1622, and/or one or more user access point systems 1624.

The image analysis module 1604 may function by providing image analysis and/or related functions as described herein. The case simulation module 1606 may function by performing surgical planning, case simulation, and/or related functions as described herein. The intra-operative tracking module 1608 may function by performing intra-operative tracking and/or related functions as described herein. The data utilization module 1610 may function by retrieving and/or storing data from and to one or more databases and/or related functions as described herein. The predictive modeling module 1628 may function by performing one or more predictive modeling processes as described herein.

The plan database 1612 may provide a collection of all plans that have been generated by the system and/or related data. The operation database 1614 may provide a collection of all surgical operations that have been performed utilizing the system and/or related data. The surgeon database 1616 may provide a collection of all surgeons who have utilized the system and/or related data, such as surgeon preferences, skill levels, or the like. The literature database 1618 may provide a collection of scientific literature related to spinal surgery.

Computer System

Figure 17:
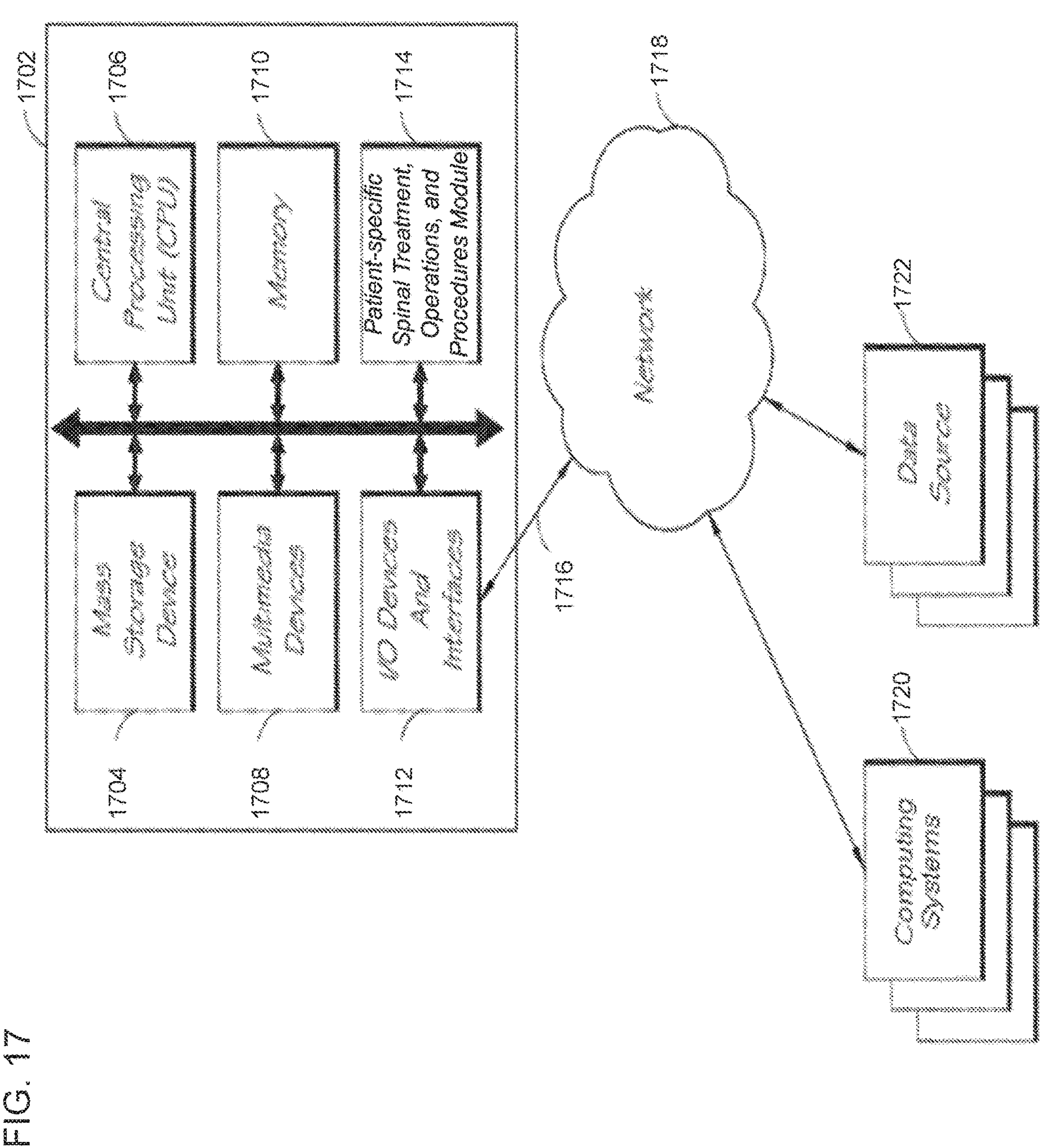
FIG. 17 is a block diagram depicting an embodiment of a computer hardware system configured to run software for implementing one or more embodiments of a system for developing patient-specific spinal treatments, operations, and procedures.

In some embodiments, the systems, processes, and methods described herein are implemented using a computing system, such as the one illustrated in FIG. 17. The example computer system 1702 is in communication with one or more computing systems 1720 and/or one or more data sources 1722 via one or more networks 1718. While FIG. 17 illustrates an embodiment of a computing system 1702, it is recognized that the functionality provided for in the components and modules of computer system 1702 may be combined into fewer components and modules, or further separated into additional components and modules.

The computer system 1702 can comprise a patient-specific spinal treatment, operations, and procedures module 1714 that carries out the functions, methods, acts, and/or processes described herein. The patient-specific spinal treatment, operations, and procedures module 1714 is executed on the computer system 1702 by a central processing unit 1706 discussed further below.

In general the word "module," as used herein, refers to logic embodied in hardware or firmware or to a collection of software instructions, having entry and exit points. Modules are written in a program language, such as JAVA, C or C++, PYPHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems, and may be stored on or within any suitable computer readable medium, or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 1702 includes one or more processing units (CPU) 1706, which may comprise a microprocessor. The computer system 1702 further includes a physical memory 1710, such as random access memory (RAM) for temporary storage of information, a read only memory (ROM) for permanent storage of information, and a mass storage device 1704, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 1702 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1702 includes one or more input/output (I/O) devices and interfaces 1712, such as a keyboard, mouse, touch pad, and printer. The I/O devices and interfaces 1712 can include one or more display devices, such as a monitor, that allows the visual presentation of data to a user. More particularly, a display device provides for the presentation of GUIs as application software data, and multi-media presentations, for example. The I/O devices and interfaces 1712 can also provide a communications interface to various external devices. The computer system 1702 may comprise one or more multi-media devices 1708, such as speakers, video cards, graphics accelerators, and microphones, for example.

The computer system 1702 may run on a variety of computing devices, such as a server, a Windows server, a Structure Query Language server, a Unix Server, a personal computer, a laptop computer, and so forth. In other embodiments, the computer system 1702 may run on a cluster computer system, a mainframe computer system and/or other computing system suitable for controlling and/or communicating with large databases, performing high volume transaction processing, and generating reports from large databases. The computing system 1702 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 1702 illustrated in FIG. 17 is coupled to a network 1718, such as a LAN, WAN, or the Internet via a communication link 1716 (wired, wireless, or a combination thereof). Network 1718 communicates with various computing devices and/or other electronic devices. Network 1718 is communicating with one or more computing systems 1720 and one or more data sources 1722. The patient-specific spinal treatment, operations, and procedures module 1714 may access or may be accessed by computing systems 1720 and/or data sources 1722 through a web-enabled user access point. Connections may be a direct physical connection, a virtual connection, and other connection type. The web-enabled user access point may comprise a browser module that uses text, graphics, audio, video, and other media to present data and to allow interaction with data via the network 1718.

Access to the patient-specific spinal treatment, operations, and procedures module 1714 of the computer system 1702 by computing systems 1720 and/or by data sources 1722 may be through a web-enabled user access point such as the computing systems' 1720 or data source's 1722 personal computer, cellular phone, smartphone, laptop, tablet computer, e-reader device, audio player, or other device capable of connecting to the network 1718. Such a device may have a browser module that is implemented as a module that uses text, graphics, audio, video, and other media to present data and to allow interaction with data via the network 1718.

The output module may be implemented as a combination of an all-points addressable display such as a cathode ray tube (CRT), a liquid crystal display (LCD), a plasma display, or other types and/or combinations of displays. The output module may be implemented to communicate with input devices 1712 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1702 may comprise a physical or logical connection established between a remote microprocessor and a mainframe host computer for the express purpose of uploading, downloading, or viewing interactive data and databases online in real time. The remote microprocessor may be operated by an entity operating the computer system 1702, including the client server systems or the main server system, and/or may be operated by one or more of the data sources 1722 and/or one or more of the computing systems 1720. In some embodiments, terminal emulation software may be used on the microprocessor for participating in the micro-mainframe link.

In some embodiments, computing systems 1720 who are internal to an entity operating the computer system 1702 may access the patient-specific spinal treatment, operations, and procedures module 1714 internally as an application or process run by the CPU 1706.

The computing system 1702 may include one or more internal and/or external data sources (for example, data sources 1722). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1702 may also access one or more databases 1722. The databases 1722 may be stored in a database or data repository. The computer system 1702 may access the one or more databases 1722 through a network 1718 or may directly access the database or data repository through I/O devices and interfaces 1712. The data repository storing the one or more databases 1722 may reside within the computer system 1702.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

Although the embodiments discussed herein generally relate to patient-specific spinal treatment, operations, and procedures, the systems, methods, and devices disclosed herein can be used for any non-spinal patient-specific treatment, operations, and procedure as well. Also, the systems, methods, and devices disclosed herein can be used with x-ray, MRI, CT, or any other imaging systems or devices that produce two-dimensional and/or three-dimensional medical image or video data.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

What is claimed is:

1. A system comprising:

one or more computer readable storage devices configured to store a plurality of computer executable instructions; and one or more hardware computer processors in communication with the one or more computer readable storage devices and configured to execute the plurality of computer executable instructions in order to cause the system to:

receive tracking data comprising position and/or orientation information of two or more vertebrae of a patient in substantially real time during a spinal surgery;

compare the received position and/or orientation of the two or more vertebrae with a predetermined surgical plan comprising desired position and orientation data of the two or more vertebrae, and generate an audible and/or visible alert when the position and/or orientation of the two or more vertebrae satisfies a predetermined threshold;

wherein the desired position and orientation data of the two or more vertebrae is based on:

one or more medical images of the patient, a desired clinical outcome for the patient, and data related to previous spinal surgeries of one or more other patients having the desired clinical outcome; and generate guidance instructions for performing the spinal surgery based on the comparison of the received position and/or orientation of the two or more vertebrae with the predetermined surgical plan for the patient.

2. The system of claim 1, further comprising sensors attached to the two or more vertebrae of the patient, wherein the instructions that cause the system to receive the position and/or orientation information of the two or more vertebrae comprise instructions that cause the system to receive the position and/or orientation information from the sensors attached to the two or more vertebrae.

3. The system of claim 2, wherein the sensors are configured to be attached to the two or more vertebrae in a configuration such that two of three axes of position data to be collected by the sensors are on a plane assumed to be substantially parallel with a determinate angle to a sagittal plane of the patient.

4. The system of claim 1, wherein the instructions further cause the system to determine a desired curvature of a spine of the patient based on predicted post-operative parameters, the predicted post-operative parameters based on the data related to previous spinal surgeries of the one or more other patients.

5. The system of claim 1, wherein the one or more medical images of the patient comprise a pre-operative sagittal x-ray image of a spine of the patient.

6. The system of claim 1, wherein the instructions further cause the system to continuously generate guidance instructions for performing the spinal surgery until a spine of the patient is adjusted to a predetermined acceptable level.

7. The system of claim 1, wherein data related to previous spinal surgeries of the one or more other patients comprises data related to similar cases based on patient age, severity of deformation, or bone strength or density.

8. The system of claim 1, wherein the desired position and orientation data of the two or more vertebrae is further based at least in part on one or more preferences of a surgeon performing the spinal surgery for the patient.

9. The system of claim 1, wherein the desired position and orientation data of the two or more vertebrae is further based on modifying the accessed medical images to simulate an outcome of the spinal surgery for the patient.

10. The system of claim 9, wherein modifying the accessed medical images comprises simulating, on the one or more medical images, implantation of a spinal rod to a vertebral segment of interest.

11. The system of claim 9, wherein modifying the accessed medical images comprises partitioning at least one medical image into two or more portions and rotating at least one portion with respect to another portion to obtain a depiction of post-operative results or objectives.

12. The system of claim 1, wherein the desired position and orientation data of the two or more vertebrae is based on at least two of the one or more medical images of the patient after the at least two of the one or more medical images have been calibrated and scaled based on at least one common feature.

13. The system of claim 1, wherein the instructions further cause the system to display the position of the two or more vertebrae on a display based on the tracking data.

14. The system of claim 1, wherein the instructions further cause the system to generate a report comprising an overlay comprising at least two images of a spine of the patient, the at least two images obtained pre-operation, intra-operation, and/or post-operation.

15. The system of claim 1, wherein the instructions that cause the system to generate the guidance instructions comprise instructions that cause the system to recommend an implant dimension.

16. The system of claim 15, wherein the instructions that cause the system to recommend the implant dimension comprise instructions that cause the system to recommend the implant dimension based on a length of one or more ligaments determined from the one or more medical images.

17. The system of claim 1, wherein the predetermined surgical plan is based on a predictive model.

18. The system of claim 1, wherein the plurality of computer executable instructions that cause the system to receive the tracking data comprise computer executable instructions that cause the system to receive intraoperative fluoroscopy.

* * * * *